United States Patent
Mechali et al.

(10) Patent No.: US 10,131,913 B2
(45) Date of Patent: Nov. 20, 2018

(54) PURIFICATION PROCESS OF NASCENT DNA

(71) Applicant: CENTRE NATIONAL DE LA RECHERCHE SCIENTIFIQUE (CNRS), Paris (FR)

(72) Inventors: Marcel Mechali, Montferrier sur Lez (FR); Philippe Coulombe, Montpellier (FR); Christelle Cayrou, Montpellier (FR); Eric Rivals, Montpellier (FR); Paulina Prorok, Montpellier (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 26 days.

(21) Appl. No.: 14/681,351

(22) Filed: Apr. 8, 2015

(65) Prior Publication Data
US 2015/0267208 A1    Sep. 24, 2015

Related U.S. Application Data

(63) Continuation-in-part of application No. 13/393,259, filed as application No. PCT/EP2010/062736 on Aug. 31, 2010, now abandoned.

(60) Provisional application No. 61/238,315, filed on Aug. 31, 2009.

(51) Int. Cl.
*C12N 15/64*    (2006.01)
*C12N 15/69*    (2006.01)

(52) U.S. Cl.
CPC ............ *C12N 15/64* (2013.01); *C12N 15/69* (2013.01)

(58) Field of Classification Search
None
See application file for complete search history.

(56) References Cited

U.S. PATENT DOCUMENTS

| | | | |
|---|---|---|---|
| 4,987,066 | A | 1/1991 | Epplen |
| 5,426,180 | A | 6/1995 | Kool |
| 5,686,288 | A | 11/1997 | MacDonald et al. |
| 5,695,933 | A | 12/1997 | Schalling et al. |
| 2001/0053519 | A1 | 12/2001 | Fodor et al. |

FOREIGN PATENT DOCUMENTS

| | | |
|---|---|---|
| WO | 9827200 | 6/1998 |
| WO | 0216419 | 2/2002 |
| WO | 2004015063 | 2/2004 |
| WO | 2006088860 | 8/2006 |
| WO | 2009099326 | 8/2009 |

OTHER PUBLICATIONS

GenBank BU960634.1 (created Oct. 18, 2002).*
pDNR-LIB Donor Vector Information. Retrieved on Nov. 8, 2016 from the internet: http://www.takara.co.kr/file/manual/pdf/PT3508-5.pdf.*
Xu et al. Gene. 2001. 272:149-156.*
Walberg et al. Nucleic Acids Research. 1981. 9(20):5411-5421.*
Nielsen et al. Mol Gen Genet. 1994. 242:280-288.*
Mizuguchi et al. Human Gene Therapy. 1999. 10:2013-2017.*
Addgene. Retrieved on Apr. 17, 2017 from the internet: https://www.addgene.org/browse/sequence_vdb/2110/.*
Paixao et al. Molecular and Cellular Biology. 2004. 24(7):2958-2967.*
GenBank M94336. Entered May 24, 1996. Retrieved on Dec. 7, 2017 from the internet: https://www.ncbi.nlm.nih.gov/nucleotide/186920?report=genbank&log$=nucltop&blast_rank=1&RID=1XJE44GP015.*
Bryda et al., BioTechniques. 2006. 41(6): 715-719.
GenBank 3 (NW_001030719.1; Jun. 20, 2007).
Blast Alignment (retrieved on Dec. 2, 2014 from the Internet: http://blast.ncbi.nlm.nih.gov/Blast.cgi#alnHdr_83280973).
Gomez et al. Genome Biology. 2005. 6: R369.
GenBank Accession No. BX054346.1 (Apr. 22, 2005).
GenBank Accession No. AF028017.1 (Jan. 2, 1998).
Caddle et al., J. Mol. Biol. 1990. 211: 19-33.
Ji et al., "In vitro expansion of GGC:GCC repeats: identification of the preferred strand of expansion", Nucleic Acids Research, 1996, vol. 24, No. 14, pp. 2835-2840.
Parson et al., "Contrasting genetic diversity relationships are revealed in rice (*Oryza sativa* L.) using different marker types", Molecular Breeding, 1997, vol. 3, pp. 115-125, XP001149290.
Blast alignment with NC_018914.2.
Blast alignment with NC_018915.2.
Blast alignment with NC_018916.2.
Van Dam. Genome Res. 2002. 12(1): 145-152.
Marie-Noelle Prioleau et al: "Replication of the chicken beta-globin locus: Early-firing origins at the 5' HS4 insulator and the rho- and betaA-globin genes show opposite epigenetic modifications.", Molecular and Cellular Biology, vol. 23, No. 10, May 2003 (May 2003), pp. 3536-3549, XP002603564.
Jean-Charles Cadoret et al: "Genome-wide studies highlight indirect links between human replication origins and gene regulation" Proceedings of the National Academy of Sciences of the United States of America, vol. 105, No. 41. Oct. 2008 (Oct. 2008), pp. 15837-15842, XP002603565.
Maria Gomez et al: "Overreplication of short DNA regions during S phase in human cells", Genes & Development, vol. 22, No. 3, Feb. 2008 (Feb. 2008), pp. 375-385, XP002603566.

(Continued)

*Primary Examiner* — Joseph G. Dauner
(74) *Attorney, Agent, or Firm* — Young & Thompson

(57) ABSTRACT

A method for initiating the replication of a deoxyribonucleic acid molecule includes inserting into the DNA at least one nucleic acid molecule representing a multicellular DNA replication origin. The replication origin contains at least nine nucleotides and contains at least three uninterrupted origin repeating elements (ORE), each ORE having the sequence $N_3GN_4$, wherein $N_3$ is T or G and $N_4$ is G or C. The method can confer autonomous replication properties to a non-self-replicating DNA molecule. A process for preparing a vector for use in said methods is also presented.

4 Claims, 56 Drawing Sheets

Specification includes a Sequence Listing.

(56) References Cited

OTHER PUBLICATIONS

Joana Sequeira-Mendes et al., "Transcription Initiation Activity Sets Replication Origin Efficiency in Mammalian Cells", PLOS Genetics, vol. 5, No. 4, Apr. 2009 (Apr. 2009), XP002603567.
Sapna Das-Bradoo et al., "Replication Initiation Point Mapping: Approach and Implications", Jan. 23, 2009 (Jan. 23, 2009). Methods in Molecular Biology, XP008127649.
Database EMBL [Online] Sep. 24, 2009 (Sep. 24, 2009), Sequence 17 from Patent WO2009099326.
Database Geneseq [Online] Nov. 1, 2007 (Nov. 1, 2007), "VIC-labeled probe for marker 30026 detection", XP002616997.
Database Geneseq [Online] Feb. 20, 2002 (Feb. 20, 2002), "Oligonucleotide Seq Id No. 5406 for detecting SNP TSC0001818", XP002616998.
Database Geneseq [Online] Mar. 12, 2002 (Mar. 12, 2002), "PCR primer (dCT) 6 used in method of identifying mircoorganisms", XP002616999.
International Search Report PCT/EP2010/062736 dated Feb. 2, 2011.

\* cited by examiner

PURIFICATION PROCESS OF NASCENT DNA

The present invention relates to a purification process of nascent DNA.

In metazoans, thousands of chromosomal sites are activated at each cell cycle to initiate DNA synthesis and permit total duplication of the genome. They all should be activated only once to avoid any amplification and maintain genome integrity. How these sites are defined remains elusive despite considerable efforts trying to unravel a possible replication origin code.

In *Saccharomyces cerevisiae*, DNA replication origins are specifically identified by specific DNA elements, called Autonomous Replication Sequence elements (ARS), which have a common AT-rich 11 bp specific consensus. However, sequence specificity identifies but not determines origin selection.

In multicellular organisms, it was more difficult to identify common features of DNA replication origins. No consensus sequence element has been found, which can have predictive value, although specific sites are recognized as DNA replication origins in chromosomes of somatic cells.

The identification of the sequence of DNA replication origin offers new perspectives in the comprehension of pathologies involving miss regulation of DNA replication, and new perspective in the cellular therapy, by using "humanized" vectors.

International application WO 98/27200 discloses a putative consensus sequence of human and mammalian replication origin. However, the consensus sequences disclosed in WO 98/27200 appears to be not representative of all the replications origins normally used in multicellular eukaryotic cells.

Prior art also discloses methods for purifying nascent DNA for mapping of DNA replication origins in multicellular eukaryotic cells [Prioleau et al. 2003, *Molecular and Cellular Biology*, 23(10), pages 3536-3549; Cadoret et al. 2008, *P.N.A.S.*, 105(41), pages 15837-15842; Gomez et al. 2008, *Genes & Development*, 22(3), pages 375-385; Sequeira-Mendes, 2009, *PloS Genetics*, 5(4)]. Prioleau et al. 2003, Molecular and Cellular Biology, 23(10), pages 3536-3549 disclose methods for purification of nascent strands. The method included sucrose gradients, heat denaturation and exonuclease digestion. The heat denaturation step eliminates proteins associated with nucleic acid molecules.

So, there is a need to provide a new consensus sequence representing all the DNA replication origins of a multicellular eukaryotic cell.

There is also a need to provide a new method for determining the DNA replication origins of a multicellular eukaryotic cell.

One aim of the invention is to provide a method for purifying nascent DNA in a large amount and with a very high purity.

One aim of the invention is to provide a method for identifying eukaryotic replication origin.

Another aim of the invention is to provide the sequence of said eukaryotic replication origin.

Another aim is the use of nascent DNA produced by said replication origin for providing a method of diagnosis.

The invention relates to the use of purified nascent DNA (hybrid RNA-DNA) for the implementation of a process allowing the mapping and the numbering of the active DNA replication origins of multi cellular eukaryotic cells, and the characterisation of the sequence of said replication origins, said process comprising

- a step of extracting a mixture of nucleic acid molecules, said mixture of nucleic acid molecules comprising DNA and hybrid RNA-DNA, from multi cellular eukaryotic cells
- a step of enrichment of hydrid RNA-DNA from said mixture by eliminating proteins associated with said nucleic acid molecules, and
- at least two step of elimination of DNA from the mixture to recover purified nascent DNA.

The initiation of new DNA strands at origins of replication in multicellular eukaryotic cells requires de novo synthesis of RNA primers by primase and subsequent elongation from RNA primers by DNA polymerase alpha. These nascent DNA are thus hybrid molecules consisting of a short molecule of RNA fused in its 3' end to a DNA molecule. The inventors have unexpectedly discovered that eliminating proteins associated with DNA (histones for instance), allow a large increase in the purifying efficiency of nascent DNA.

Also, the inventors have demonstrated that a double cycle of phosphorylation/digestion of lambda exonuclease also drastically enhances the purity of isolated nascent DNA.

The nascent DNA are purified, which means that said nascent DNA are substantially pure: after one step of exonuclease, contaminant DNA represent about 25% of the purified DNA.

According to the invention, at least two exonuclease treatments allows to eliminate contaminant DNA (after 2 steps: about 5% of DNA is present in the mixture, after 3 steps less than 2% of contaminant DNA is present in the mixture).

In one advantageous embodiment, the invention relates to the use as defined above, wherein said nascent DNA are produced by the active replication origins.

In one advantageous embodiment, the invention relates to the use of purified nascent DNA for mapping and numbering the active DNA replication origins as defined above, wherein said process is carried out by using multicellular organism totipotent cells. In totipotent cells, such as ES cells, all the DNA replication origins are active, to allow a rapid duplication of DNA In one advantageous embodiment, the invention relates to the use of purified nascent DNA for mapping and numbering the active DNA replication origins as defined above, wherein process is carried out by using multicellular organism differentiated cells.

In differentiated cells, not all the DNA replication origins are active.

In one advantageous embodiment, the invention relates to the use of purified nascent DNA for the characterisation of the sequence the active DNA replication origins as defined above, wherein said sequence consists of the nucleic acid sequences selected from the group comprising the following sequences:

$$5'-(N_7)_a(N_8)_b(GN_1N_2)_c(N_7)_d(N_8)_e-3' \quad \text{(SEQ ID NO: 1)}$$

wherein $N_1$ is a G or a A and $N_2$ is a pyridine or a A $$5'-(N_7)_a(N_8)_b(N_3GN_4)_c(N_7)_d(N_8)_e-3' \quad \text{(SEQ ID NO: 2)}$$

wherein $N_3$ is a T or a G base and $N_4$ is a G or a C, and $$5'-(N_7)_a(N_8)_b(N_5N_6G)_c(N_8)_d(N_9)_e-3' \quad \text{(SEQ ID NO: 3)}$$

wherein $N_s$ is different from $N_6$, $N_5$ is a G or a C and $N_6$ is a T or a A wherein c vary from 3 to 20 wherein $N_7$ and $N_8$ represent any nucleotide, wherein a and e independently from each other can be equal to 0, 1 2 or 3, or vary from about 15 to 30, and wherein b and d independently from each other can be equal to 0, 1 2 or 3 or vary from about 10 to 300, $N_8$ being such that if b vary from 10 to 300, $(N_8)_b$ represents a nucleic acid chain which is such that
- it contains from about 50% to about 100% of A,
- it contains from about 50% to about 100% of T,
- it contains from 0% to about 10% of G, and
- it contains from 0% to about 12% of C, $N_9$ being such that if d vary from 10 to 300, $(N_9)_d$ represents a nucleic acid chain which is such that
- it contains from about 50% to about 100% of A,
- it contains from about 50% to about 100% of T,
- it contains from 0% to about 10% of G, and
- it constrains from 0% to about 12% of C.

or any fragment of the above sequence consisting of at least 9 nucleotides.

In the invention pyridine means T or C, or U for RNA.

In one other embodiment, the invention relates to the use of purified nascent DNA as defined above, wherein said nucleic acid sequence being such that
- it contains from about 33% to about 66% of G,
- it contains from about 27% to about 33% of C,
- it contains from about 0% to about 12% of A,
- it contains from about 0% to about 15% of T, and
- it has a minimal consensus sequence chosen among the following consensus sequences:

$$5'-N1N2G-3'$$

wherein N1 is a G or a A and N2 is a pyridine or a A $$5'-N3GN4-3'$$

wherein N3 is a T or a G base and N4 is a G or a C, and $$5'-GN5N6-3'$$

wherein Ns is different from N6, N5 is a G or a C and N6 is a T or a A said minimal consensus sequence being repeated from 3 to 20 times without interruption between said repeated minimal consensus sequence.

In one other embodiment, the invention relates to the use of purified nascent DNA as defined above, wherein said nucleic acid sequence consists of the following sequence SEQ ID NO: 4:

$$5'-SHGCYGSYGGMGCYGSHGSTG-3',$$

or any fragment of said nucleic acid sequence consisting of at least 9 nucleotides.

In the invention, the following nomenclature in nucleic acid sequence is used:
R represents A or G
Y represents C or T
M represents A or C
K represents G or T
S represents G or C
W represents A or T
B represents G, T or C D represents G, A or T
H represents A, C or T
V represents G, C or A, and
N represents any nucleotide (A, T, G or C)

In one other embodiment, the invention relates to the use of purified nascent DNA as defined above, wherein said nucleic acid sequence consists of the following sequence SEQ ID NO: 5:

$$5'-CKGYKGCKGCDGCKGCDGYKG-3'$$

or any fragment of said nucleic acid sequence consisting of at least 9 nucleotides.

In one other embodiment, the invention relates to the use of purified nascent DNA as defined above, wherein said nucleic acid sequence consists of one of the following sequences

| Sequence | SEQ ID NO |
|---|---|
| GTCCCAGTCCCAG | (SEQ ID NO: 6) |
| TGCTGCTGCTGCT | (SEQ ID NO: 7) |
| TATATATATATAT | (SEQ ID NO: 8) |
| AGCAGCAGCAGCA | (SEQ ID NO: 9) |
| GTTGCTGCTGCTG | (SEQ ID NO: 10) |
| TCAGACATCTTAG | (SEQ ID NO: 11) |
| AGCAGCAGCAACA | (SEQ ID NO: 12) |
| CAGACATCTTAGG | (SEQ ID NO: 13) |
| AGACATCTTAGGC | (SEQ ID NO: 14) |
| CAGCAGCAGCAGC | (SEQ ID NO: 15) |
| TAACGTGTGGTGA | (SEQ ID NO: 16) |
| TGTTGCTGCTGCT | (SEQ ID NO: 17) |
| CAGCAGCAGCAAC | (SEQ ID NO: 18) |
| TGCTGCTGC | (SEQ ID NO: 19) |
| CAGCAGCAG | (SEQ ID NO: 20) |
| CTGCTGCTG | (SEQ ID NO: 21) |
| CTCTCTCTCTCT | (SEQ ID NO: 22) |
| TCTCTCTCTCTC | (SEQ ID NO: 23) |
| AGCTGGGCGGCA | (SEQ ID NO: 24) |
| CAGCTGGGCGGC | (SEQ ID NO: 25) |
| GCTGGGCGGCAG | (SEQ ID NO: 26) |
| AGCAGCTGGACAC | (SEQ ID NO: 27) |
| CAGCAGCTGGACA | (SEQ ID NO: 28) |
| GCAGCAGCTGGAC | (SEQ ID NO: 29) |
| CAGCTGGACACAC | (SEQ ID NO: 30) |
| AGCAGACTGGGCG. | (SEQ ID NO: 31) |

The invention also relates to an isolated nucleic acid sequence representing an multi cellular DNA replication origins, wherein said nucleic acid sequence consists of one of the following sequences the nucleic acid sequences selected from the group comprising the following sequences:

5'-(N$_7$)$_a$(N$_8$)$_b$(GN$_1$N$_2$)$_c$(N$_7$)$_d$(N$_8$)$_e$-3'   (SEQ ID NO: 1)

wherein N$_1$ is a G or a A and N$_2$ is a pyridine or a A

5'-(N$_7$)$_a$(N$_8$)$_b$(N$_3$GN$_4$)$_c$(N$_7$)$_d$(N$_8$)$_e$-3'   (SEQ ID NO: 2)

wherein N$_3$ is a T or a G base and N$_4$ is a G or a C, and

5'-(N$_7$)$_a$(N$_8$)$_b$(N$_5$N$_6$G)$_c$(N$_8$)$_d$(N$_9$)$_e$-3'   (SEQ ID NO: 3)

wherein N$_5$ is different from N$_6$, N$_5$ is a G or a C and N$_6$ is a T or a A
wherein c vary from 3 to 20
wherein N$_7$ and N$_8$ represent any nucleotide,
wherein a and e independently from each other can be equal to 0, 1, 2 or 3, or vary from about 15 to 30, and
wherein b and d independently from each other can be equal to 0, 1, 2 or 3 or vary from about 10 to 300,
N$_8$ being such that if b vary from 10 to 300, (N$_8$)$_b$ represents a nucleic acid chain which is such that
it contains from about 50% to about 100% of A,
it contains from about 50% to about 100% of T,
it contains from 0% to about 10% of G, and
it contains from 0% to about 12% of C,
N9 being such that if d vary from 10 to 300, (N9)d represents a nucleic acid chain which is such that
it contains from about 50% to about 100% of A,
it contains from about 50% to about 100% of T,
it contains from 0% to about 10% of G, and
it contains from 0% to about 12% of C.
or any fragment of the above sequence consisting of at least 9 nucleotides.

The invention relates to the use of an isolated nucleic acid sequence, as a multi cellular DNA replication origin wherein said nucleic acid sequence consists of
a) the nucleic acid sequence 5'-(N$_7$)$_a$(N$_8$)$_b$(N$_3$GN$_4$)$_c$(N$_7$)$_d$(N$_8$)$_e$-3'   (SEQ ID NO: 2)

wherein N$_3$ is a T or a G base and N$_4$ is a G or a C,
wherein c vary from 3 to 20
wherein N$_7$ and N$_8$ represent any nucleotide,
wherein a and e independently from each other can be equal to 0, 1, 2 or 3, or vary from about 15 to 30, and
wherein b can be equal to 0, 1, 2 or 3 wherein d can be equal to 0, 1, 2 or 3 or vary from about 10 to 300,
b) or any fragment of the above sequence consisting of at least 9 nucleotides, said nucleic acid sequence being such that
it contains from 33% to 66% of G,
it contains from 27% to 33% of C,
it contains from 0% to 12% of A,
it contains from 0% to 15% of T,
it has a minimal consensus sequence 5'-N3GN4-3' wherein N3 is a T or a G base and N4 is a G or a C
said minimal consensus sequence being repeated from 3 to 20 times without interruption between said repeated minimal consensus sequence, for controlling the ex vivo replication of a nucleotidic sequence into a pluricellular eukaryotic cell. Advantageously, the invention relates to the use of the isolated nucleic acid sequence according to the above definition, wherein said nucleic acid sequence consists of one of the following sequences:

| | |
|---|---|
| AGCTGGGCGGCA | (SEQ ID NO: 24) |
| CAGCTGGGCGGC, and | (SEQ ID NO: 25) |
| GCTGGGCGGCAG. | (SEQ ID NO: 26) |

The above sequences that correspond to DNA eukaryotic origins are novel.

The invention relates to the isolated nucleic acid sequence according to claim 10, wherein said nucleic acid sequence being such that
it contains from about 33% to about 66% of G,
it contains from about 27% to about 33% of C,
it contains from about 0% to about 12% of A,
it contains from about 0% to about 15% of T, and
it has a minimal consensus sequence chosen among the following consensus sequences:
5'-N$_1$N$_2$G-3'
wherein N$_1$ is a G or a A and N$_2$ is a pyridine or a A
5'-N$_3$GN$_4$-3'
wherein N$_3$ is a T or a G base and N$_4$ is a G or a C, and
5'-GN$_5$N$_6$-3'
wherein N$_5$ is different from N$_6$, Ns is a G or a C and N$_6$ is a T or a A
said minimal consensus sequence being repeated from 3 to 20 times without interruption between said repeated minimal consensus sequence.

In one advantageous embodiment, the invention relates to the isolated nucleic acid sequence as defined above, wherein said nucleic acid sequence consists of the following sequence SEQ ID NO: 4:

5'-SHGCYGSYGGMGCYGSHGSTG-3', or any fragment of said nucleic acid sequence consisting of at least 9 nucleotides.

In one advantageous embodiment, the invention relates to the isolated nucleic acid sequence as defined above, wherein said nucleic acid sequence consists of the following sequence SEQ ID NO: 5:

5'-CKGYKGCKGCDGCKGCDGYKG-3' or any fragment of said nucleic acid sequence consisting of at least 9 nucleotides.

In one advantageous embodiment, the invention relates to the isolated nucleic acid sequence as defined above, wherein said nucleic acid sequence consists of one of the following sequences

| | |
|---|---|
| GTCCCAGTCCCAG | (SEQ ID NO: 6) |
| TGCTGCTGCTGCT | (SEQ ID NO: 7) |
| TATATATATATAT | (SEQ ID NO: 8) |
| AGCAGCAGCAGCA | (SEQ ID NO: 9) |
| GTTGCTGCTGCTG | (SEQ ID NO: 10) |
| TCAGACATCTTAG | (SEQ ID NO: 11) |
| AGCAGCAGCAACA | (SEQ ID NO: 12) |
| CAGACATCTTAGG | (SEQ ID NO: 13) |
| AGACATCTTAGGC | (SEQ ID NO: 14) |
| CAGCAGCAGCAGC | (SEQ ID NO: 15) |

-continued

| | |
|---|---|
| TAACGTGTGGTGA | (SEQ ID NO: 16) |
| TGTTGCTGCTGCT | (SEQ ID NO: 17) |
| CAGCAGCAGCAAC | (SEQ ID NO: 18) |
| TGCTGCTGC | (SEQ ID NO: 19) |
| CAGCAGCAG | (SEQ ID NO: 20) |
| CTGCTGCTG | (SEQ ID NO: 21) |
| CTCTCTCTCTCT | (SEQ ID NO: 22) |
| TCTCTCTCTC | (SEQ ID NO: 23) |
| AGCTGGGCGGCA | (SEQ ID NO: 24) |
| CAGCTGGGCGGC | (SEQ ID NO: 25) |
| GCTGGGCGGCAG | (SEQ ID NO: 26) |
| AGCAGCTGGACAC | (SEQ ID NO: 27) |
| CAGCAGCTGGACA | (SEQ ID NO: 28) |
| GCAGCAGCTGGAC | (SEQ ID NO: 29) |
| CAGCTGGACACAC | (SEQ ID NO: 30) |
| AGCAGACTGGGCG | (SEQ ID NO: 31) |

The invention also relates to a recombinant vector comprising at least one isolated nucleic acid sequence as defined above.

The above vector contains at least one origin of replication that replicates as the endogenous chromosomal DNA replication origins. Therefore, the vector is duplicated as an "endogenous chromosome". The Inventors have shown that this replication is effective (the above origins are active).

The invention also relates to a method, preferably in vitro, for controlling the replication of a nucleotidic sequence into a pluricellular eukaryotic cell, including mammal cells, comprising the insertion of, into said nucleotidic sequence, a nucleic acid sequence as defined above.

In one advantageous embodiment, the invention relates to the method as defined above, comprising a step of introducing said nucleotidic sequence into a pluricellular eukaryotic cell.

In one advantageous embodiment, the invention relates to the method as defined above for treating pathologies involving a deregulation of DNA replication, said method comprising the administration to an individual in a need thereof of a pharmaceutically effective amount of a nucleic acid sequence as defined above.

In one advantageous embodiment, the invention relates to the use of a nucleic acid sequence as defined above, for the preparation of a drug intended for the treatment of pathologies involving a deregulation of DNA replication.

In one advantageous embodiment, the invention relates to a nucleic acid sequence as defined above, for its use for the treatment of pathologies involving a deregulation of DNA replication.

The invention also relates to a pharmaceutical composition comprising, in particular as active substance, a nucleic acid sequence as defined above, in association with a pharmaceutically acceptable carrier.

The invention also relates to a method for initiating the replication of a deoxyribonucleic acid molecule in a pluricellular eukaryotic cell or in an eukaryotic cell extract, said method comprising a step of inserting, into said deoxyribonucleic acid molecule, at least one nucleic acid molecule representing a multicellular DNA replication origin, the replication origin comprising a at least nine nucleotides sequence, the at least nine nucleotides sequence consisting of at least three uninterrupted origin repeating elements (ORE) having the sequence $N_3GN_4$, wherein $N_3$ is T or G and $N_4$ is G or C.

In the invention, "initiating the replication of a deoxyribonucleic acid molecule" means that all steps necessary for replicating a double strand DNA molecule are carried out.

Also, in the invention, the ORE, repeated at least 3 times constitute the core of the DNA replication origin of multicellular eukaryotic cells.

Advantageously, the invention relates to the method above-mentioned, wherein the replication origin comprises one of the following sequences:

TGCTGCTGC, TGCTGGTGC, TGCGGCTGC, TGCGGGTGC,
TGCTGCTGG, TGCTGGTGG, TGCGGCTGG, TGCGGGTGG,
TGCTGCGGC, TGCTGGGGC, TGCGGCGGC, TGCGGGGGC,
TGCTGCGGG, TGCTGGGGG, TGCGGCGGG, TGCGGGGGG,
TGGTGCTGC, TGGTGGTGC, TGGGGCTGC, TGGGGGTGC,
TGGTGCTGG, TGGTGGTGG, TGGGGCTGG, TGGGGGTGG,
TGGTGCGGC, TGGTGGGGC, TGGGGCGGC, TGGGGGGGC,
TGGTGCGGG, TGGTGGGGG, TGGGGCGGG, TGGGGGGGG,
GGCTGCTGC, GGCTGGTGC, GGCGGCTGC, GGCGGGTGC,
GGCTGCTGG, GGCTGGTGG, GGCGGCTGG, GGCGGGTGG,
GGCTGCGGC, GGCTGGGGC, GGCGGCGGC, GGCGGGGGC,
GGCTGCGGG, GGCTGGGGG, GGCGGCGGG, GGCGGGGGG,
GGGTGCTGC, GGGTGGTGC, GGGGGCTGC, GGGGGGTGC,
GGGTGCTGG, GGGTGGTGG, GGGGGCTGG, GGGGGGTGG,
GGGTGCGGC, GGGTGGGGC, GGGGGCGGC, GGGGGGGGC,
GGGTGCGGG, GGGTGGGGG, GGGGGCGGG and GGGGGGGG.

Advantageously, the invention relates to the method above mentioned, wherein the ratio G/C in the replication origin is greater than 1.

The inventors have shown that a better efficiency is obtained when the replication origin is able to form a ternary structure that form a G-quadruplex.

In molecular biology, G-quadruplexes (also known as G-tetrads or G4-DNA) are nucleic acid sequences that are rich in guanine and are capable of forming a four-stranded structure. Four guanine bases can associate through Hoogsteen hydrogen bonding to form a square planar structure called a guanine tetrad, and two or more guanine tetrads can stack on top of each other to form a G-quadruplex. The quadruplex structure is further stabilized by the presence of a cation.

In one advantageous embodiment, the invention relates to the method according to the above definition, wherein the replication origin comprises one of the following sequences:

| | |
|---|---|
| agctggggcggca, | (SEQ ID NO: 24) |
| cagctggggcggc, | (SEQ ID NO: 25) |

-continued and gctggggcggcag. (SEQ ID NO: 26)

In one another advantageous embodiment, the invention relates to the above mentioned method, wherein the replication origin comprises one of the following sequences:

GGGGGCGGGGAGGGAAGGGGG, (SEQ ID NO: 32)

which is the replication origin of the mouse cc4 gene and

GGGGGATGGGGTTGGAATGGGGCGGG, (SEQ ID NO: 33)

which is the replication origin of the mouse cc2 gene.

The invention also relates to a method for conferring autonomous replicative properties to a non self-replicating deoxyribonucleic acid molecule in a pluricellular eukaryotic cell or cell extract, said method comprising a step of inserting, into said deoxyribonucleic acid molecule, at least one nucleic acid molecule representing a multicellular DNA replication origin, the replication origin comprising at least nine nucleotides sequence, the at least nine nucleotides sequence consisting of at least three uninterrupted origin repeating elements (ORE) having the sequence $N_3GN_4$, wherein $N_3$ is T or G and $N_4$ is G or C.

Advantageously, the invention relates to the method above mentioned, wherein the ratio G/C in the replication origin is greater than 1.

Advantageously, the invention relates to the method above mentioned, wherein the replication origin comprises one of the following sequences:

TGCTGCTGC, TGCTGGTGC, TGCGGCTGC, TGCGGGTGC,
TGCTGCTGG, TGCTGGTGG, TGCGGCTGG, TGCGGGTGG,
TGCTGCGGC, TGCTGGGGC, TGCGGCGGC, TGCGGGGGC,
TGCTGCGGG, TGCTGGGGG, TGCGGCGGG, TGCGGGGGG,
TGGTGCTGC, TGGTGGTGC, TGGGGCTGC, TGGGGGTGC,
TGGTGCTGG, TGGTGGTGG, TGGGGCTGG, TGGGGGTGG,
TGGTGCGGC, TGGTGGGGC, TGGGGCGGC, TGGGGGGGC,
TGGTGCGGG, TGGTGGGGG, TGGGGCGGG, TGGGGGGGG,
GGCTGCTGC, GGCTGGTGC, GGCGGCTGC, GGCGGGTGC,
GGCTGCTGG, GGCTGGTGG, GGCGGCTGG, GGCGGGTGG,
GGCTGCGGC, GGCTGGGGC, GGCGGCGGC, GGCGGGGGC,
GGCTGCGGG, GGCTGGGGG, GGCGGCGGG, GGCGGGGGG,
GGGTGCTGC, GGGTGGTGC, GGGGGCTGC, GGGGGGTGC,
GGGTGCTGG, GGGTGGTGG, GGGGGCTGG, GGGGGGTGG,
GGGTGCGGC, GGGTGGGGC, GGGGGCGGC, GGGGGGGGC,
GGGTGCGGG, GGGTGGGGG, GGGGGCGGG and GGGGGGGG.

Advantageously, the invention relates to the method above mentioned, wherein the replication origin comprises one of the following sequences:

agctggggcggca, (SEQ ID NO: 24)

cagctggggcggc, (SEQ ID NO: 25)

and gctggggcggcag., (SEQ ID NO: 26)

wherein the replication origin comprises one of the following sequences:

GGGGGCGGGGAGGGAAGGGGG, (SEQ ID NO: 32)

and

GGGGGATGGGGTTGGAATGGGGCGGG. (SEQ ID NO: 33)

The invention also relates to a process for preparing a recombinant non naturally occurring DNA vector comprising as the unique means for replicating DNA at least one multicellular DNA replication origin, said process comprising a step of inserting into a vector at least one nucleic acid molecule representing a multicellular DNA replication origin, the replication origin comprising at a least nine nucleotides sequence, the at least nine nucleotides sequence consisting of at least three uninterrupted origin repeating elements (ORE) having the sequence $N_3GN_4$, wherein $N_3$ is T or G and $N_4$ is G or C, wherein the replication origin is originated from a nucleic acid molecule, the nucleic acid molecule being absent in the vector before its insertion.

By "recombinant non naturally occurring DNA vector" it is meant in the invention a vector that does not exist without man intervention.

In other words, the vectors encompassed by the invention are artificially constructed by biologists. Vectors such as artificial chromosomes (of mouse for instance) are not encompassed by the invention.

Vectors of the invention are commonly constituted by a backbone from prokaryotic or yeast vectors (such as pBR322 vector, yeast artificial chromosomes) in which has been introduced at least one replication origin according to the invention.

The invention also relates to a map referencing all the DNA replication organisms of multicellular eukaryotic cells, said map being obtainable by the process as defined above. The invention also relates to a map referencing all the DNA replication origins of multicellular eukaryotic totipotent cells, said map being obtainable by the process as defined above.

The invention also relates to a map referencing all the DNA replication origins activated in multicellular eukaryotic differentiated cells, said map being obtainable by the process as defined above.

The invention also relates to a method for the diagnostic, preferably in vitro or ex vivo, of pathologies involving a deregulation of DNA replication in an individual, or in a biological sample from an individual, said method comprising the steps:

establishing the map referencing all DNA replication origins activated in multicellular eukaryotic differentiated cells of said individual, or of said biological sample from an individual, comparing the map obtained in the previous step with a reference map, said reference map corresponding to the map referencing all DNA replication origins activated in multicellular eukaryotic healthy differentiated cells of said individual or of said biological sample from an individual, concluding, from the previous comparison if said individual is afflicted by a pathology involving a deregulation of DNA replication The invention also relates to a method for the diagnostic, preferably in vitro or ex vivo, of the genetic modification of a cell of an individual, preferably a pluripotent cell, said method comprising the steps:

establishing the map referencing all DNA replication origins activated in a cell of an individual, comparing the map obtained in the previous step with a reference map, said reference map corresponding to the map referencing all DNA replication origins activated in an healthy cell of the same type than the cell used in the previous step, concluding, from the previous comparison said cell have a genetic modification (genetic variation of a cell during passages in vitro).

The invention also relates to a process for purifying nascent DNA, said process comprising a step of extracting a mixture of nucleic acid molecules, said mixture of nucleic acid molecules comprising DNA and hybrid RNA-DNA, from multi cellular eukaryotic cells a step of enrichment of hybrid RNA-DNA from said mixture by eliminating proteins associated with said nucleic acid molecules, and at least two step of elimination of DNA from the mixture to recover purified nascent DNA.

In one advantageous embodiment, the invention relates to the process as defined above, for purifying nascent DNA allowing the localisation and the numbering of the active DNA replication origins of multi cellular eukaryotic cells, said process comprising the steps:

Harvesting and lysing dividing cells to obtain DNA,
Digesting proteins anchored in DNA,
Washing DNA in ethanol,
Purifying nascent DNA in a single neutral 5 to 30% sucrose gradient,
Collecting fractions corresponding to DNA from about 0.5-1 kb, about 1-1.5 kb, about 1 0.5-2 kb and about 2-3 kb,
Phosphorylating extremity of DNA and digesting contaminant double strand DNA
Repeating at least once the previous step
Precipitating nascent DNA and purifying said nascent DNA (for instance with Cyscibe-GFX kit)
Amplifying nascent DNA (for instance WGA-Sigma kit),
Purifying amplicons, said amplicons being the products of the amplification of said nacent DNA obtained in the previous step,
Locating on whole genome nascent DNA (by DNA hybridization on WCA chip or by systematic DNA sequence of amplified DNA) to determine active replication origins, and numbering said active replication origins.

In one advantageous embodiment, the invention relates to the process as defined above, for purifying nascent DNA allowing the localisation and the numbering of all the DNA replication origins of multi cellular eukaryotic cells, said process being carried out in totipotent cells, wherein all the replication origins are actives.

LEGEND TO THE FIGURES

FIGS. 1A-I represent the association between genes and replication origins

FIG. IA corresponds to a schematic representation of a gene, in which Tss (transcription initiation site), exon and intron are represented.

FIG. 1B represents an example of the distribution of replication origins found on a 200 kb region of MEF cells and ES cells. Negative controls for the mouse cells are the P19 asynchronous cells or PI9 arrested in late mitosis by nocodazol.

FIG. IC represents an example of the distribution of replication origins found on a 200 kb region of Kc cells. Negative control for Kc cells come from fragmented total DNA of mitotic cells and then treated by lambda exonuclease.

FIG. ID represents a pie chart showing the percentage of origin sequences in genes sequences (light grey) and intergenic sequences (dark grey) in MEF cells. The value of gene association for randomized origins is indicated by the dashed pie (53%). Similar values were obtained for ES and P19 cells. (*:p<0.001)

FIG. IE represents a graph showing the percentage of origin sequences in promotor sequences (white) and intronic sequences (light grey) and exonic sequences (dark grey) in MEF cells, ES cells and PI9 cells. (*:p<0.001)

FIG. IF represents a pie chart showing the percentage of origin sequences in genes sequences (light grey) and intergenic sequences (dark grey) in *drosophila* Kc cells. The value of gene association for randomized origins is indicated by the dashed pie (62%). (*:p<0.001)

FIG. 1G represents a graph showing the percentage of origin sequences in promotor sequences and intronic sequences and exonic sequences in *drosophila* Kc cells. The value of association for randomized origins is indicated by the dashed boxes. (*:p<0.001)

FIG. 1H represents a graph showing the association of replication origins with highly transcribed genes in MEF cells. The transcriptional output of gene associated (+) or not (−) with replication origins is indicated. The average transcription of genes associated with randomly distributed origins is also shown. (*:p<0.001)

FIG. 1I represents a graph showing the association of replication origins with highly transcribed genes in *drosophila* Kc cells. The transcriptional output of gene associated (+) or not (−) with replication origins is indicated. The average transcription of genes associated with randomly distributed origins is also shown. (*:p<0.001)

FIGS. 2A-K represent the association between CpG Islands and replication origins FIG. 2A represents the sum of all the Nascent Strands signals (corresponding to replication origins) around the site of initiation of transcription (TSS:Transcription Start Sites) in mouse MEF. Shown is the cumulative Nascent strand signal associated with all TSS (black line) and TSS associated with active replication origins (gray line).

Figure 2A:
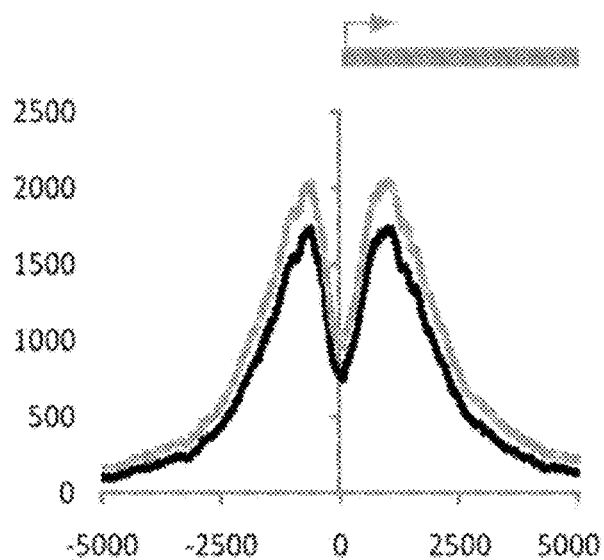
FIG. 2B represents the sum of all the Nascent Strands signals around TSS associated with CpG Islands (CGI, light grey line) or not associated (dark grey line) in mouse MEF.
FIG. 2C represents an example of the association of replication origins of MEF, ES and P19 cells with CpG Islands. Shown is the localization of genes, CpG islands and Nascent Strands signals.
FIG. 2D represents Venn diagram showing the strong association between replication origins and CpG Islands in mouse MEF. The percentage of association is indicated.
Figure 2B:
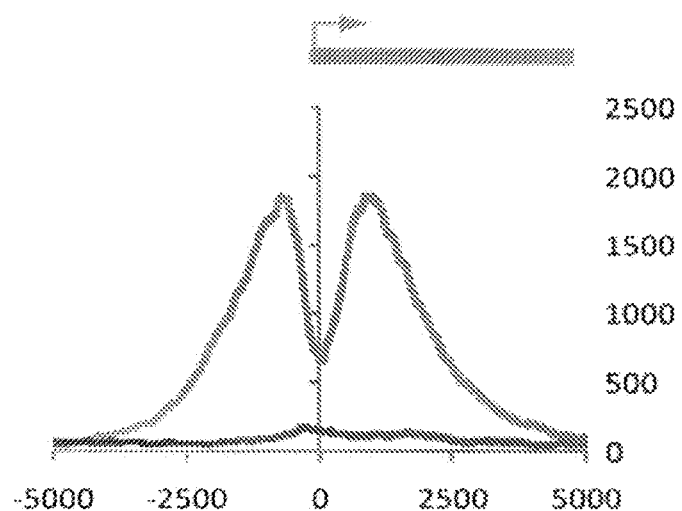
Figure 2C:
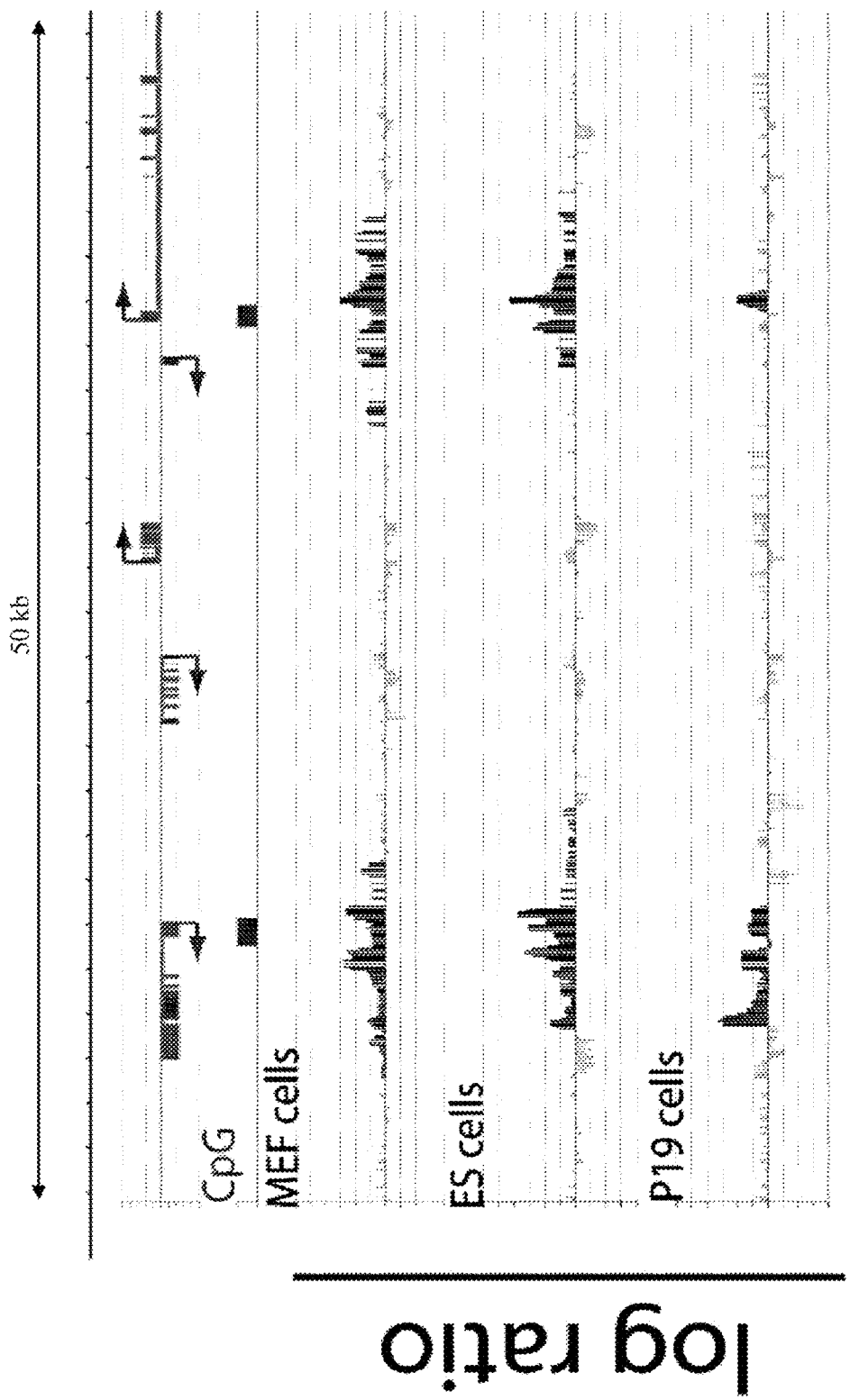
Figure 2D:
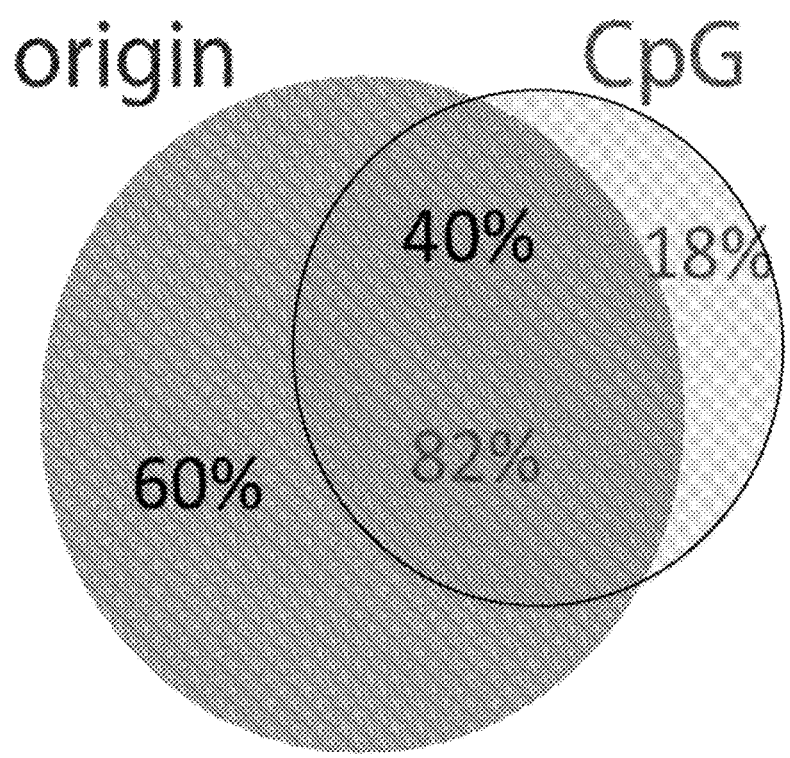
Figure 2E:
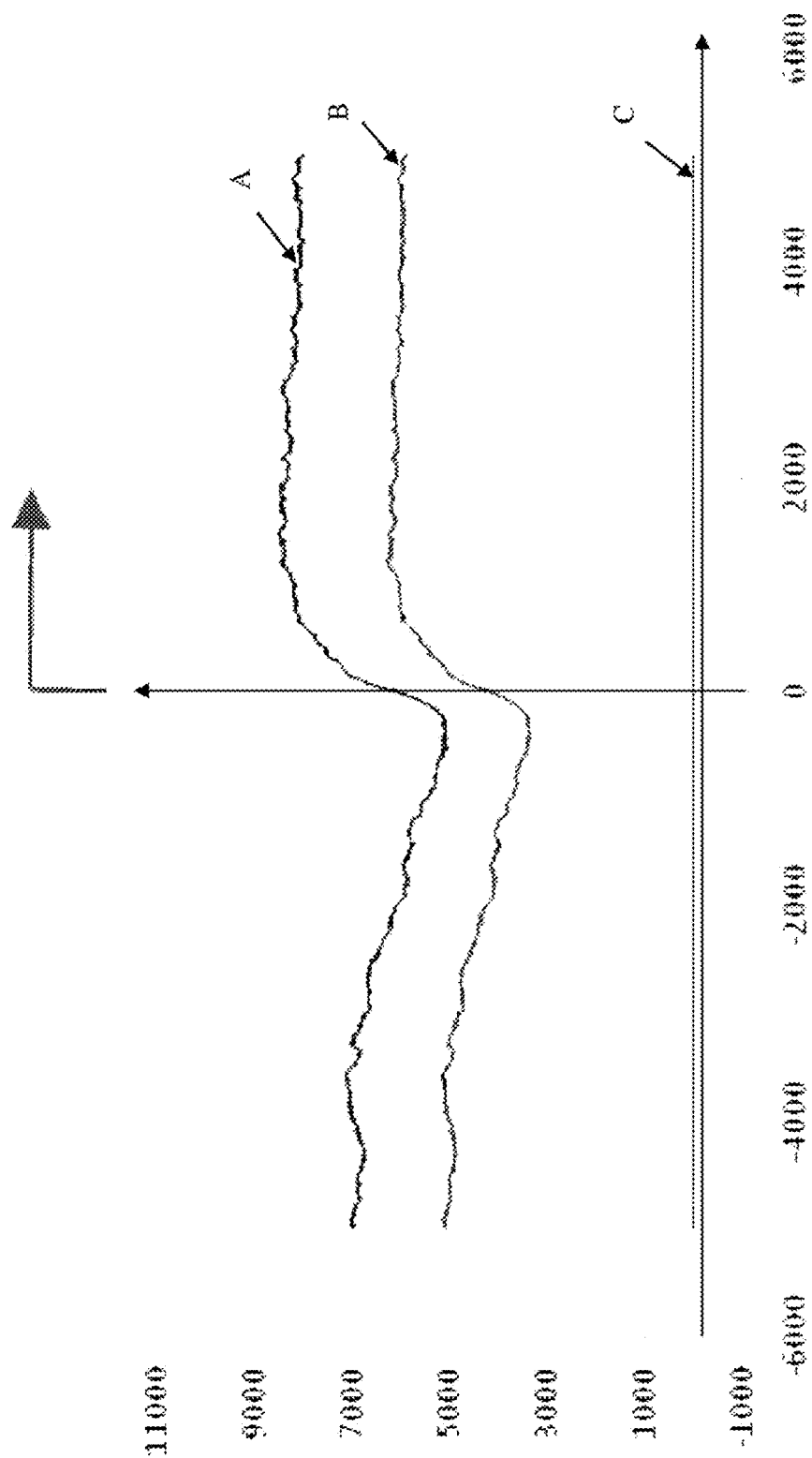

FIG. 2E represents the sum of all the Nascent Strands signals (corresponding to replication origins) around the site of initiation of transcription (TSS:Transcription Start Sites) in *drosophila* Kc cells. Shown is the cumulative Nascent strand signal associated with all TSS (line 'b') and of TSS associated with active replication origins (line 'a') in proliferating cells. The cumulative signal of all TSS of mitotic and non-proliferating Kc cells is also shown (line 'c').

Figure 2F:
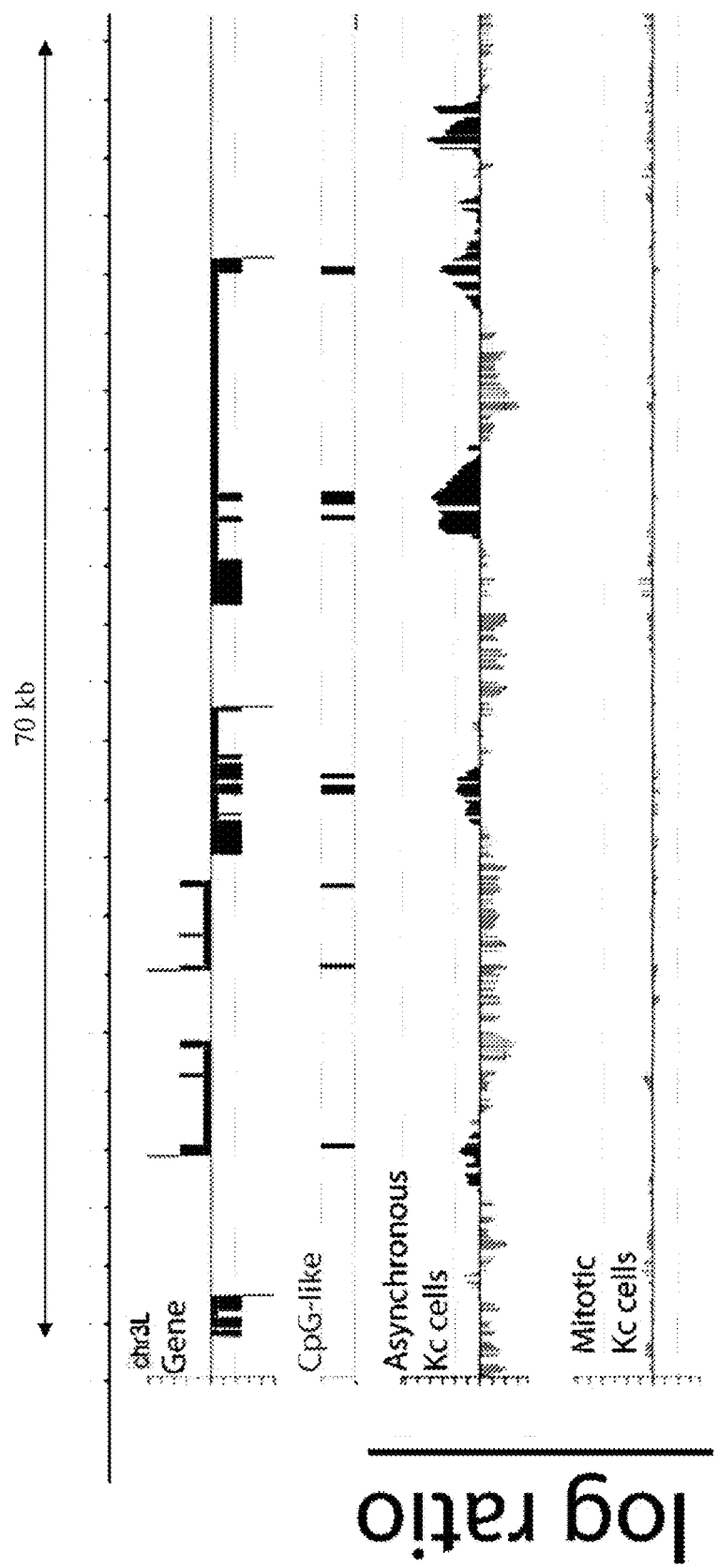

FIG. 2F represents an example of the association of replication origins of *drosophila* Kc cells with CpG Islands-like sequences. Shown is the localisation of genes, CpG islands and Nascent Strands signals in proliferating and mitotic cells.

Figure 2G:
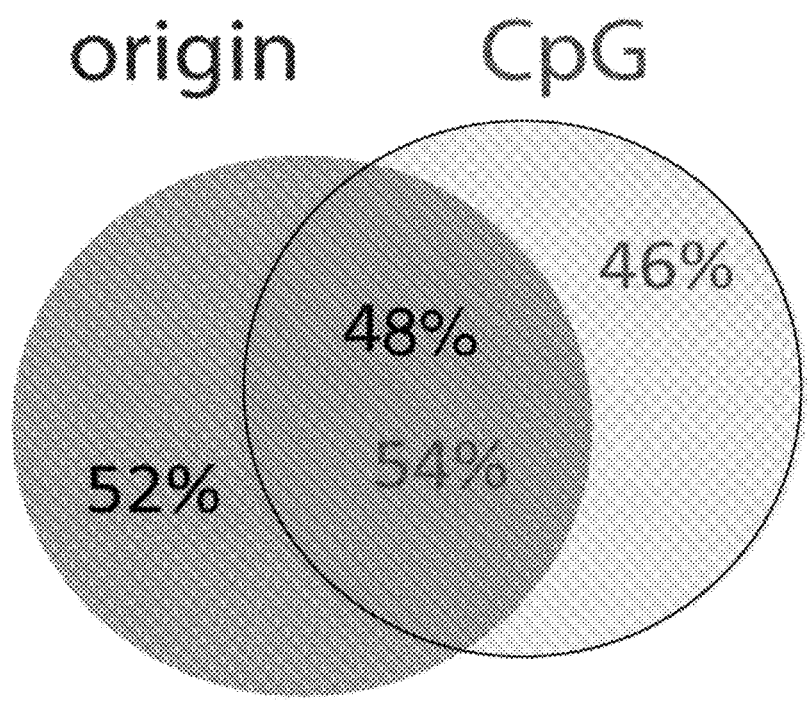

FIG. 2G represents Venn diagram showing the strong association between replication origins and CpG Islands in *drosophila* Kc cells. The percentage of association is indicated.

Figure 2H:
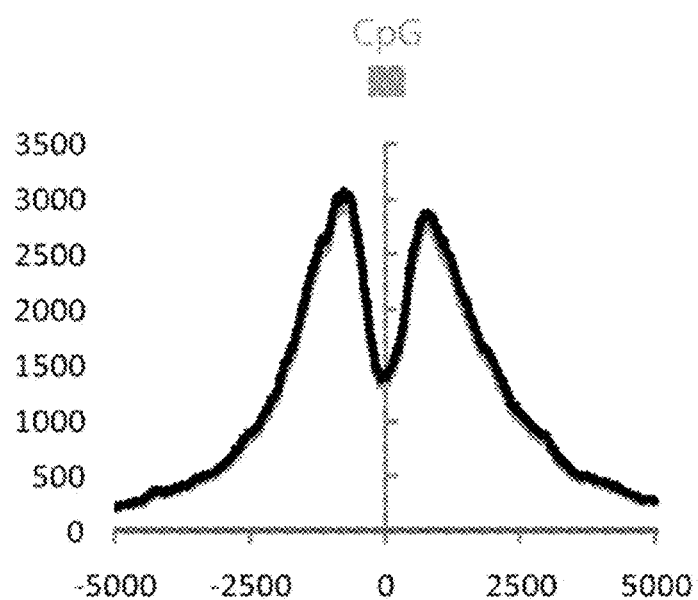

FIG. 2H represents the sum of all the Nascent Strands signals (corresponding to replication origins) around the CpG Islands in mouse MEF. Shown is the cumulative Nascent strand signal of all CpG Islands (grey line) and CpG Islands associated with active replication origins (black line).

Figure 2I:
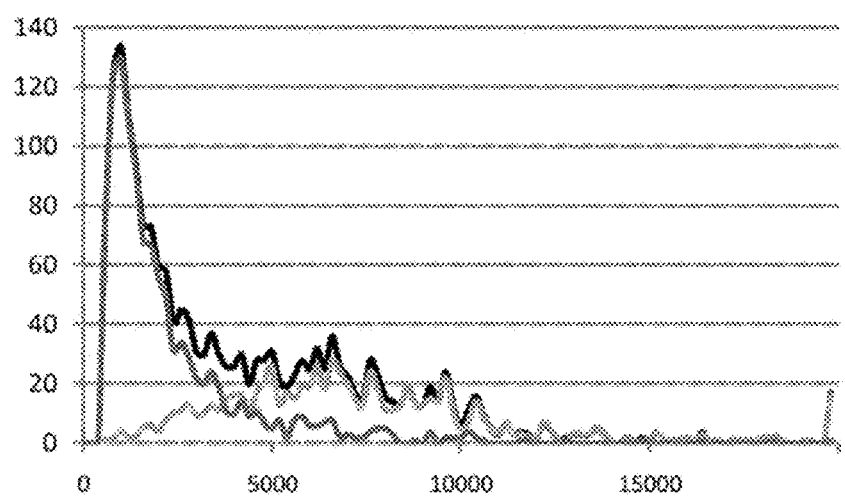

FIG. 2I represents the size of replication origins with regard to their association with CpG islands. The lines show the frequency of finding a replication origin of a particular length. All origins (black line) and origins associated (light grey) with CpG islands or not (dark grey line) in MEF are illustrated.

Figure 2J:
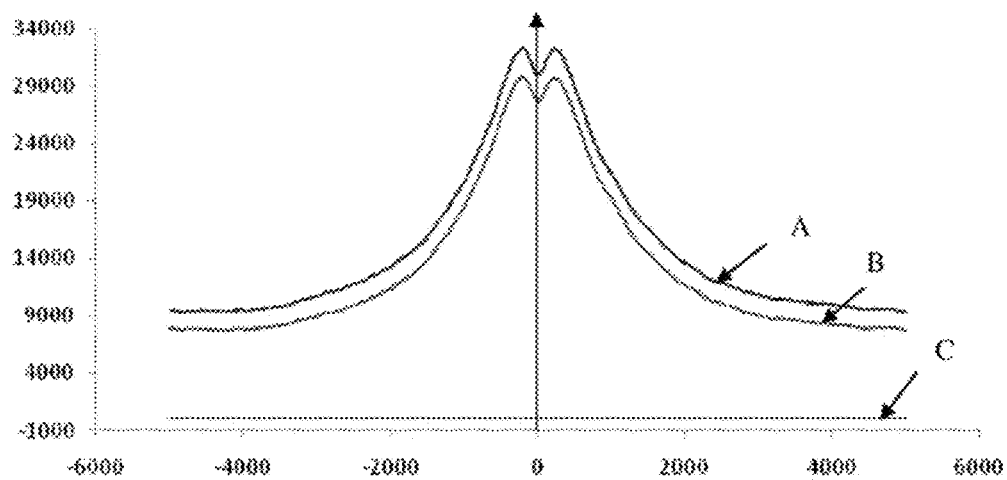

FIG. 2J represents the sum of all the Nascent Strands signals (corresponding to replication origins) around the CpG Islands-like sequences in mouse MEF. Shown is the cumulative Nascent strand signal of all CpG Islands (line 'b') and of CpG Islands associated with active replication origins (line 'a') in proliferating cells. The cumulative signal of all CpG Islands of mitotic and non-proliferating Kc cells is also shown (line 'c').

Figure 2K:
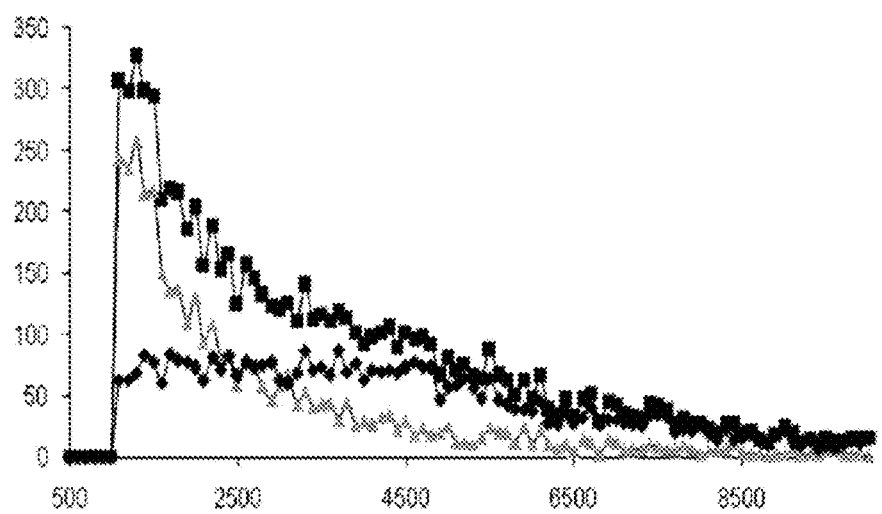

FIG. 2K represents the size of replication origins with regard to their association with CpG islands. The lines show the frequency of finding a replication origin of a particular length. All origins ('square' line) and origins associated ('diamond' line) with CpG islands or not ('triangle' line) in Kc cells are illustrated.

FIGS. 3A-G represent the common conserved motif in Metazoan replication origins.

Figure 3A:
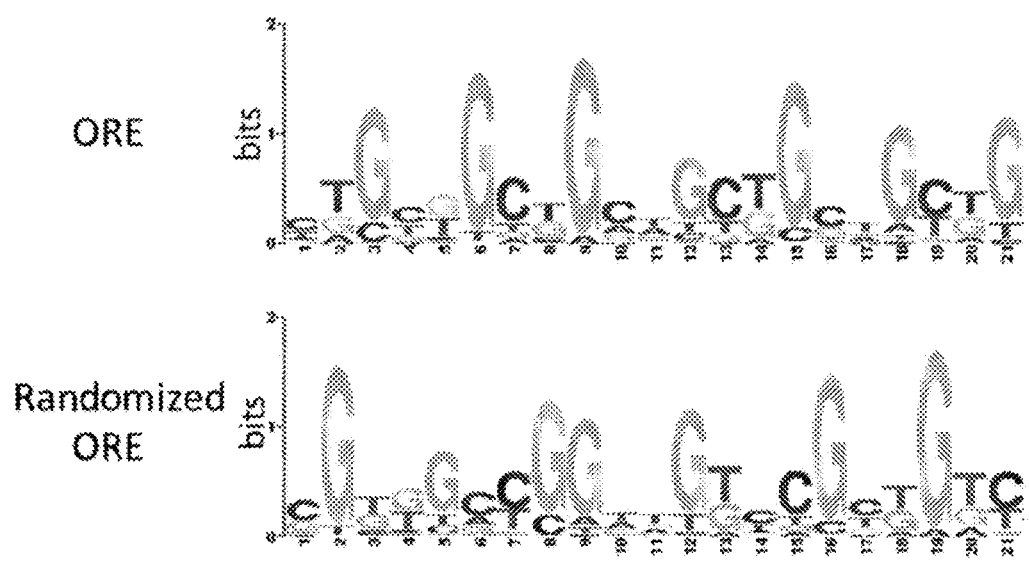

FIG. 3A illustrates the consensus element found in metazoan replication origins. The 'ORE' (for Origin Repeated Element) motif was generated using MEME server with *drosophila* origins. Also shown is a randomized motif to evaluate the specificity of the ORE. The size of letter represents the base preference for every position of the motif.

Figure 3B:
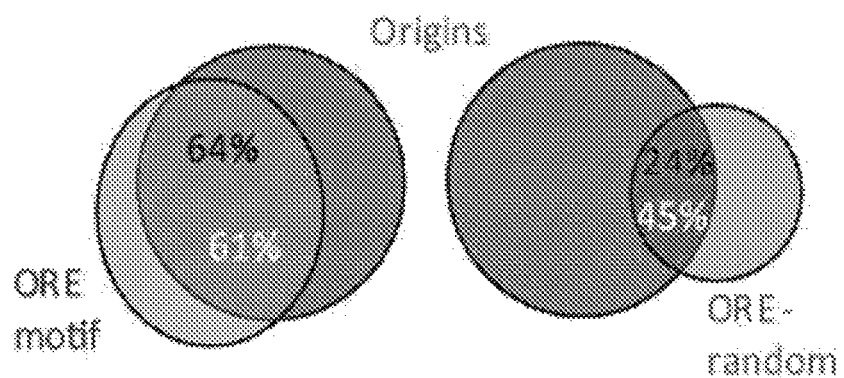

FIG. 3B represents Venn diagram showing the strong association between replication origins and occurrences of the ORE in *drosophila* cells. The much weaker overlap between origins and the randomized motif is shown. The percentage of association is indicated.

Figure 3C:
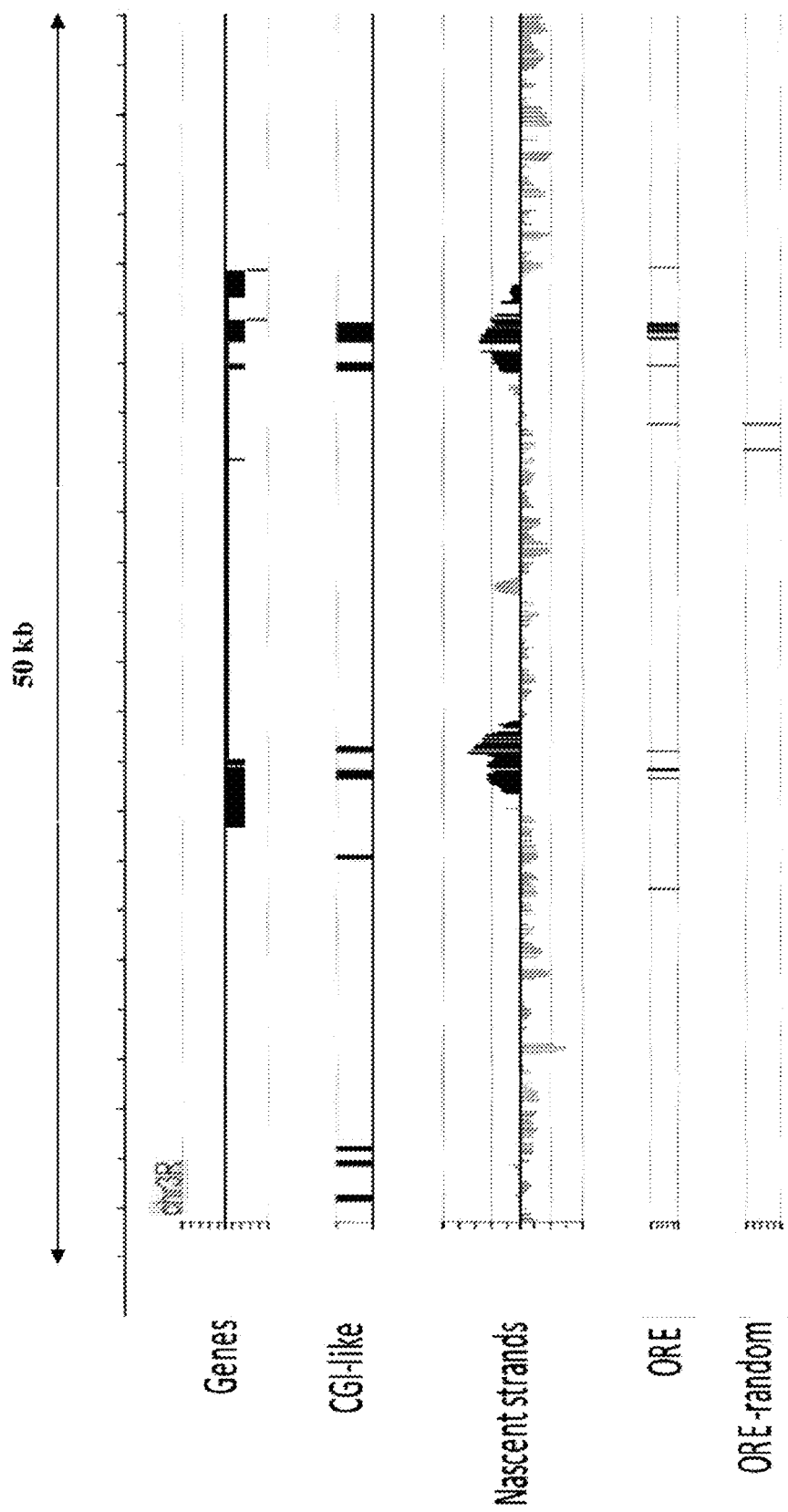

FIG. 3C represents an example of the association of replication origins of Kc cells with occurrences of the ORE. Shown is the localization of genes, CpG islands-like sequences, Nascent Strands signals and occurrences of ORE and randomized ORE.

Figure 3D:
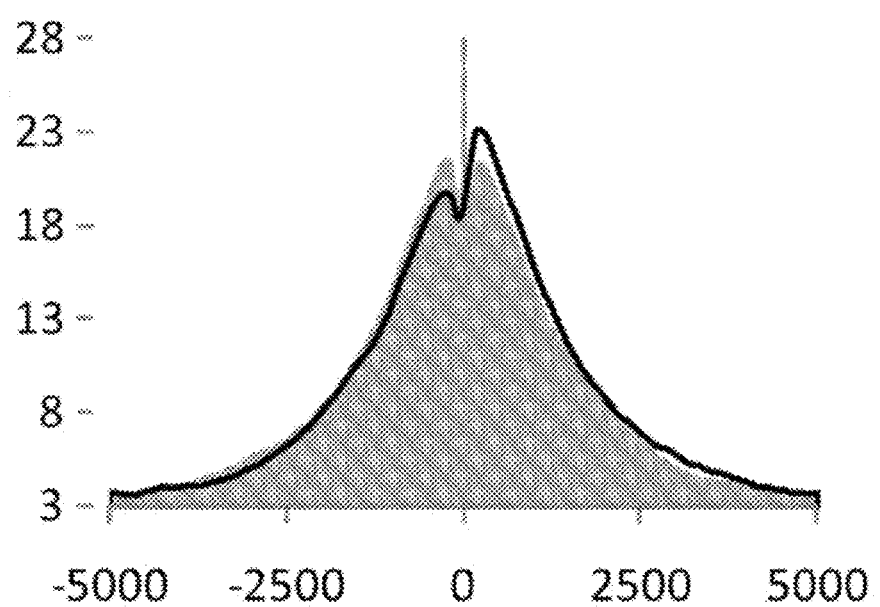

FIG. 3D represents the sum of all the Nascent Strands signals (corresponding to replication origins) around occurrences of the ORE in *drosophila* Kc cells. Shown is the cumulative Nascent strand signal associated with non-orientated motif (grey shadow) or with oriented ORE (black line). The x-axis represents the distance (in base pair) from ORE occurrences. The y-axis corresponds to cumulative p-value.

Figure 3E:
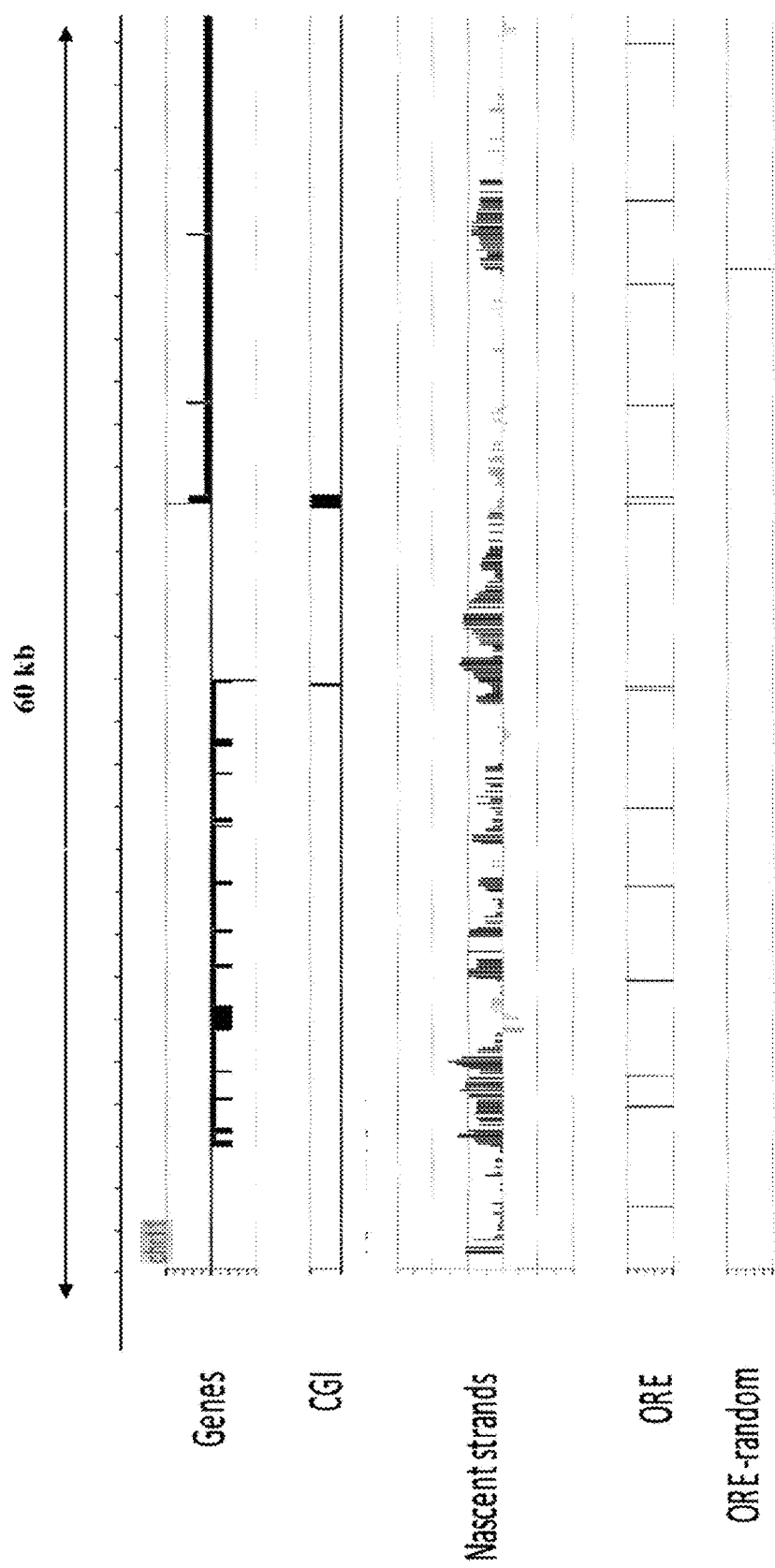

FIG. 3E represents an example of the association of replication origins of P19 cells with occurrences of the ORE. Shown is the localization of genes, CpG islands, Nascent Strands signals and occurrences of ORE and randomized ORE.

Figure 3F:
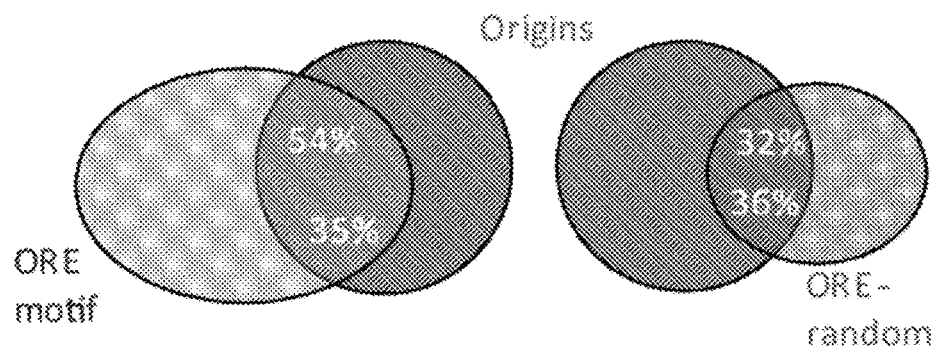

FIG. 3F represents Venn diagram showing the strong association between replication origins and occurrences of the ORE in mouse MEP cells. The much weaker overlap between origins and the randomized motif is shown. The percentage of association is indicated.

Figure 3G:
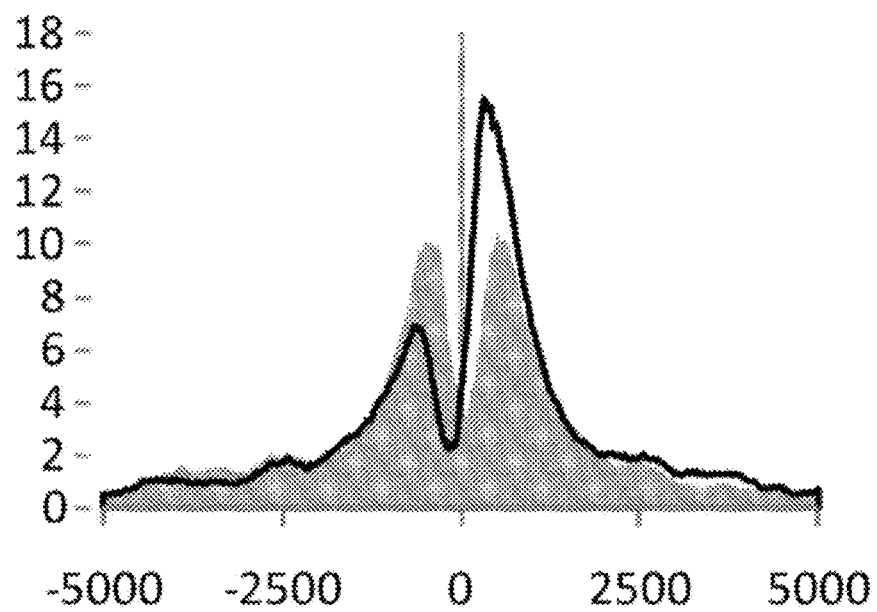

FIG. 3G represents the sum of all the Nascent Strands signals (corresponding to replication origins) around occurrences of the ORE in *drosophila* P19 cells. Shown is the cumulative Nascent strand signal associated with non-orientated motif (grey shadow) or with oriented ORE (black line). The x-axis represents the distance (in base pair) from ORE occurrences. The y-axis corresponds to cumulative p-value.

FIGS. 4A-L represent the grouping into functional clusters along the chromosome of Metazoan replication origins.

Figure 4A:
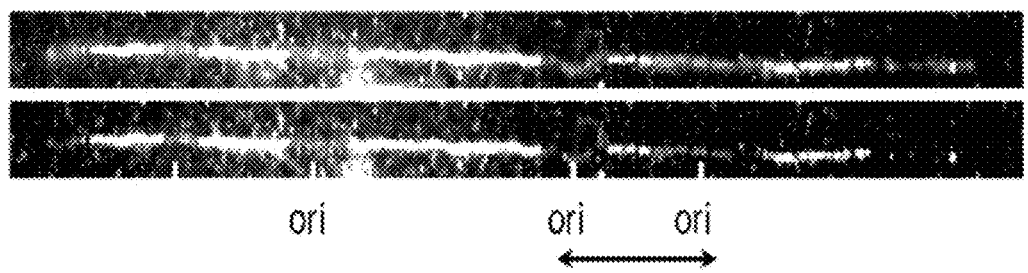

FIG. 4A shows an example of single-molecule analysis of the inter-origin spacing by molecular combing of DNA in Kc cells by two pulse labeling. The inferred position of replication origins is shown.

Figure 4B:
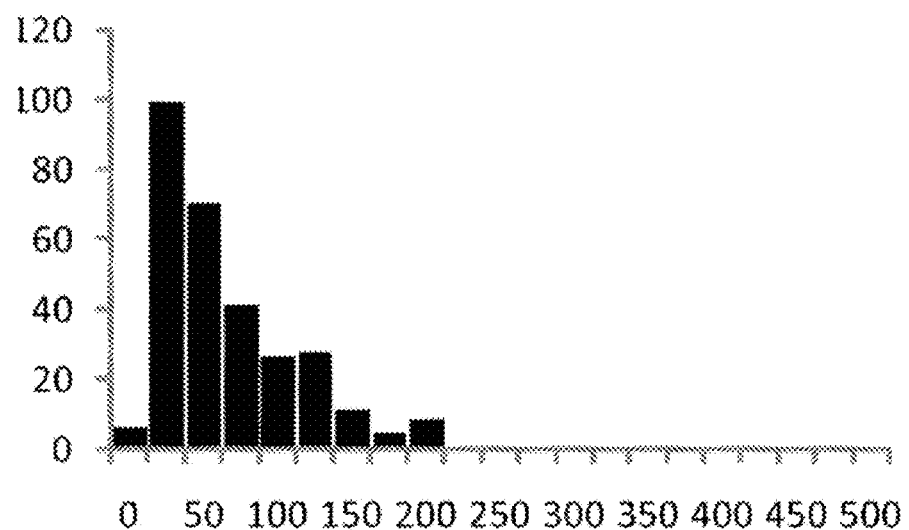

FIG. 4B illustrates the distribution of the inter-origin distances in Kc cells. The x-axis represents the inter-origin spacing in kb while the frequency in shown on the y-axis.

Figure 4C:
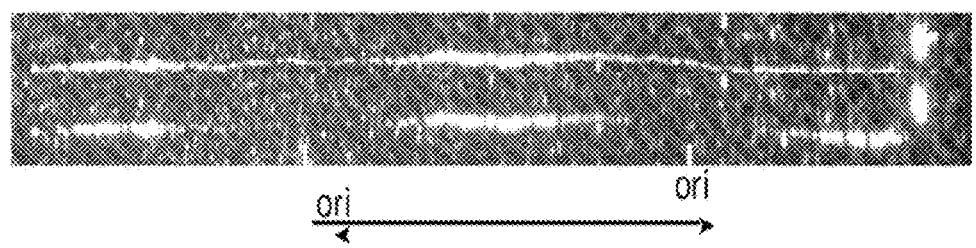

FIG. 4C shows an example of single-molecule analysis of the inter-origin spacing by molecular combing of DNA in MEF cells by two pulse labeling. Very similar results were obtained for ES cells.

Figure 4D:
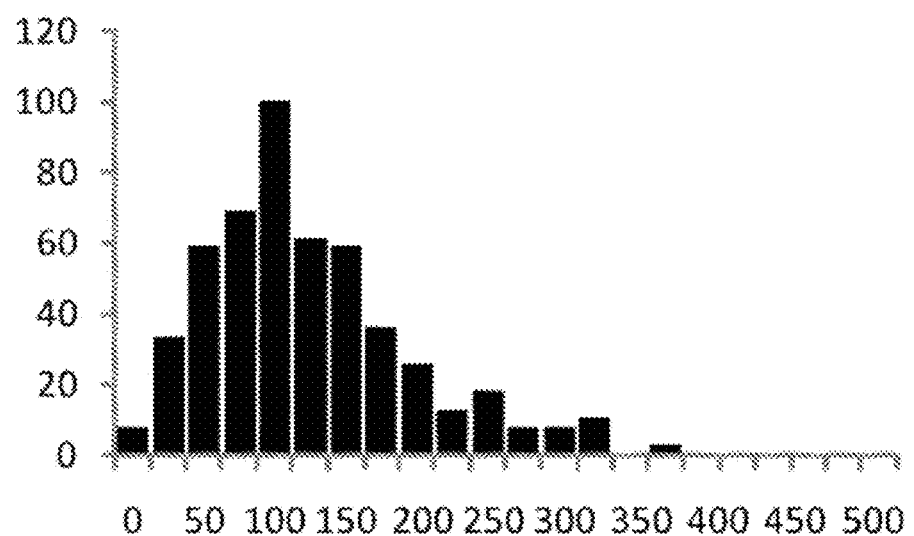

FIG. 4D illustrates the distribution of the inter-origin distances in MEF cells. The x-axis represents the inter-origin spacing in kb while the frequency in shown on the y-axis. Very similar results were obtained for ES cells.

Figure 4E:
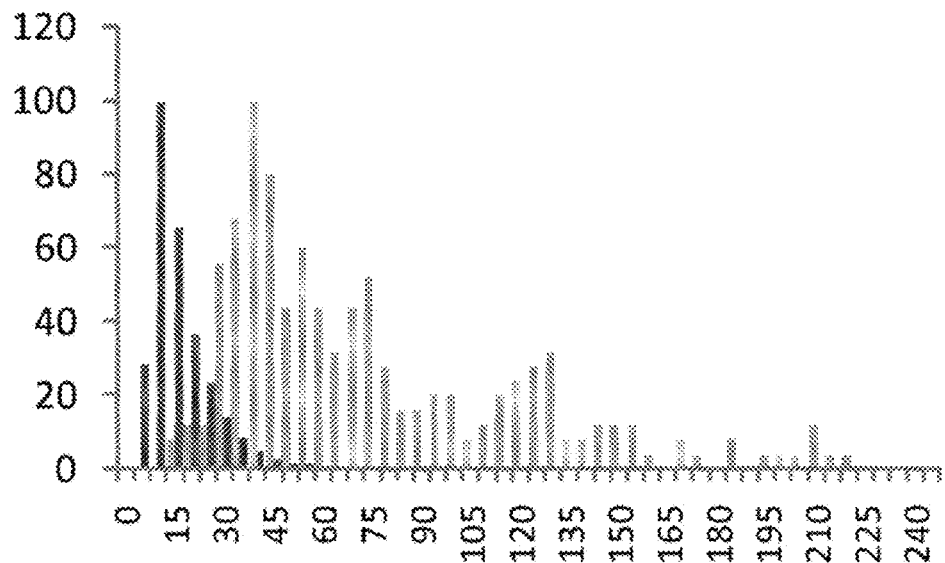

FIG. 4E illustrates the distribution of the inter-origin distances obtained from combing data (grey bars) and from micro-array analysis (blue bars) in Kc cells. The x-axis represents the inter-origin spacing in kb while the frequency in shown on the y-axis.

Figure 4F:
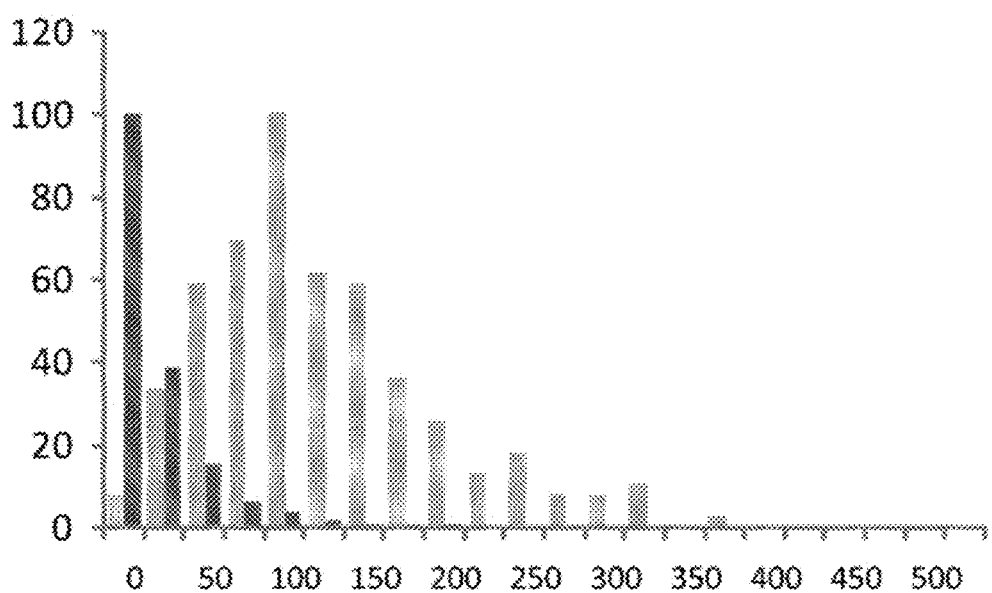

FIG. 4F illustrates the distribution of the inter-origin distances obtained from combing data (grey bars) and from micro-array analysis (blue bars) in MEF cells. The x-axis represents the inter-origin spacing in kb while the frequency in shown on the y-axis. Very similar results were obtained for ES cells.

Figure 4G:
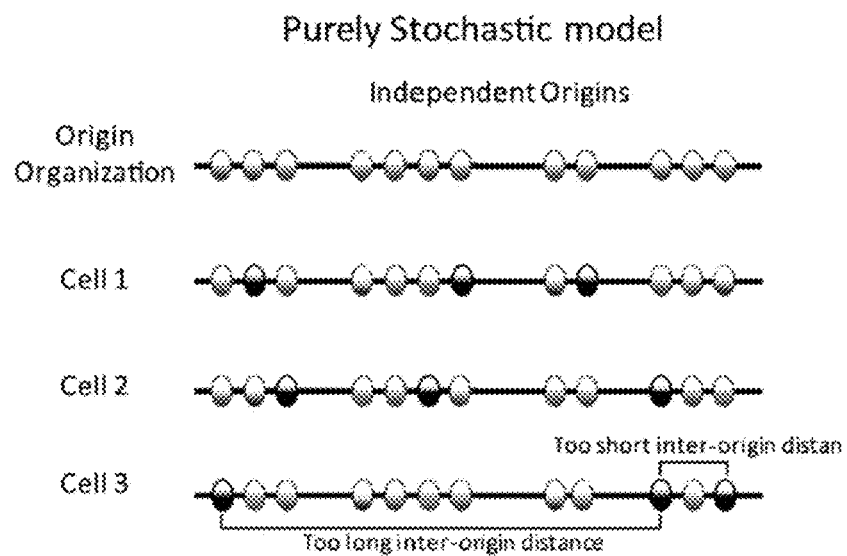

FIG. 4G illustrates the Purely Stochastic Model of Ori firing. In this model, Oris are completely independent and are activated randomly (red cercles). Very short and long inter-origin distances are observed.

Figure 4H:
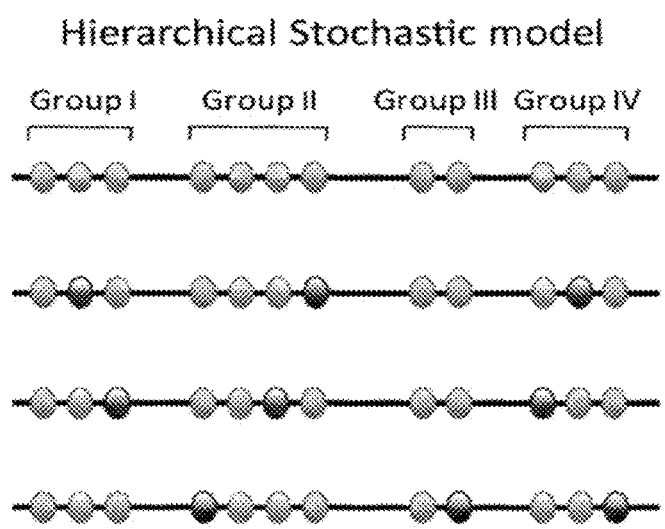

FIG. 4H illustrates the Hierarchical Stochastic Model. In this model, Oris are linked within functional units where activation of one Ori silences the others in the same group.

Figure 4I:
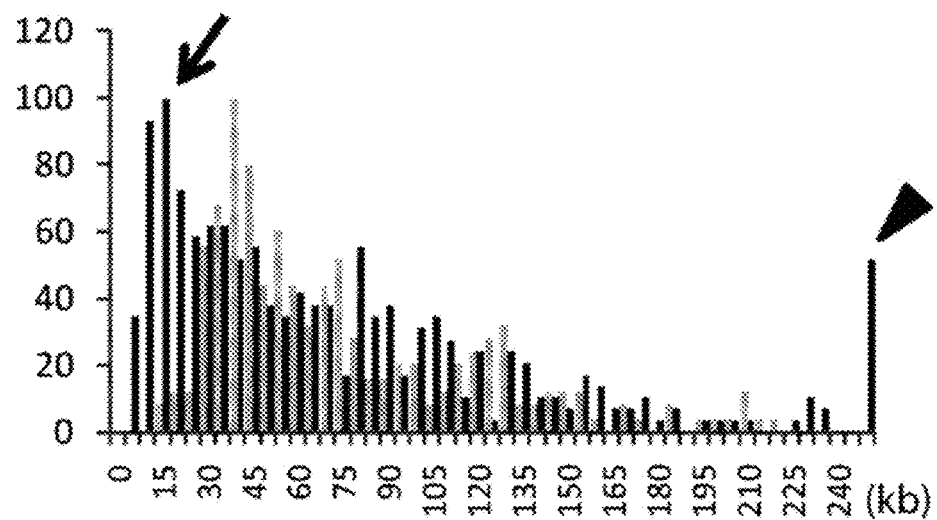

FIG. 4I shows the distribution of the inter-origin distances obtained from combing data of Kc cells (light grey bars) and from computational simulations (dark grey bars). In the tested model, replication origins were picked at random. Note the presence of short (arrow) and long (arrowhead) inter-origin distances in the simulated dataset not found in the combing analysis. The x-axis represents the inter-origin spacing in kb while the frequency in shown on the y-axis.

Figure 4J:
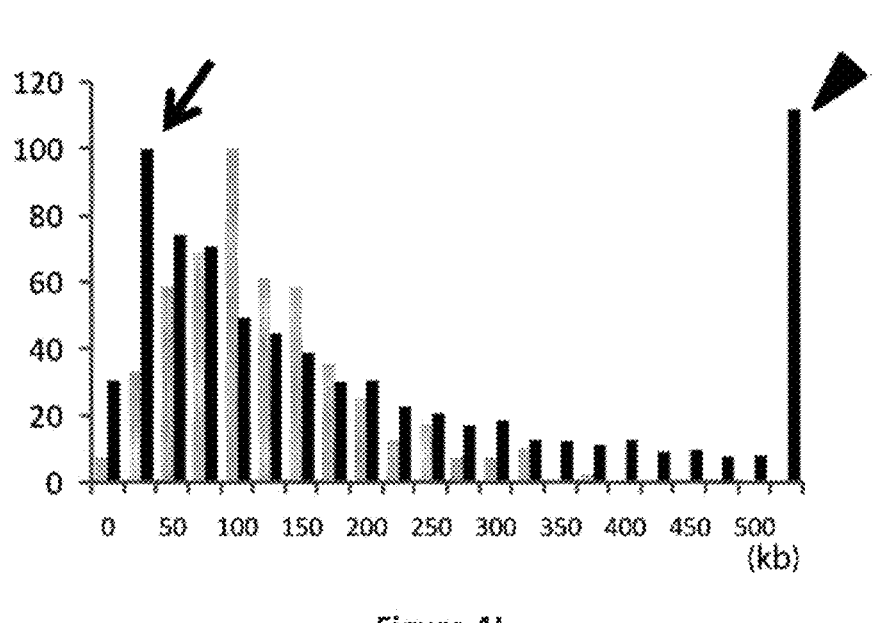

FIG. 4J shows the distribution of the inter-origin distances obtained from combing data of MEF cells (light grey bars) and from computational simulations (dark grey bars). In the tested model, replication origins were picked at random. Note the presence of short (arrow) and long (arrowhead) inter-origin distances in the simulated dataset not found in the combing analysis. The x-axis represents the inter-origin spacing in kb while the frequency in shown on the y-axis. Very similar results were obtained for ES cells.

Figure 4K:
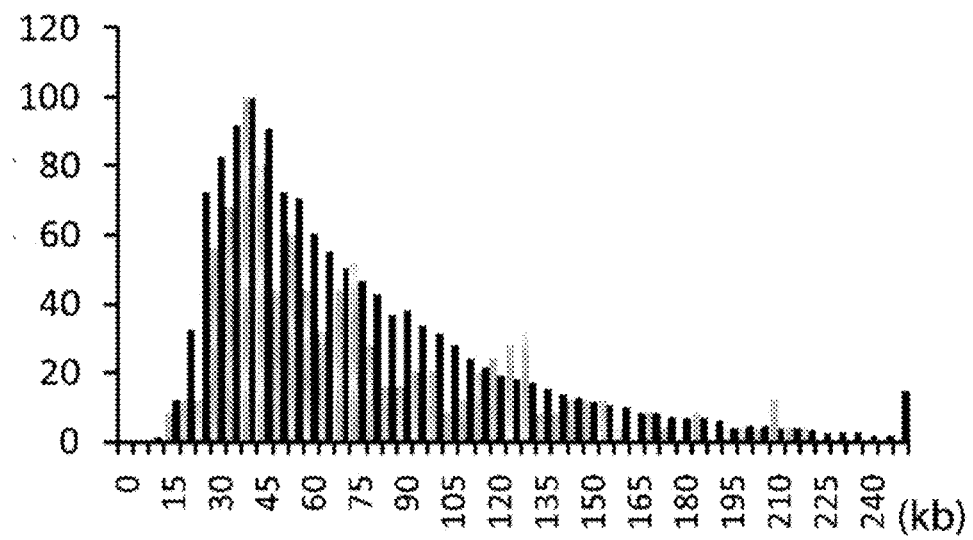

FIG. 4K shows the distribution of the inter-origin distances obtained from combing data of Kc cells (light grey bars) and from computational simulations (light grey bars). In the tested model, replication origins are clustered into functional groups where the firing of one randomly chosen replication origin suppresses the activation of the other origins within the same group. Both set of data correlate well. The x-axis represents the inter-origin spacing in kb while the frequency in shown on the y-axis.

Figure 4L:
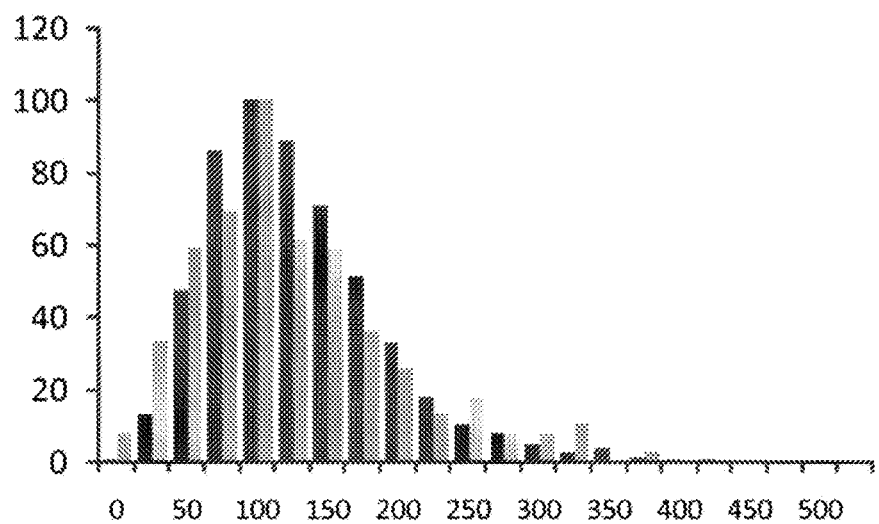

FIG. 4L shows the distribution of the inter-origin distances obtained from combing data of MEF cells (light grey bars) and from computational simulations (light grey bars). In the tested model, replication origins are clustered into functional groups where the firing of one randomly chosen replication origin suppresses the activation of the other origins within the same group. Both set of data correlate well. The x-axis represents the inter-origin spacing in kb while the frequency in shown on the y-axis. Very similar results were obtained for ES cells.

Figure 5A:
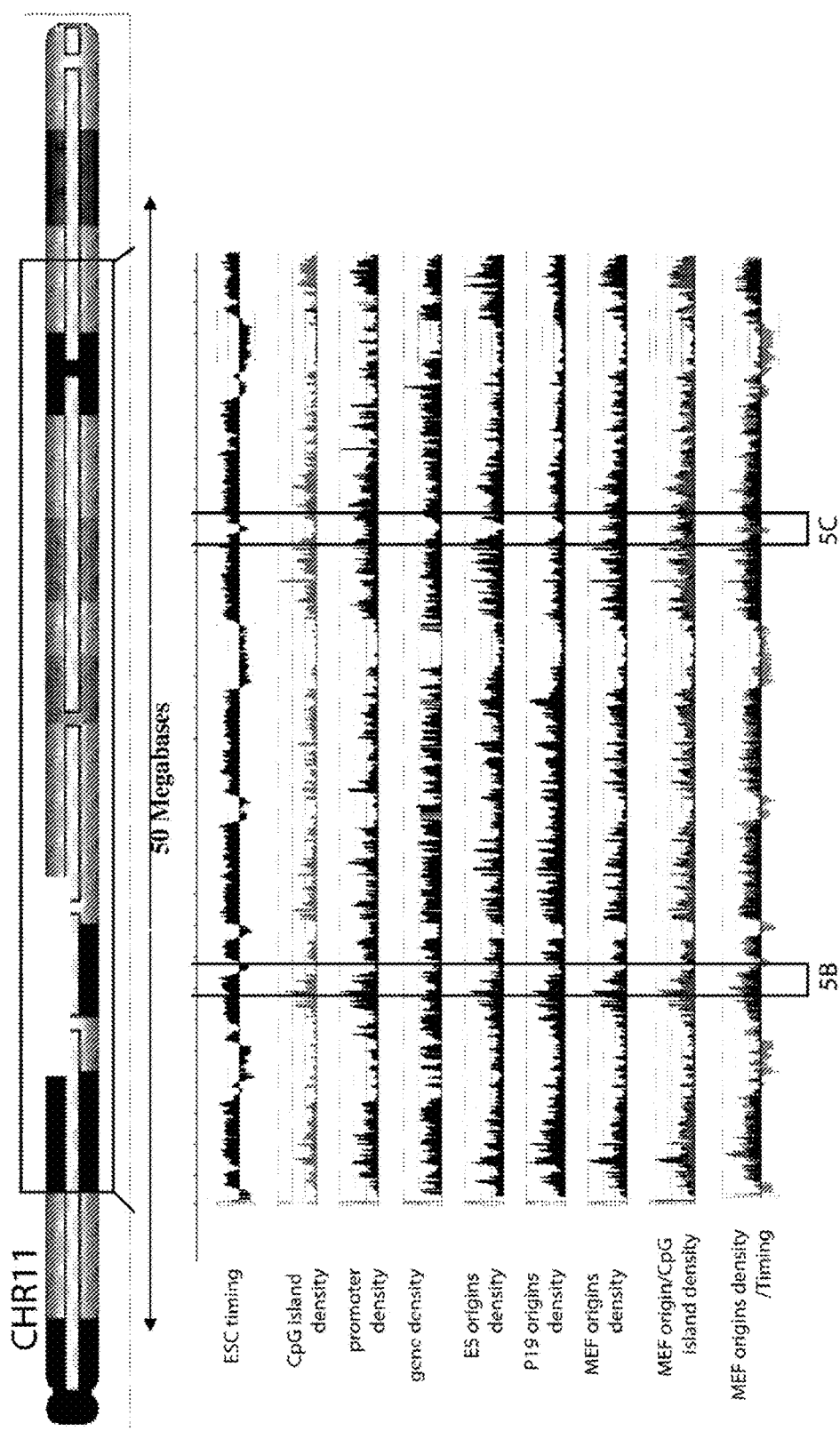

FIGS. 5A-D represent the domains of origin density correlated with domains of CpG island density and replication timing FIG. 5A represents the totality of the 60,S MB on the region defined for the mouse chromosome 11. Diagrams show the replication timing, CpG island density, exon and gene density and replication origins density for mouse cells. The panels below represent the significant overlay of MEF origins and CpG or replication timing domains. The region analyzed in FIGS. SB and SC are highlighted.

FIG. SB represents a 3.S Mb region of mouse chromosome 11. Note that all indicators are relatively high in this early replication region as defined in ES cells.

Figure 5B:
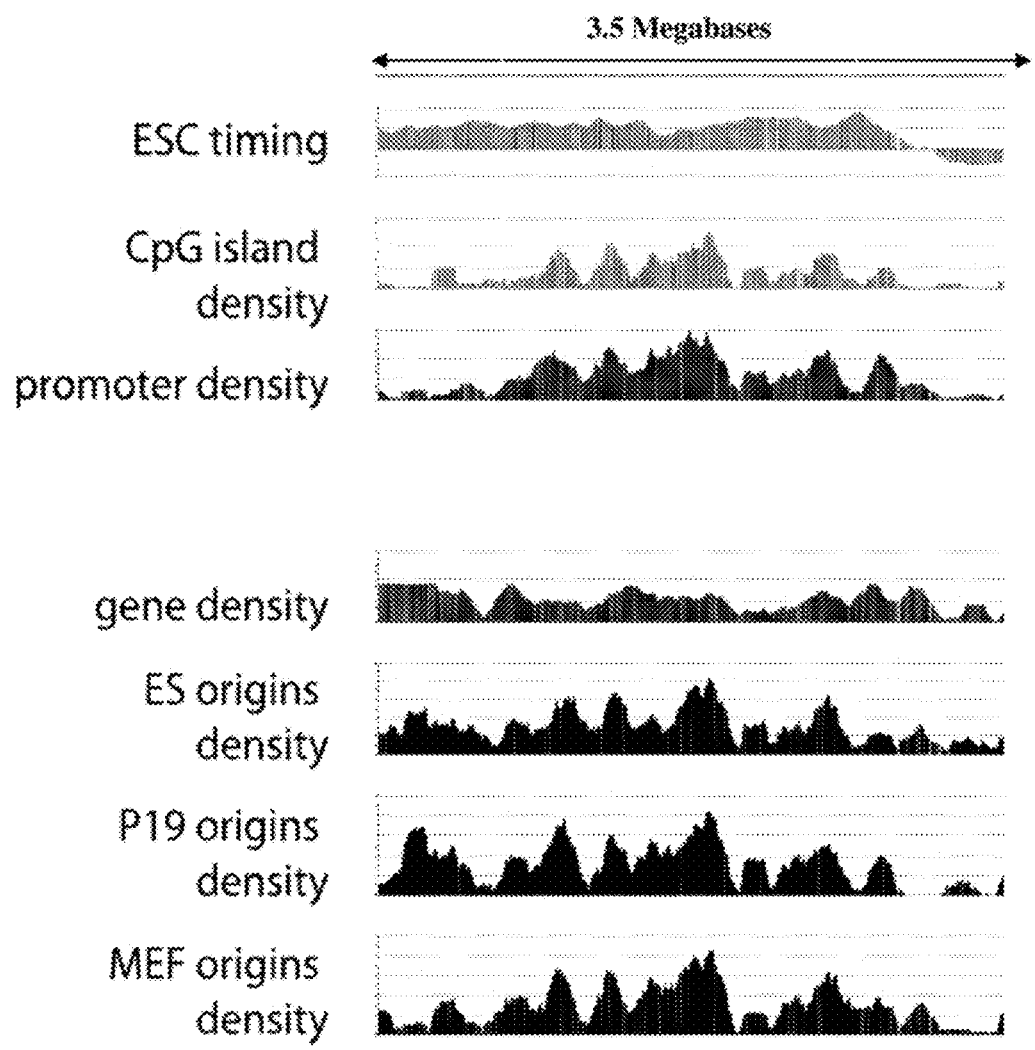
Figure 5C:
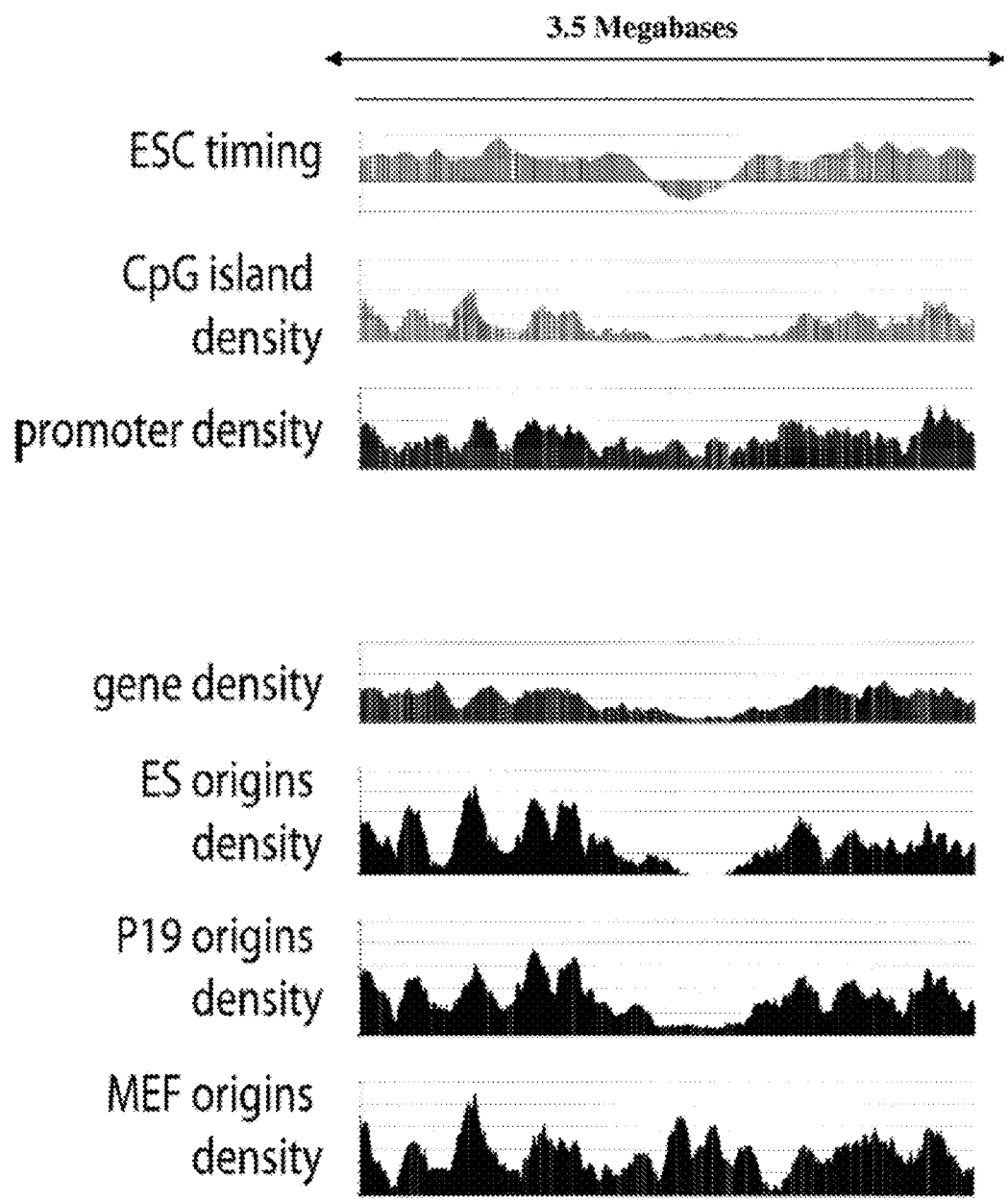

FIG. 5C represents a 3 0.5 Mb region of mouse chromosome 11. Note the differences in origin density between MEF and pluripotent cells in the late replicating domain.

Figure 5D:
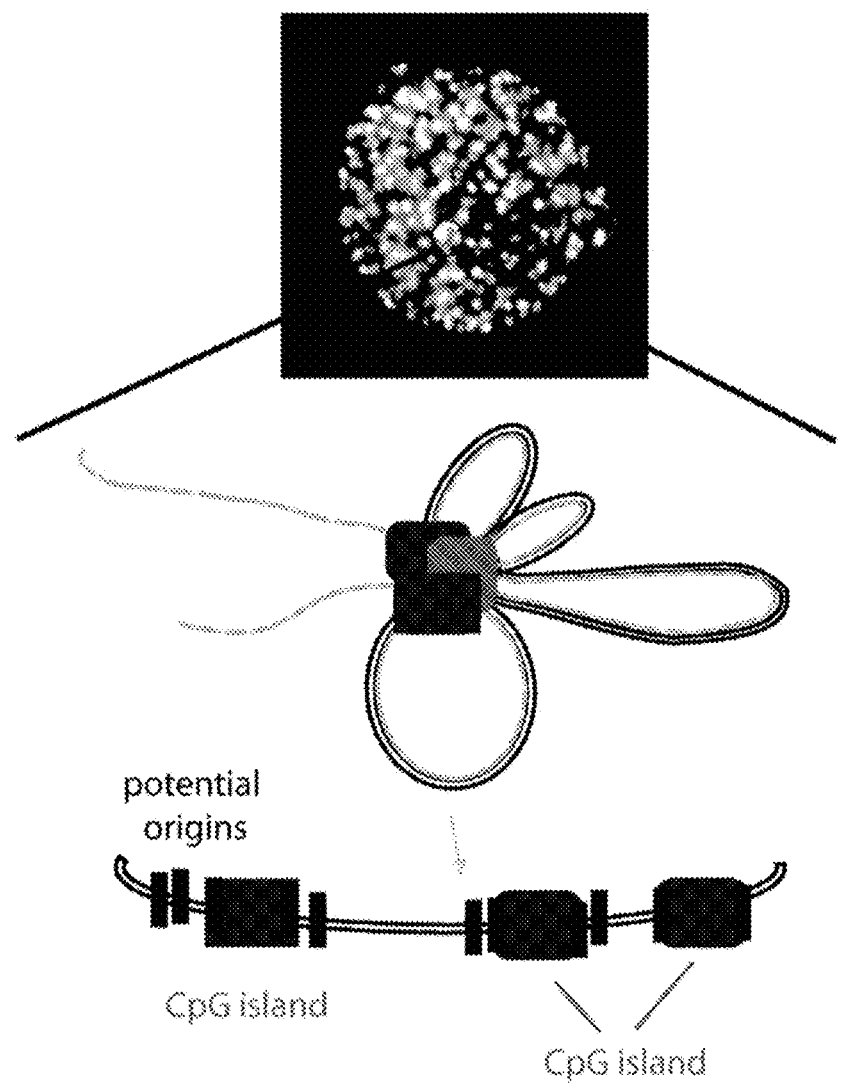

FIG. 5D shows a model illustrating genomic distribution and usage of replication origins in metazoan. Multiple loops could cluster several fired replication origins in foci. For illustration purposes, BrdU positive replication foci are shown (top panel). CpG Island could be a regulatory element for location and for efficiency firing of replication origins. In this model one origin by cluster can be fired in each cell.

FIGS. 6A-E represent the purification process of Nascent Strands DNA from cultured cells.

Figure 6A:
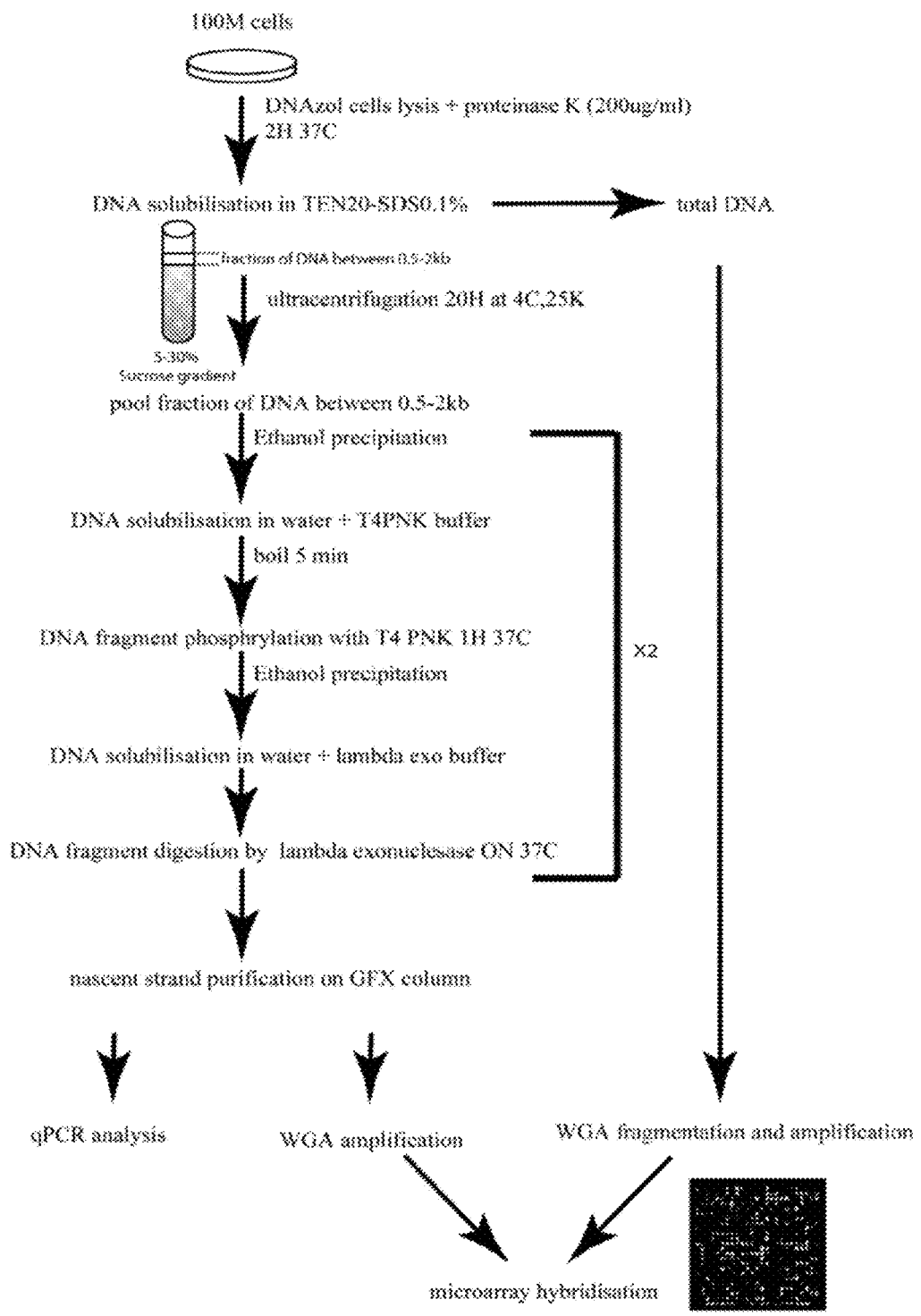

FIG. 6A shows the scheme used for the purification and the analysis of metazoan replication origins.

Figure 6B:
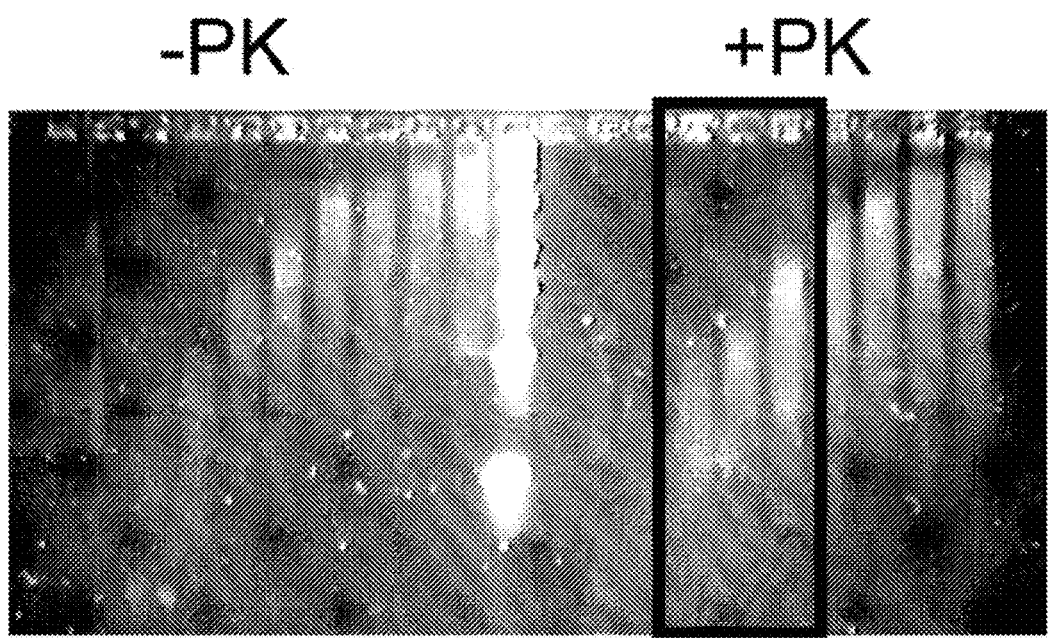

FIG. 6B shows the analysis of the fraction obtained after the sucrose ultracentrifugation step. Fractions were analyzed by alkaline agarose gel electrophoresis. In this particular experiment, proteinase K (PK) was added (+) or not (−) during lysis. Fractions of 0.5-2 kb DNA are pooled (black box) for the following step.

Figure 6C:
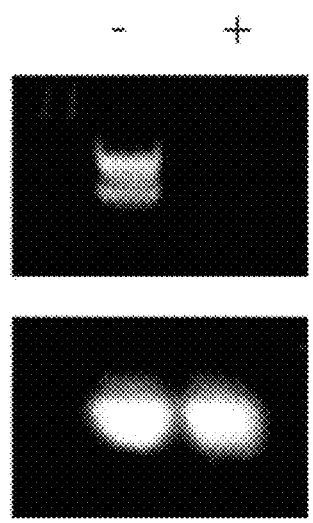

FIG. 6C illustrates the specificity of lambda exonuclease. DNA (upper panel) or RNA (lower panel) samples were incubated with (+) or without (−) lambda exonuclease. The reaction was separated by agarose gel electrophoresis and visualized using GelRed staining.

Figure 6D:
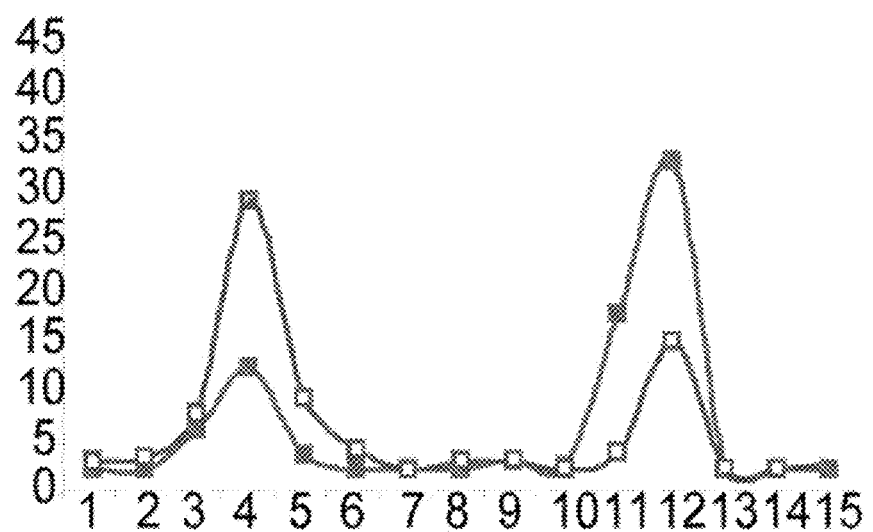

FIG. 6D illustrates the effect of our amplification protocol. Shown is the qPCR analysis of the HoxA locus in P19 cells of the un-amplified Nascent Strands sample (empty square) and the WGA-amplified Nascent Strands (filled square). The x-axis identify the primer used in the qPCR analysis while the y-axis represents the fold enrichment of Nascent Strands compared to negative primers.

Figure 6E:
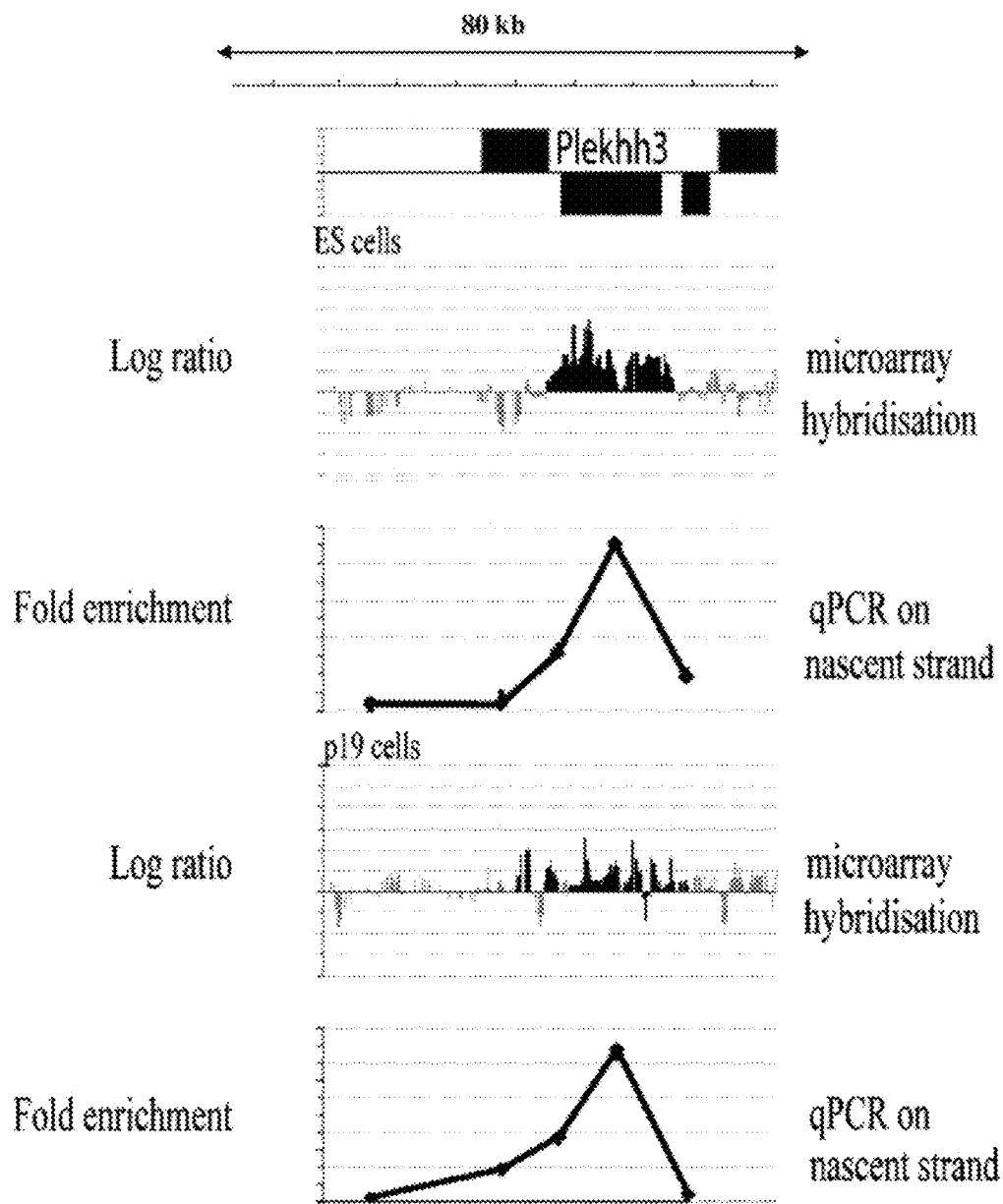

FIG. 6E shows that Nascent Strands signals from microarrays can be observed by qPCR in mouse P19 and ES cells. Genes localization, Nascent Strands signals and qPCR analysis are shown.

Figure 7A:
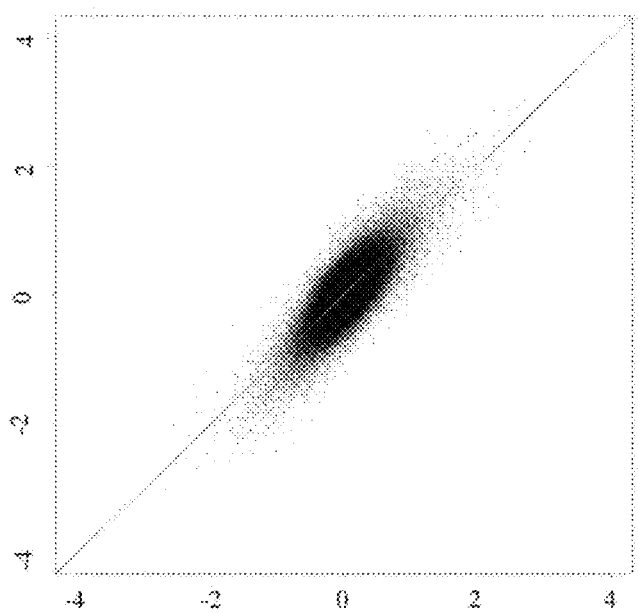
Figure 7B:
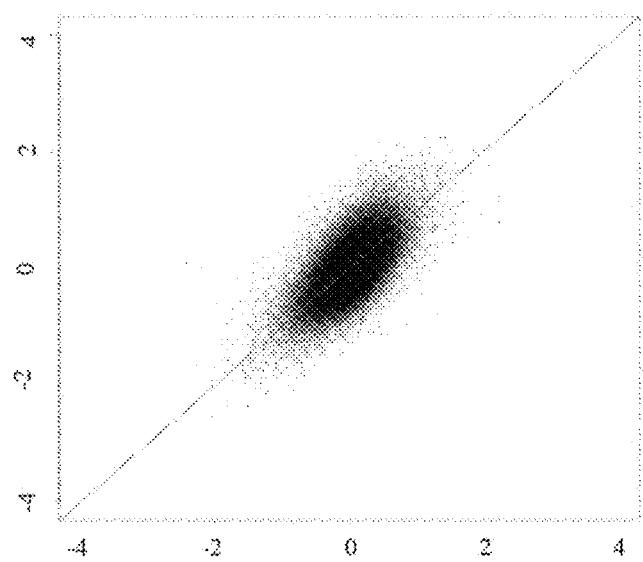
Figure 7C:
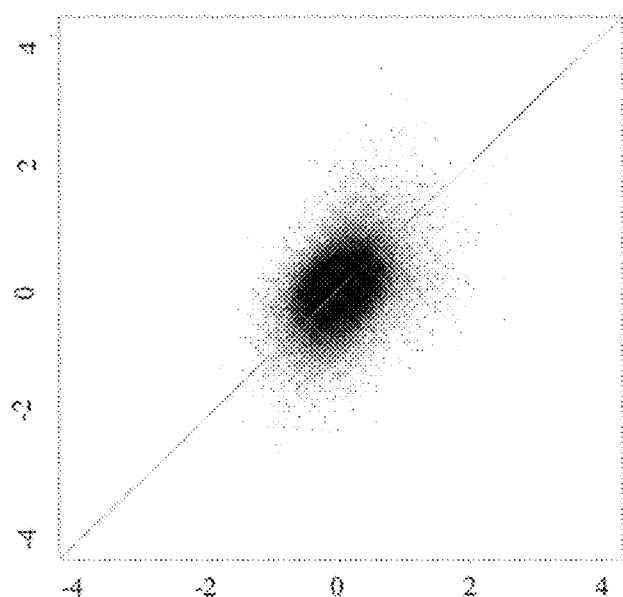
Figure 8A:
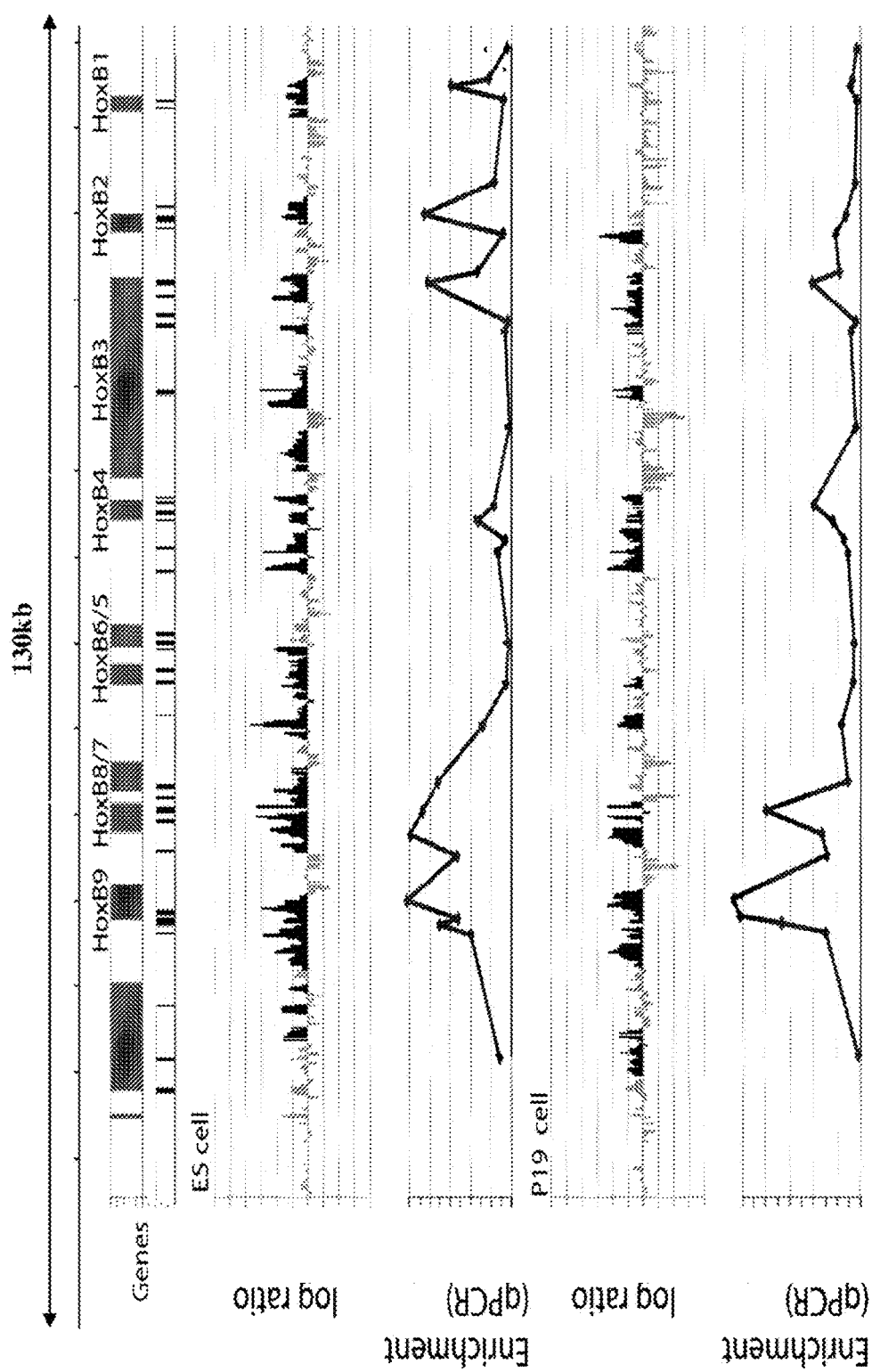
Figure 8B:
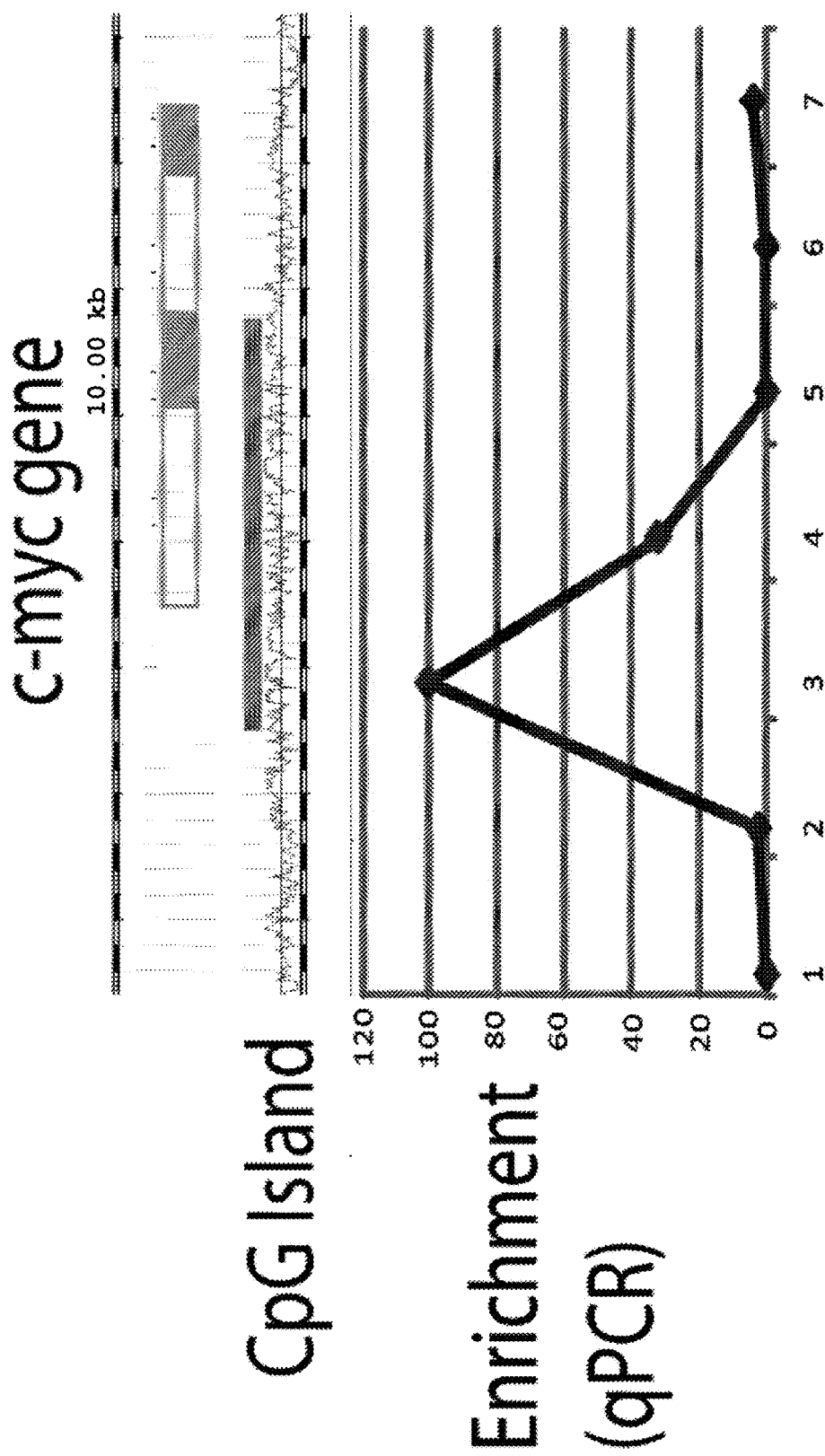
Figure 8C:
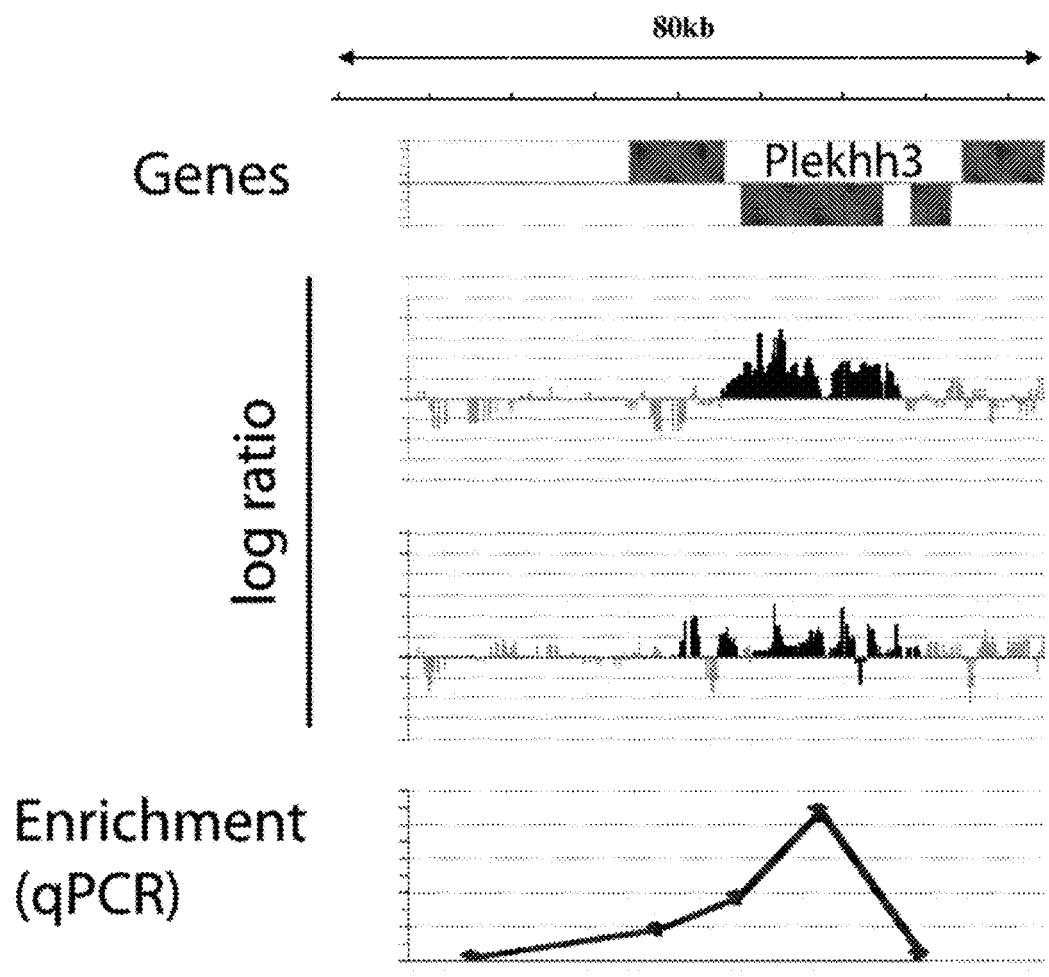
Figure 8D:
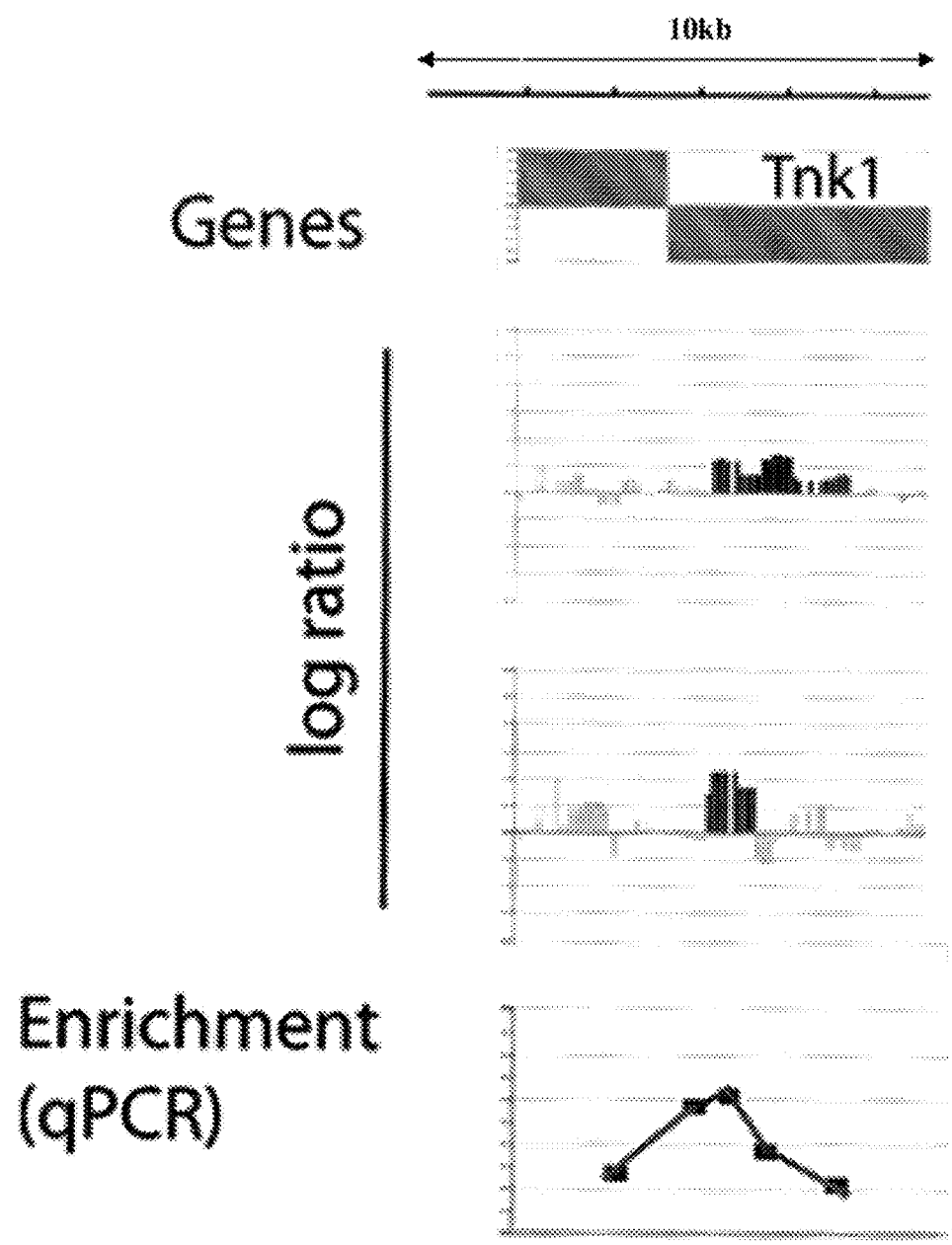
Figure 8E:
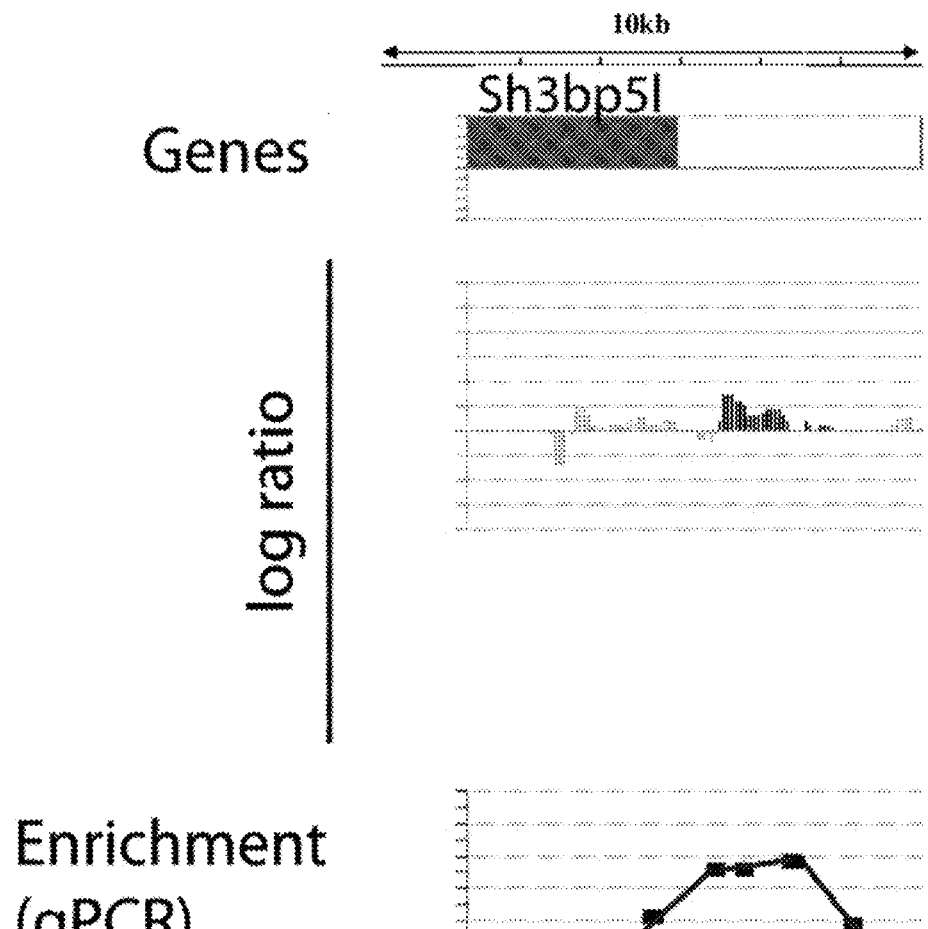
Figure 8F:
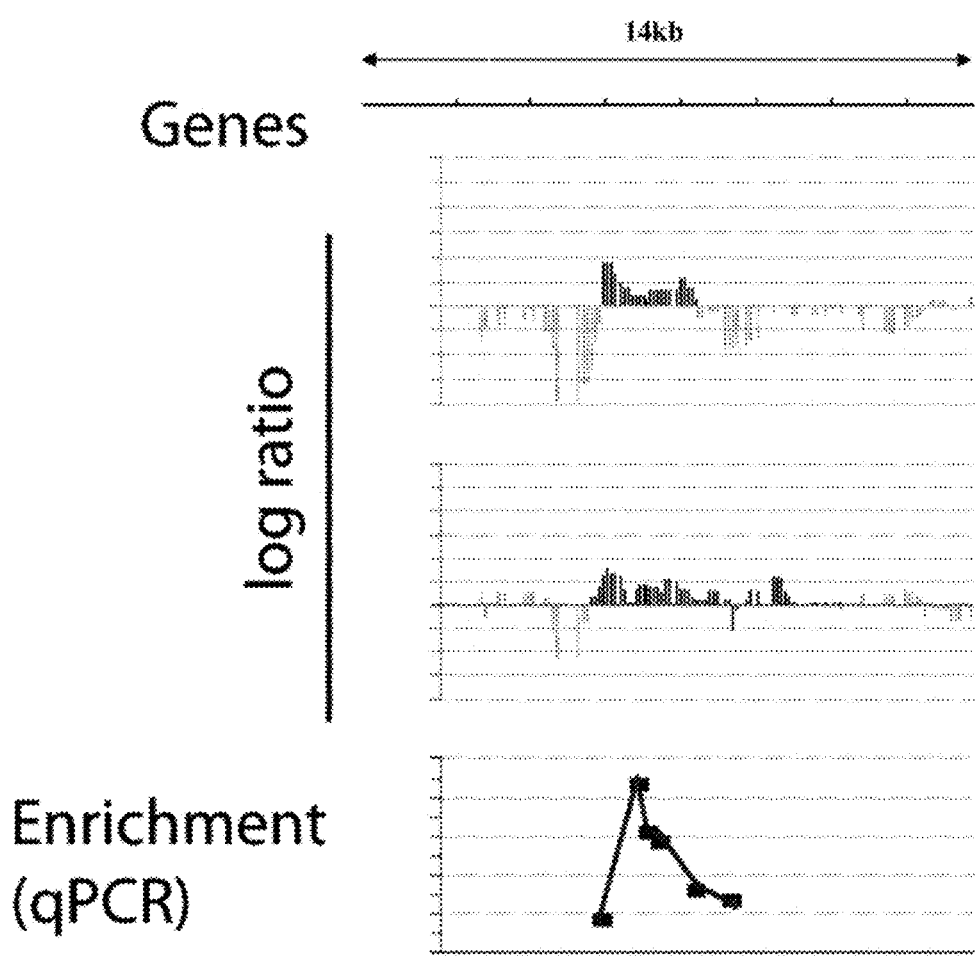

FIGS. 7A-C represent the reproducibility of Nascent Strands purification.

FIG. 7A show scatter plots comparing two biological replicates of purified Nascent Strands from P19 cells. Every dot represents a single probe on the microarray. Its position is determined by the value of the log ratio of the two compared replicates. The coefficient of determination (R2) is 0.7935912.

FIG. 7B show scatter plots comparing two biological replicates of purified Nascent Strands from Kc cells. Every dot represents a single probe on the microarray. Its position is determined by the value of the log ratio of the two compared replicates. The coefficient of determination (R2) is 0.7057634.

FIG. 7C show scatter plots comparing two biological replicates of purified Nascent Strands from ES cells. Every dot represents a single probe on the microarray. Its position is determined by the value of the log ratio of the two compared replicates. The coefficient of determination (R2) is 0.3724884.

FIGS. 8A-F represent the confirmation using qPCR analysis of replication origins identified by microarrays.

FIG. SA represents replication origins analysis of the LoxB locus. Shown is the localization of genes, the Nascent Strands signals from microarray analysis and qPCR analysis for ES and P 19 cells.

FIG. SB shows that our Nascent Strands preparation contains a known origin. Represented is a qPCR analysis of the replication origin of e-mye gene.

FIGS. 8C-8F show that novel replication origins identified in our microarrays can be observed by qPCR in mouse P19 and ES cells. Genes localization, Nascent Strands signals and qPCR analysis are shown. In FIGS. SC, SD and 8F, the upper panel of microarray data is for ES cells while the lower panel is for P19 cells. In FIG. SE, results for ES cells are shown.

FIGS. 9A-F represent the cell cycle distribution of cells used for the Nascent Strands purifications. The DNA content of individual cells is stained and quantified using a flow cytometer. The populations of cells before (2n) and after (4n) DNA replication are indicated. Cells in between 2n and 4n are replicating DNA.

Figure 9A:
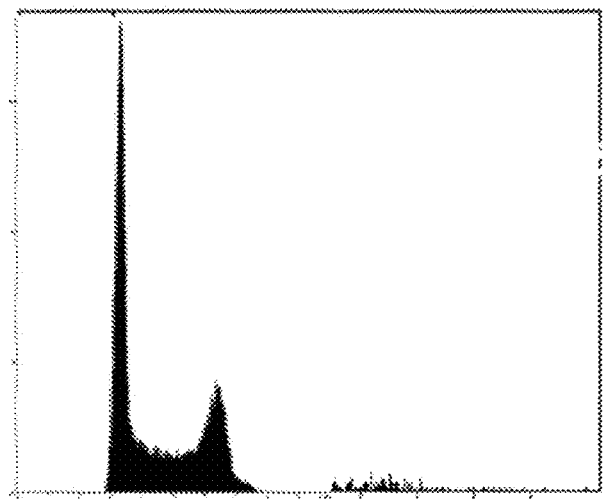
Figure 9B:
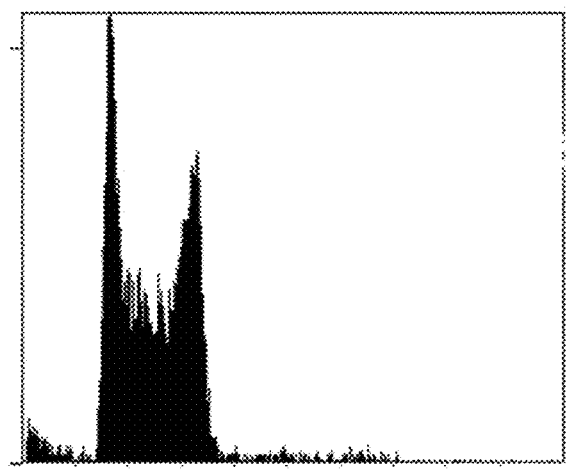
Figure 9C:
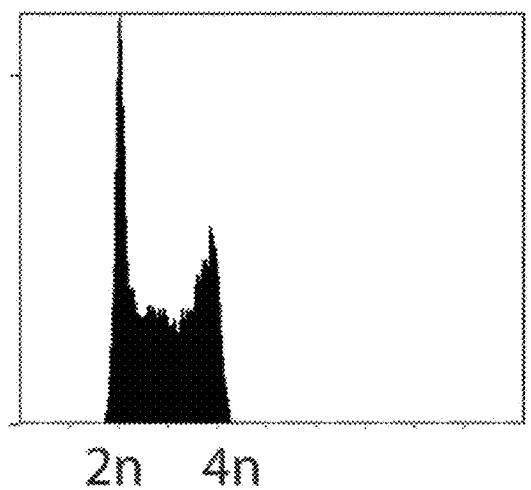
Figure 9D:
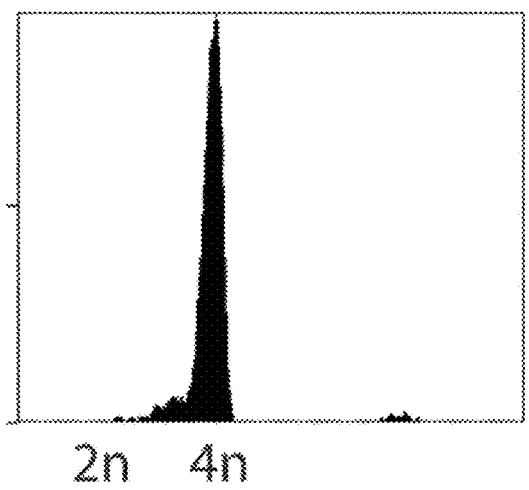
Figure 9E:
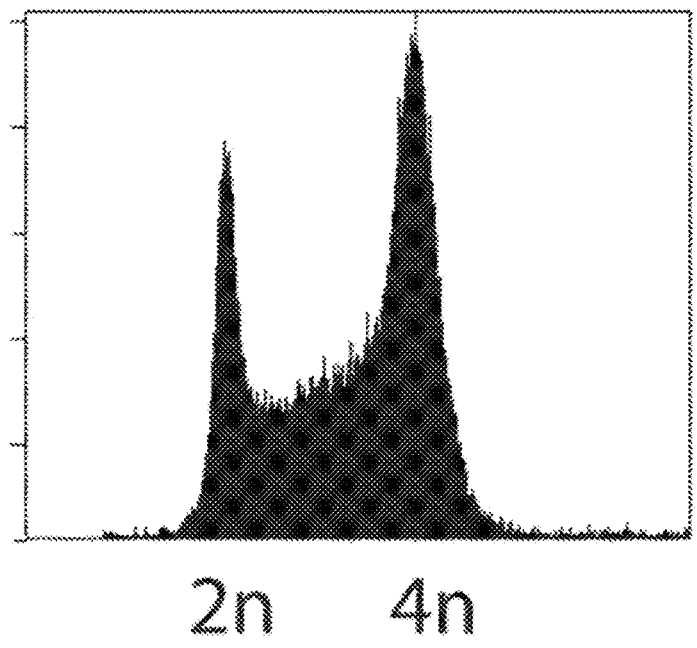

FIG. 9A represents DNA content of MEF cells actively proliferating FIG. 9B represents DNA content of ES cells actively proliferating. FIG. 9C represents DNA content of P19 cells actively proliferating. FIG. 9D represents DNA content of P19 cells arrested in mitosis. FIG. 9E represents DNA content of Kc cells actively proliferating.

Figure 9F:
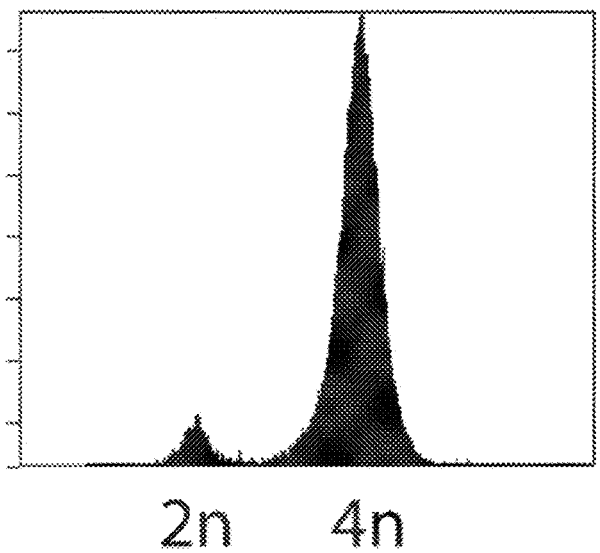

FIG. 9F represents DNA content of Kc cells arrested in mitosis.

FIGS. 10A-H represent the association between CpG Islands and replication origins in ES and P19 cells.

Figure 10A:
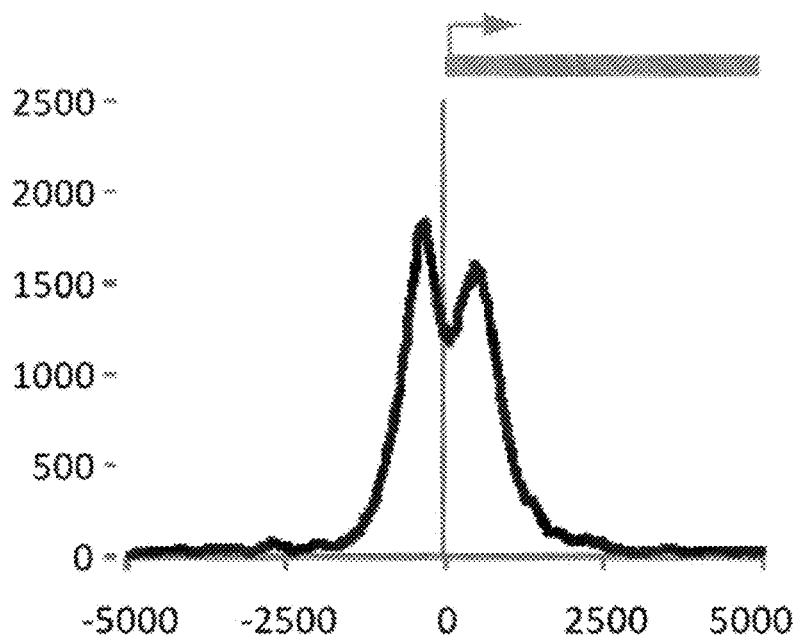

FIG. 10A represents the sum of all the Nascent Strands signals (corresponding to replication origins) around the site of initiation of transcription (TSS: Transcription Start Sites) in mouse ES cells. Shown is the cumulative Nascent Strands signals associated with all TSS.

Figure 10B:
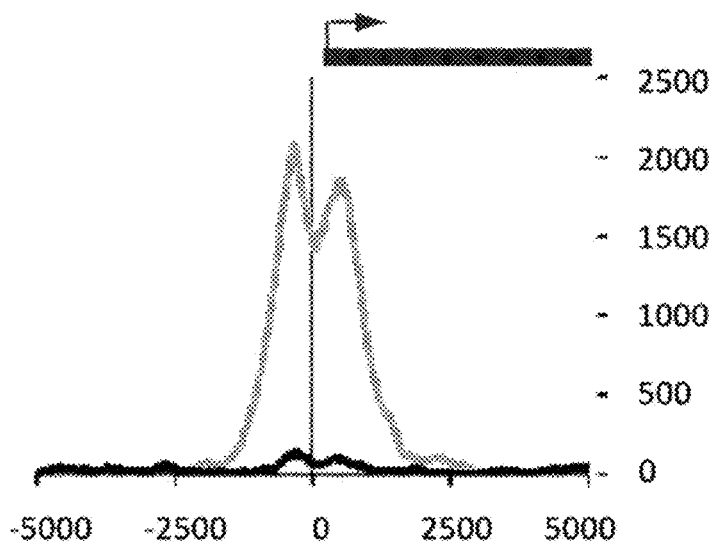

FIG. 10B represents the sum of all the Nascent Strands signals around TSS associated with CpG Islands (CGI, light grey line) or not associated (dark grey line) in mouse ES cells.

Figure 10C:
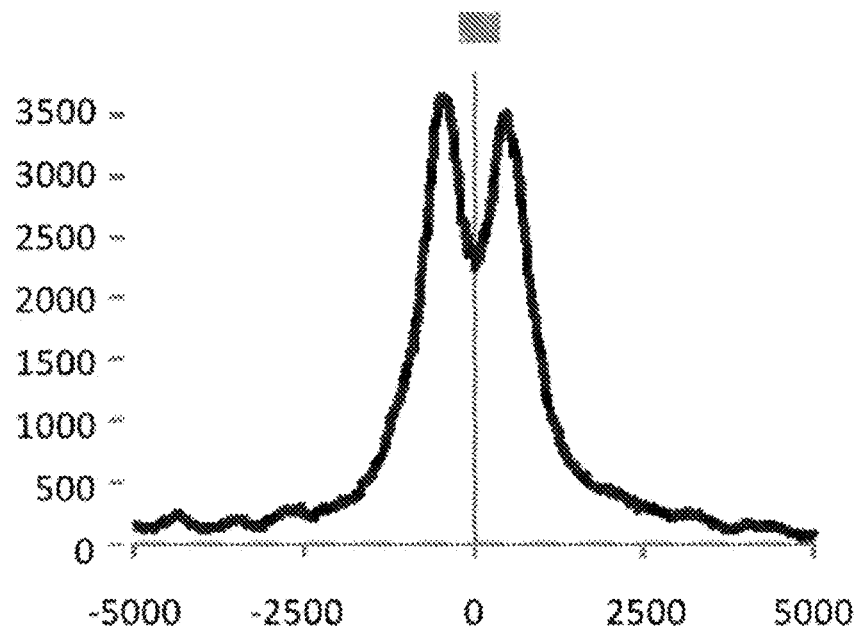

FIG. 10C represents the sum of all the Nascent Strands signals (corresponding to replication origins) around the CpG Islands in mouse ES cells. Shown are the cumulative Nascent Strands signals of all CpG Islands.

Figure 10D:
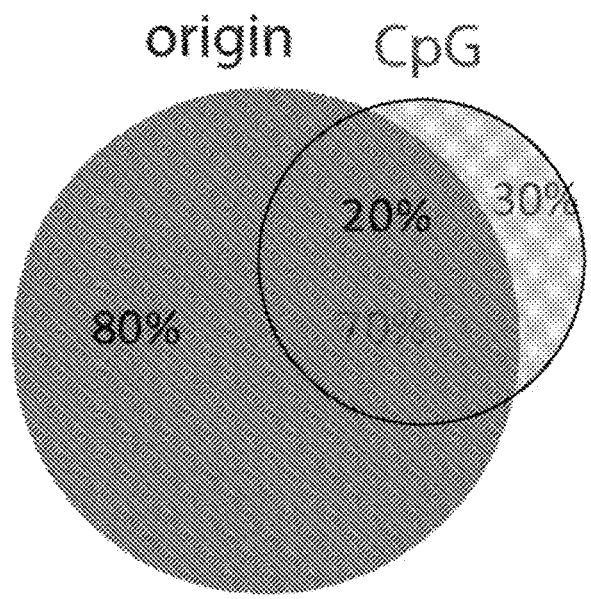

FIG. 10D represents Venn diagram showing the strong association between replication origins and CpG Islands in mouse ES cells. The percentage of association is indicated.

Figure 10E:
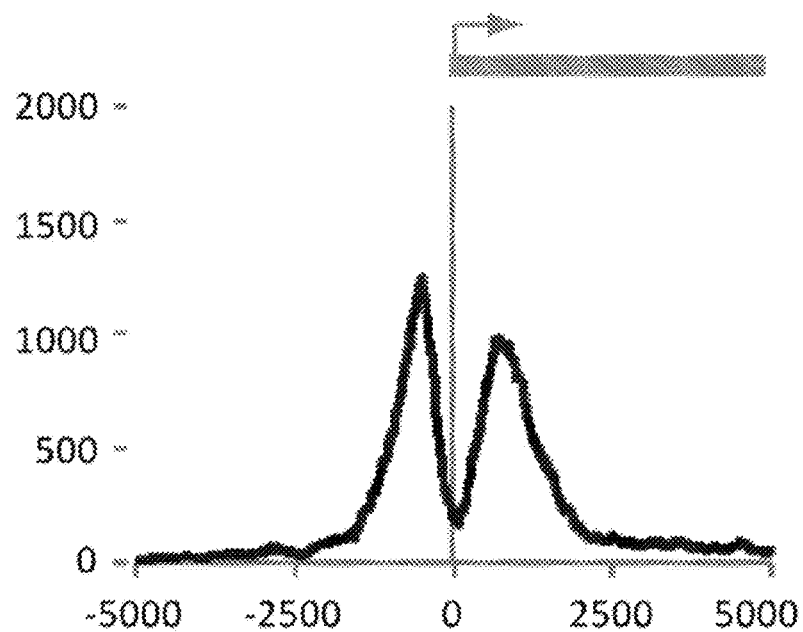

FIG. 10E represents the sum of all the Nascent Strands signals (corresponding to replication origins) around the site of all initiation of transcription (TSS:Transcription Start Sites) in mouse P19 cells.

Figure 10F:
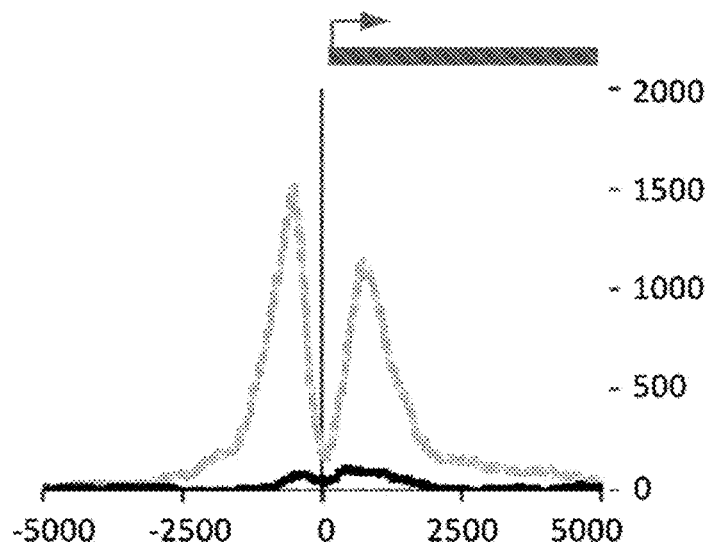

FIG. 10F represents the sum of all the Nascent Strands signals around TSS associated with CpG Islands (CGI, light grey line) or not associated (dark grey line) in mouse P19 cells.

Figure 10G:
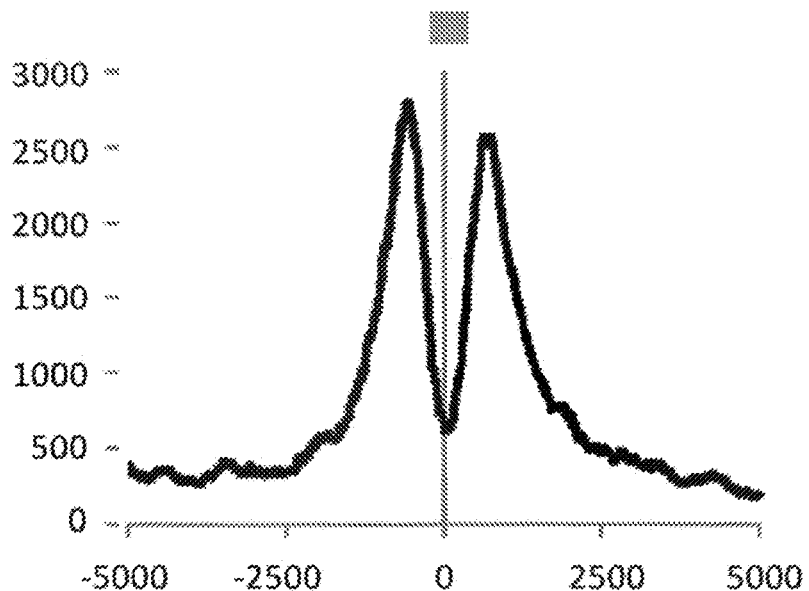

FIG. 10G represents the sum of all the Nascent Strands signals (corresponding to replication origins) around the CpG Islands in mouse P 19 cells. Shown are the cumulative Nascent Strands signals of all CpG Islands.

Figure 10H:
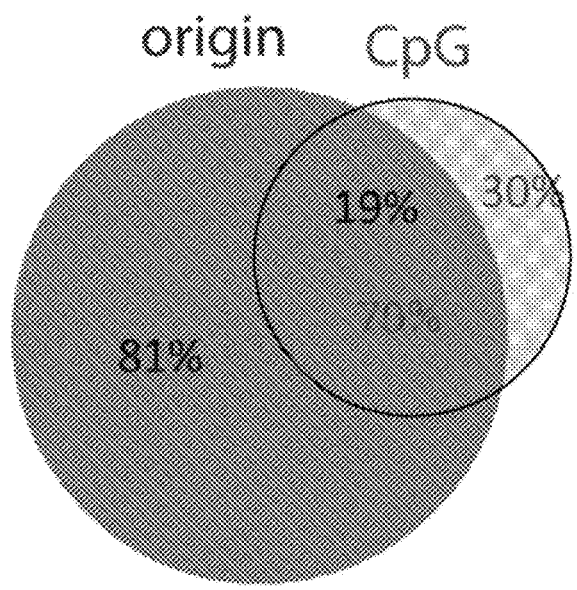

FIG. 10H represents Venn diagram showing the strong association between replication origins and CpG Islands in mouse P 19 cells. The percentage of association is indicated.

Figure 11A:
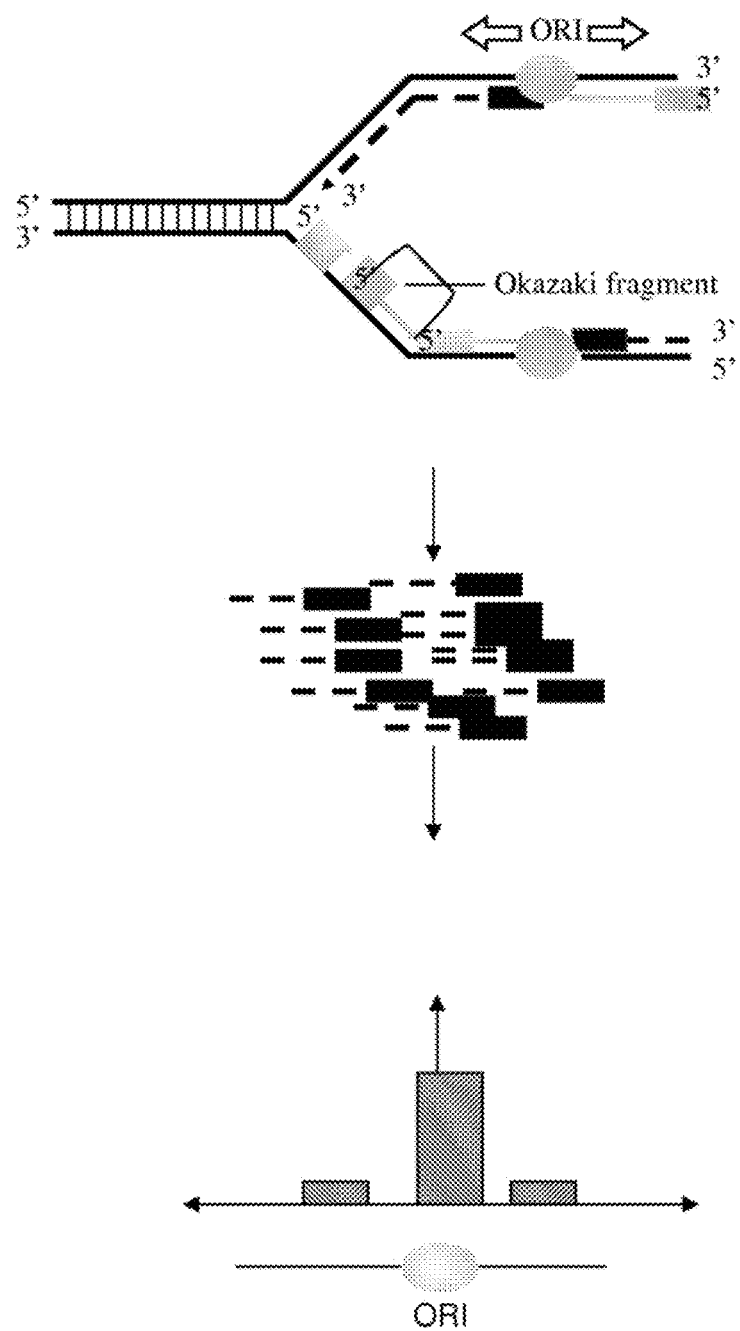
Figure 11B:
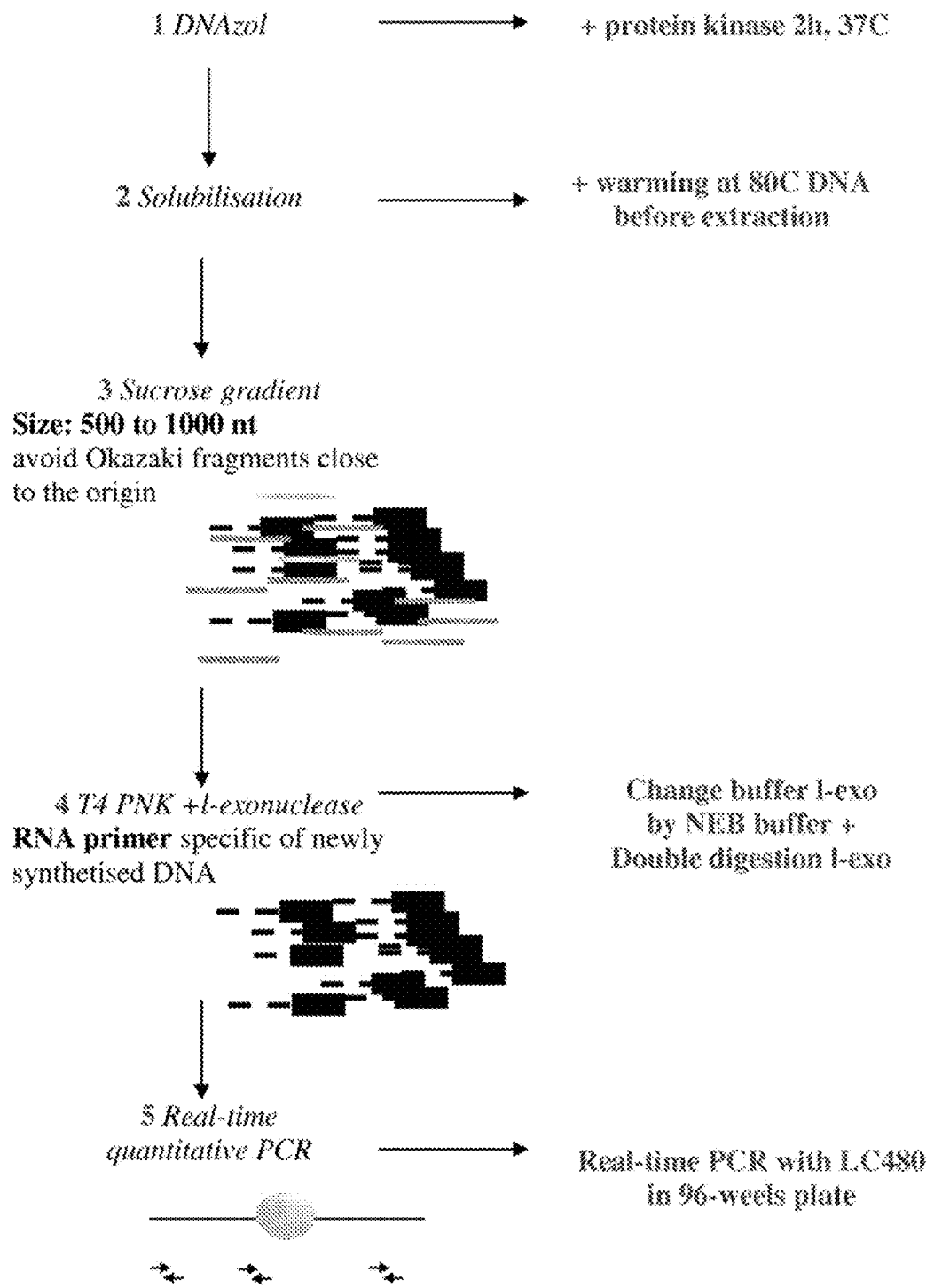

FIG. 11A-B correspond to a schematics representations of the Replication origins mapping by nascent strands relative enrichment assay.

FIG. 11A is a schematic representation of the process: Nascent strands are purified and then analyzed by qPCR. Brocken lines represent nascent DNA, black boxes represent RNA primers.

FIG. 11B represents the detailed process. Cells are first lysed in the DNAzol then purified and total DNA is heated and placed on a sucrose gradient. The sucrose fractions containing DNA fragments of interest between 500 and 2000 base pairs are once phosphorylated by T4 polynucleotide kinase and then digested by lambda exonuclease. After extraction by phenol-chloroform, DNA remaining was again treated with T4 PNK and lambda exonuclease. Purified nascent strands are analyzed by qPCR. Grey lines represent contaminant DNA.

FIGS. 12A-F represent the improvement of purification steps of nascent strains

Figure 12A:
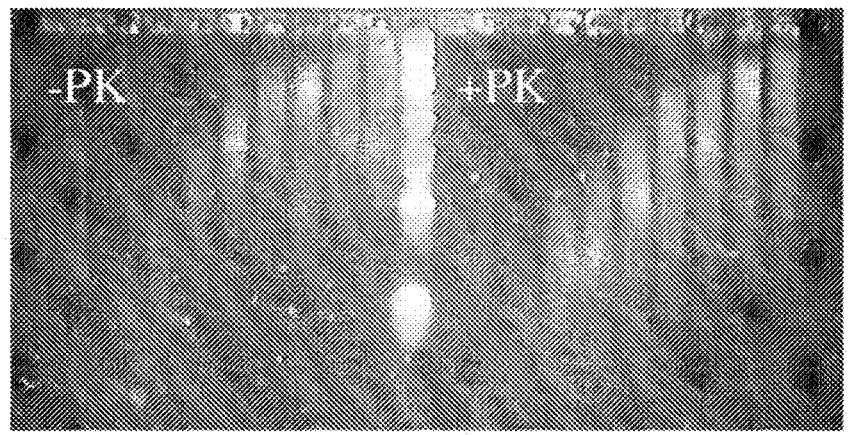

FIG. 12A represents the migration in an agarose gel of nascent strands recovered at the end of the purification after sucrose fractionation, after treatment (+PK) or not (−PK) of cell lysate obtained with DNAzol, with T4 PNK kinase.

Figure 12B:
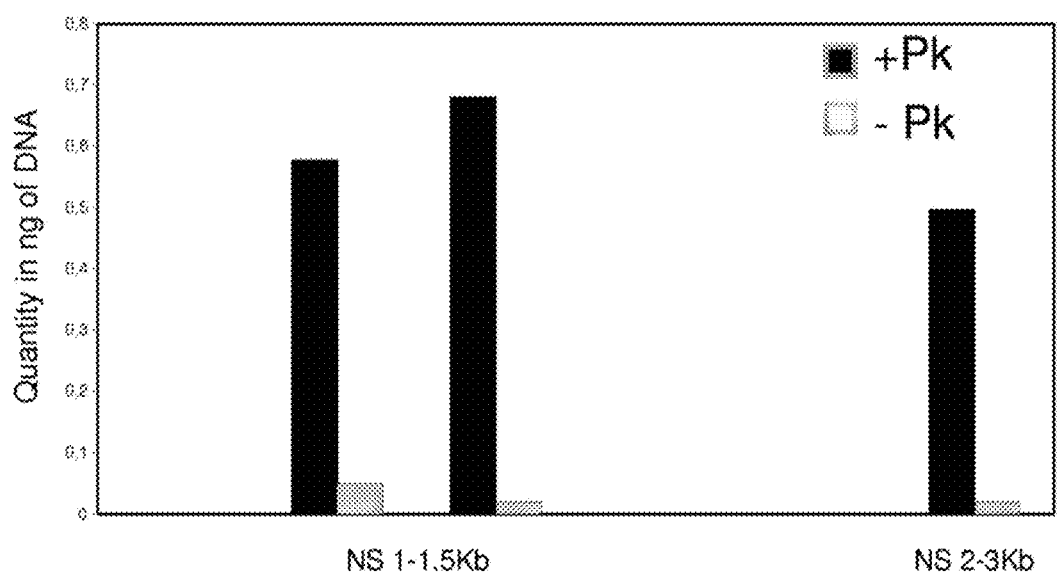
Figure 12C:
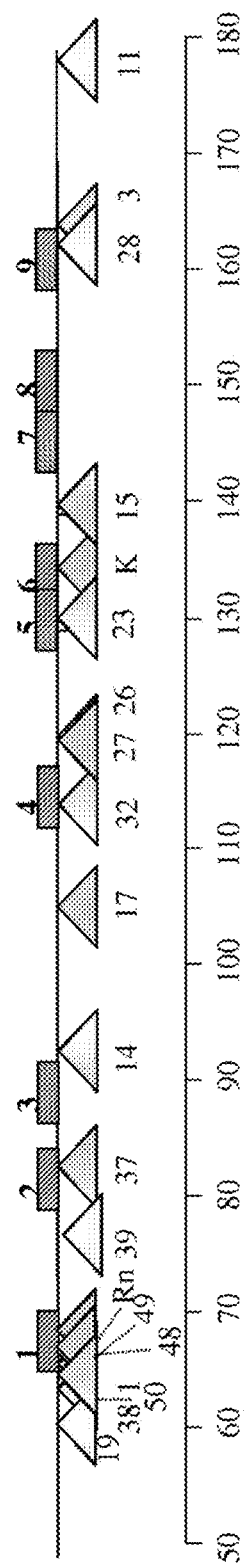

FIG. 12B represents an histogram showing the increase of the amount and enrichment of nascent strands on hoxB9 locus. NS means Nascent strands. Black columns correspond to DNA treated with T4 PNK, and grey columns correspond to non treated DNA.

Figure 12D:
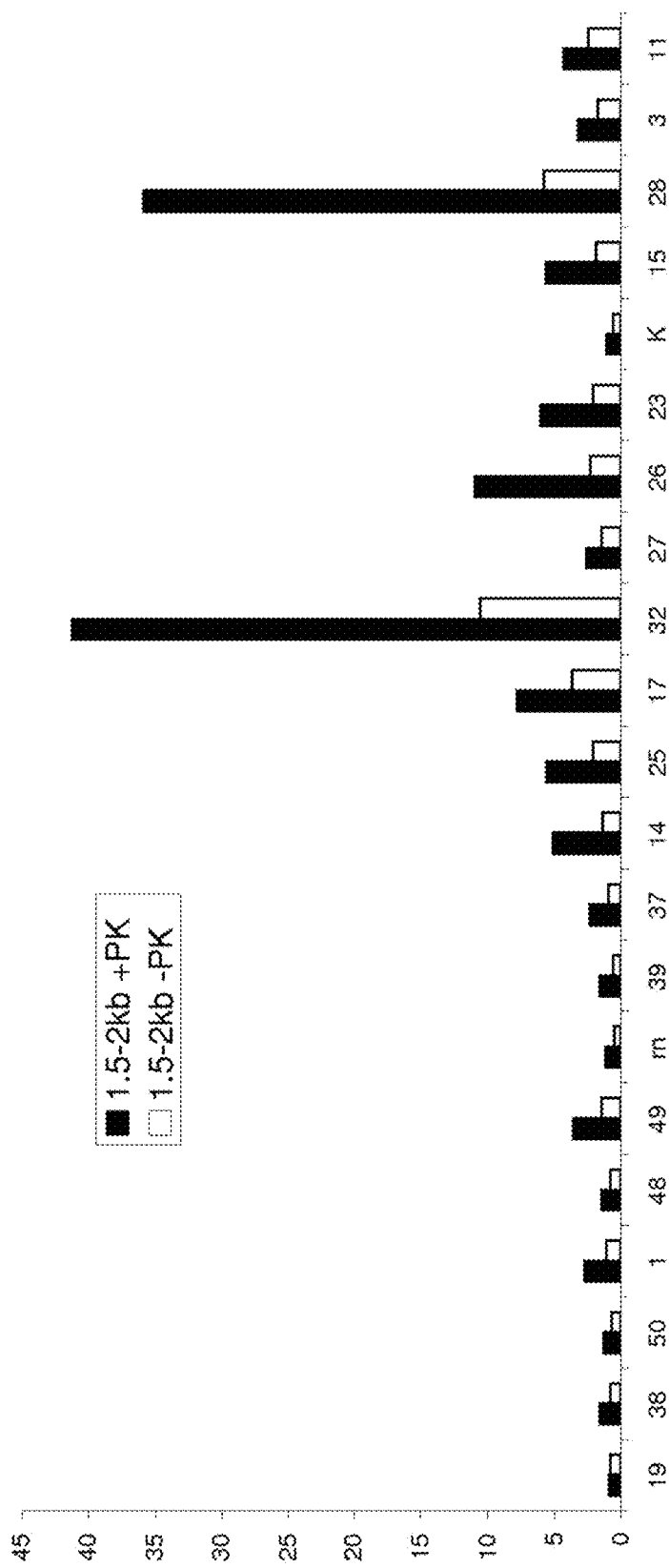

FIG. 12D represents Hoxb9 locus. Black boxes represent genes and triangles represent primers used for qPCR. Scale: in kilobases FIG. 12D represents an histogram showing the increase of enrichment after second round of T4 PNK+lambda exonuclease treatment on hoxb9 origin. Y-axis corresponds to enrichment.

Figure 12E:
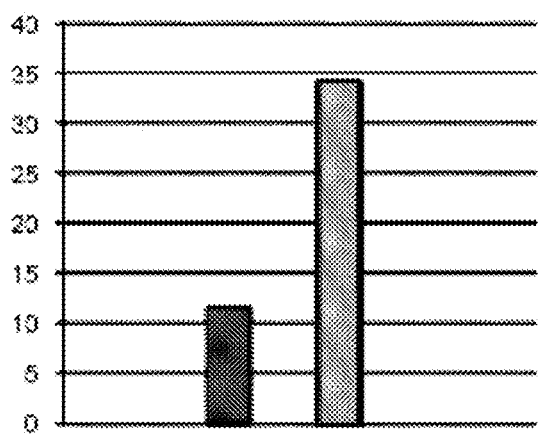

FIG. 12E represents an histogram showing the increase of enrichment, of nascent strands of 1-1.5kb after second round of T4 PNK+lambda exonuclease treatment on hoxb9 origin. Y-axis corresponds to enrichment. NS means nascent strand.

Figure 12F:
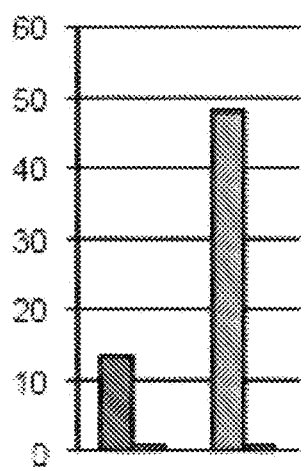

FIG. 12F represents an histogram showing the increase of enrichment, of nascent strands of 1-1.5kb after second round of T4 PNK+lambda exonuclease treatment on e-myc origin. Y-axis corresponds to enrichment. NS means nascent strand.

Figure 13A:
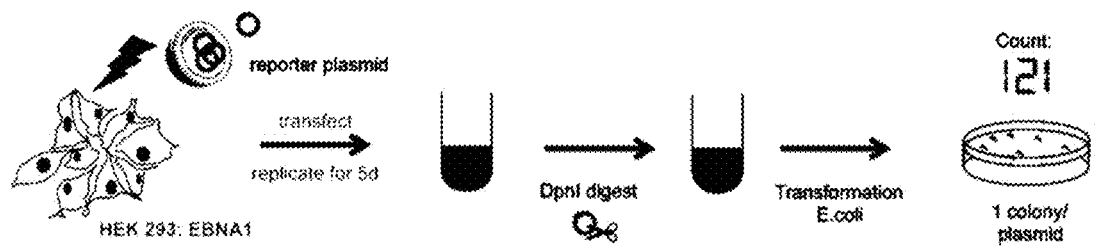

FIGS. 13A and B illustrate the efficacy of the replication origin.

FIG. 13A represents the procedure followed for the experiment.

Figure 13B:
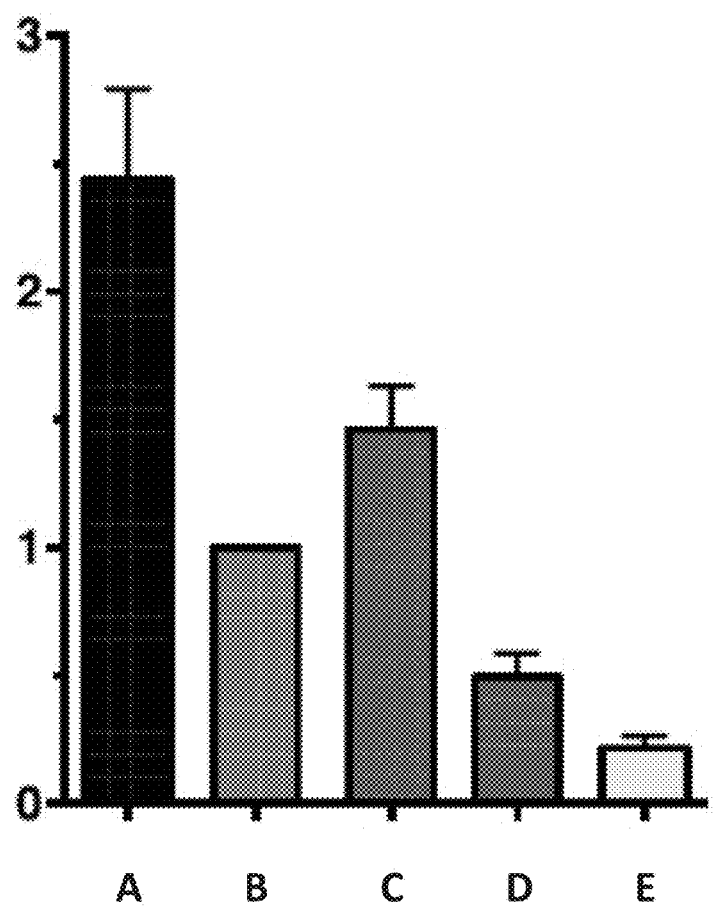

FIG. 13B represents a graph showing the plasmid enrichment (i.e the DNA replication) compared to c-myc origin. A: OriP, a replication origin of a virus, B: c-myc origin, C: WT OGRE, D: Delta OGRE and E: Modified OGRE.

Figure 14A:
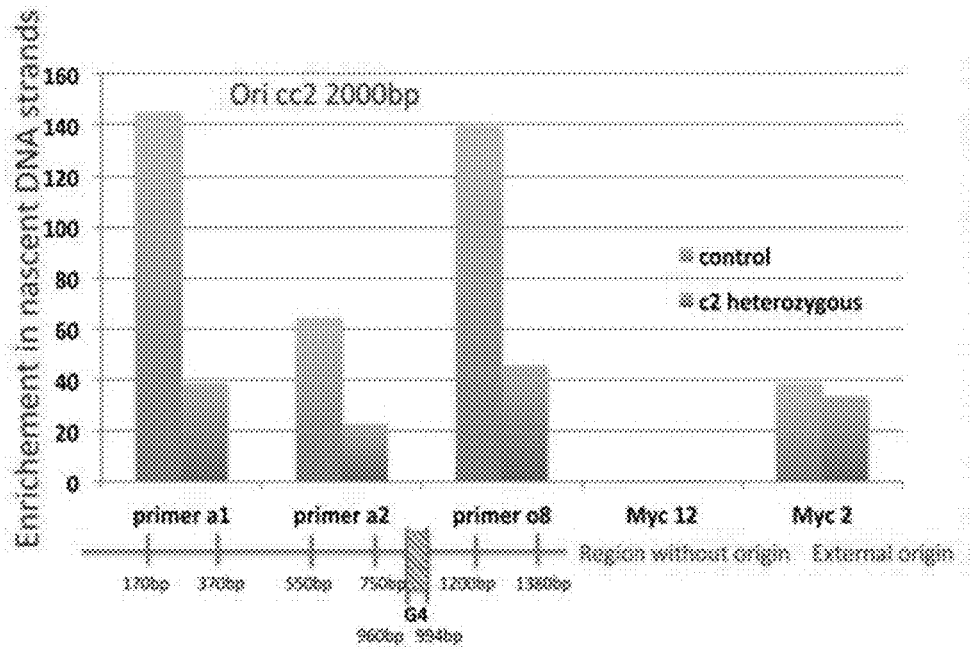
Figure 14B:
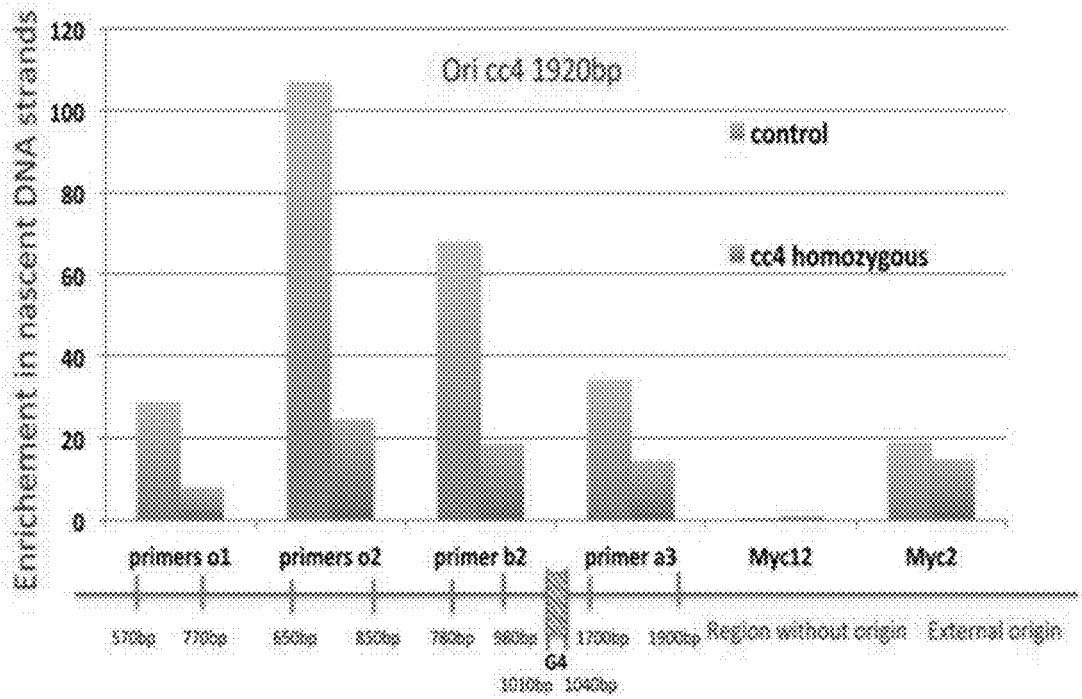

FIG. 14A to B show that deletions of the G4 element in the OGRE motifs strongly affects DNA replication origin activity Two known origins (CC2 and CC4) were selected, which contain OGRE/G4 elements. Using the CRISPR/cas method, G4 elements were deleted and the replication origin activity analysed at the corresponding loci as well as in a known control region containing (Myc 2) or not containing (Myc 12) an origin. The analysis of replication origin activity was performed by the purification of nascent strands, followed by qPCR analysis.

FIG. 14A represents the results in cc2 gene and compares WT cc2 origin to an heterozygote deletion of the cc2 origin.

FIG. 14B represents the results in cc4 gene and compares WT cc2 origin to an homozygote deletion of the cc4 origin.

EXAMPLES

Example 1: Protocole for Nascent DNA Purification (FIGS. 11 and 12)

Precipitation DNA
dividing cells (2.5×108 to 5×108=2*150 mm) were washed with PBS.
cells were harvested and lysed in 15 ml of DNAzol® for 5 min at room Temperature (RT)
Proteinase K was added in DNAzol to 200 ng/ml, and incubated at 3 7° C. 2 hours. Centrifugation at 4000 RPM, 15 min and the supernatant is rescued.
To the supernatant, 15 ml of ethanol 100% were added to precipitated for S min at RT.
Spooled out the DNA using a drawn pasteur pipette in a tube with 5 ml of ethanol 70% for 5 min at RT
spooled out the DNA using a drawn pasteur pipette in a new dry tube 2 ml to dry the pellet (30 min at RT).
DNA is resuspended in 2 ml of TEN20 at 70° C. tris 1 O mM pH7.9 final
EDTA 2 mM final
NaCl20 mM final
SDS 0.1%
RNasin 1000 U
The solution was boiled for 10-15 min, chilled on ice
Sucrose Gradiant NS Purification
Load 1 mL onto a single neutral 5 to 30% sucrose gradient prepared in TEN500 in a 38.5-ml centrifuge tube. tris 1 O mM pH7.9 final
EDTA 2 mM final
NaCl300 mM final
Gradients were centrifuged in a Beckman SW28 rotor for 20 hat 24 000 rpm at 4° C. 1 ml Fractions were withdrawn from the top of the gradient using a wide-bore pipette tip 50 µl of each fraction was run with appropriate size markers on a 2% alkaline agarose gel, ON at 4° C. at 40-50 volt.
neutralized gel with TBEIX and stained with GelRed.
Fractions corresponding to 0.5-1 kb, 1-1.5 kb, 1.5-2 kb and 2-3 kb were rescued and precipitated with 2.5 Vol of ethanol 100% 15 mM at −80° C.
Pellets were washed with I ml of ethanol 70% and resuspended in 20 µl of water with 100 U of RNasin.
DNA Contaminant Withdrawn
1—After addition of 2 µl Buffer PNK (New England Biolabs), fractions were boiled for 5 min, chilled on ice, 2—phosphorylation with T4 polynucleotide kinase in a volume of 100 µl final vol T4 mix:

| water | qsp 80 ul |
|---|---|
| Buffer PNK NEB 10X | 1X |
| ATP | 50 nM (0.05 ul of 100 mM) |
| T4 PNK | 20 U (2 ul of 10 U/ul) |

The reaction is incubated at 37° C. for 1H,15 min at 75° C. and directly precipitated by ethanol (2.5 vol)-Na-acetate (0.3M) for 15 min at −80° C.

3—Pellets were washed with 1 ml of ethanol 70% and resuspended in 50 µl of water with 100 U of RNasin.

4—The remainder is digested with 5 µl of lambda exonuclease in a final volume of 100 µl Lambda exo mix:

| water | qsp 50 ul |
|---|---|
| L-exo buffer 1 OX | 1X |
| L-exo (Fermentas 20 U/µl) | 5 ul |
| BSA | IX (1ul of 100X) |

Fermentas L-exo buffer
67 mM glycine-KOH (pH 9.4)
2.5 mM MgCl2
50 µg of bovine serum albumin per ml)
The reaction is incubated overnight at 37° C.
Aliquots of both the digested DNA and the undigested control were run on an 2% agarose gel.

5—the nascent strands were extracted once with phenol/chloroform/JAA and once with chloroform/JAA, and ethanol (2.5 vol)-Na-acetate (0.3M) precipitated for 15 min at −80° C.

6—Pellets were washed with 1 ml of ethanol 70% and resuspended in 20 µl of water.

7—The NS is subjected to another step of phosphorylation by T4 PNK and lamda-exo digestion (2- to 5-)

8—The final NS resuspended in 50 nl of tris 10 mM is directly quantified with Roche-LC480.

Example 2: Nascent Strands Amplification (FIGS. 11 and 12)

Purification of Nascent Strand with Cyscibe-GFX kit
Elution in 50 ul
use 10 ul and amplify with WGA-Sigma kit without the first fragmentation step.
Purify amplicons with nucleospin kit with a ⅕ dilution in NBA buffer prior to fix on column.
Elution in 50 µl.
LC480 (Light cycler 480) on 0.1 a 0.5 ul of the amplicon.

Example 3: Genome-Wide Analysis of Replication Origins in Five Different Cell Types Reveals Several Choices but a Conserved Repeated Element Introduction In metazoans, thousands of chromosomal sites are activated at each cell cycle to initiate DNA synthesis and permit total duplication of the genome. They all should be activated only once to avoid any amplification and maintain genome integrity. How these sites are defined remains elusive despite considerable efforts trying to unravel a possible replication origin code. In *Saccharomyces cerevisiae*, DNA replication origins are specifically identified by specific DNA elements, called Autonomous Replication Sequence elements (ARS), which have a common AT-rich 11 bp specific consensus. However, sequence specificity identifies but not determines origin selection. Indeed, of the 12,000 ACS sites present in *S. cerevisiae* genome only 400 are functional [Nieduszynski C A, et al. *Genes Dev.* 2006 Jul. 15; 20(14): 1874-9]. In *S. pombe*, ARS elements were also identified but they do not share a specific consensus sequence like in *S. cerevisiae*. Here, DNA replication origins are characterized by AT-rich islands [Dai J, et al. *Proc Natl Acad Sci U S A.* 2005 Jan. 11; 102(2):337-42; Heichinger C, et al. *EMBO J.* 2006 Nov. 1; 25(21):5171-9] and poly-dA/dT tracks.

In multicellular organisms, it was more difficult to identify common features of DNA replication origins. No consensus sequence element has been found, which can have predictive value, although specific sites are recognized as DNA replication origins in chromosomes of somatic cells. It was soon suspected that metazoan ORis might be linked to other genetic features of complex organisms as the requirement to coordinate DNA replication not only with cell growth but also cell differentiation, and correlations with transcription and/or chromatin status have been found [Cayrou C, et al. *Chromosome Res.* 201 O January; 18 (1): 13 7-45]. However, identification of replication origins has been hampered by the lack of a genetic test as the ARS test in yeast, and methods to map replication origins which were not always adapted to a robust genome-wide analysis. First recent genome-wide studies to map origins in mouse and human cells (Cadoret et al., 2008; Sequeira-Mendes et al., 2009) have observed a correlation with unmethylated CpG islands regions as well as some overlap with promoter regions [Sequeira-Mendes J, et al. *PLoS Genet.* 2009 April; 5(4):e1000446]. However, it is not clear whether CpG islands are here a specific mark of replication origins or of the associated transcription promoters.

The Inventors tried to reveal new features of eukaryotic origins, first by upgrading the method used to map nascent stands DNA at origins to a specificity and reproducibility compatible with a genome-wide analysis compatible with the use of tiling arrays. Then, the Inventors used this method for four kinds of cell systems: mouse embryonic stem cells (ES), mouse teratocarcinoma cells (P19), mouse differentiated fibroblasts (MEFs), and *Drosophila* cells (Kc cells). The aim of using mouse cells and *drosophila* cells was to possibly detect conserved features in evolution and the aim of using mouse cells in different cell behaviours was to analyze the contribution to differentiation as opposed to pluripotent cells.

Genome-Wide Replication Origins Maps

The RNA-primed nascent DNA procedure of preparation was initially improved using P 19 cells that grow in large amounts, and the method is detailed in Supplementary material and FIG. 6A-E. It was checked with up to 5 entirely different duplicates.

Nascent strand preparations were hybridized on tiling micro-array (Nimblegen, oligonucleotides spaced every 100 bp). The full data set consists of continuous 60.4 Mbp on mouse chromosome 11 and 118.3 Mbp of *Drosophila* genome. Origins maps show enrichment at specific genomic locations with a high degree of reproducibility (FIGS. 1A-C and FIG. 7A-C). The Inventors validated the Ori maps of known origins by qPCR analysis of mouse e-Mye gene (FIG. 8B) and HoxB domain (FIG. 8A) as well as of randomly chosen putative Oris (FIG. 8C-F). No specific signals was observed when total DNA or 'Nascent Strands' from mitotic cells was used for hybridization (FIGS. IB, IC and FIG. 9), or when NS was RN Ase treated before exonuclease digestion (data not shown), confirming the specificity of our purification procedure. Importantly, no replication origin could be detected when using 'nascent strands' purified from non-cycling mitotic cells, confirming the specificity of our purification scheme. The Inventors identified 3299, 3263, 1896 and 8460 origins from ES, P1 9, MEF and Kc cells respectively Replication Origins Distribution The method used allows scoring potentially all activated origins activated during the whole S-phase as exponentially growing cells were used. If there is existing variation between the origins activated in a given cell relative to another in the same growing cell population, all the potential replication initiation sites will be scored. In such conditions, the Inventors scored 146700 potential origins per genome, similar for the both mouse pluripotent cell types (FIG. 1b, but MEF cells display significantly less origins, 84800 potential origins per genome (FIG. Ib, and this is associated with an increase in origin length. 60.2% MEF origins were also observed in the two pluripotent cell lines cell lines. Replication origins of *Drosophila* cells display the same length than MEF cells (4303 bp versus 4480 b) but with density higher than mouse cells (see later).

Figure 1A:
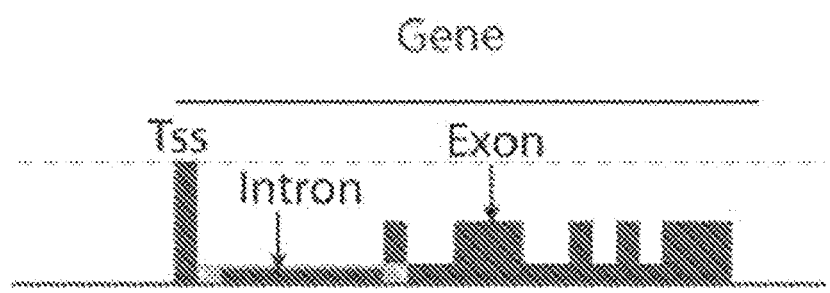
Figure 1B:
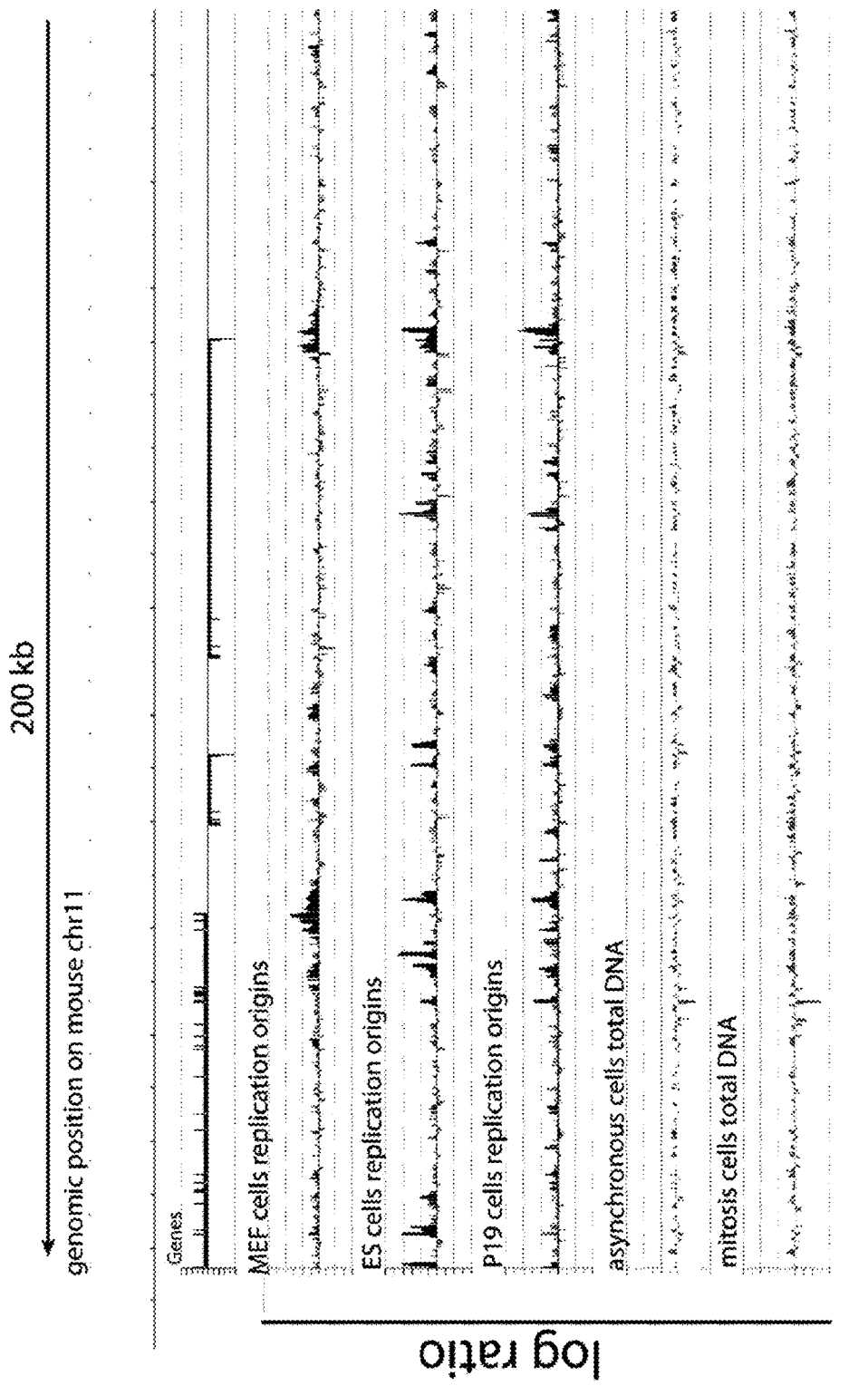
Figure 1C:
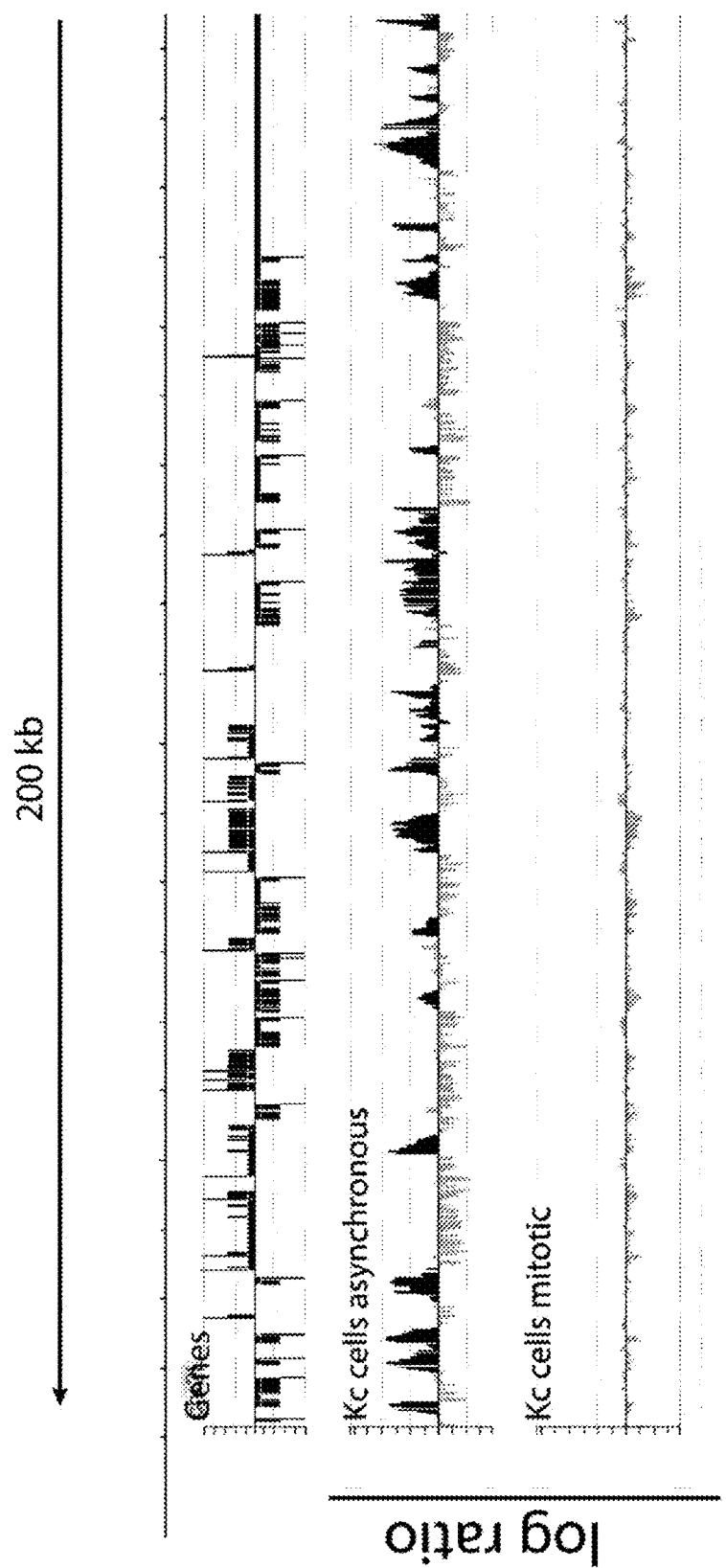
Figure 1D:
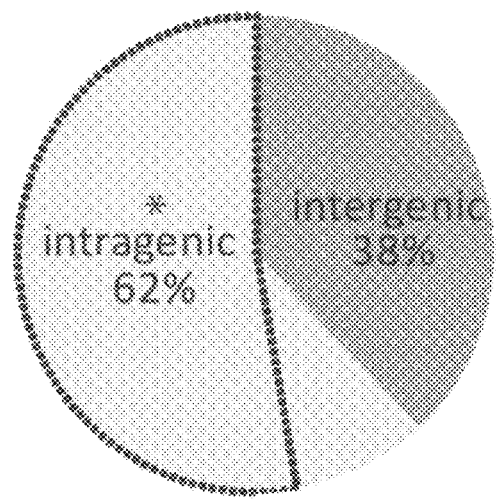
Figure 1E:
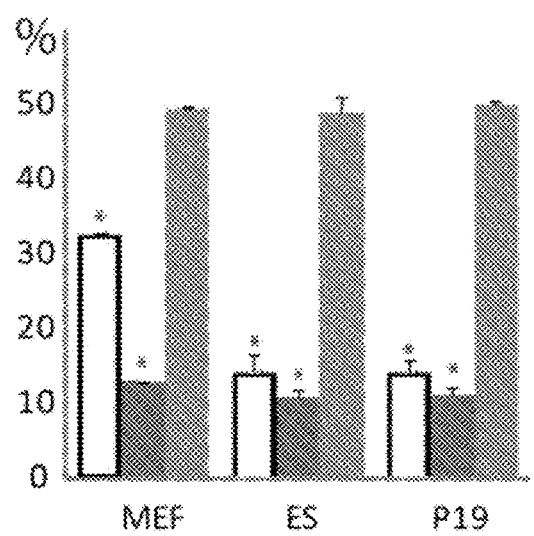
Figure 1F:
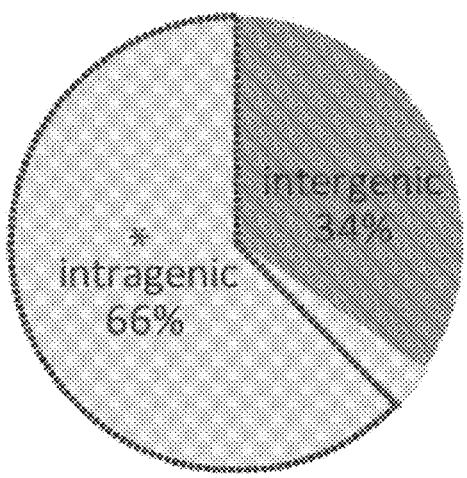
Figure 1G:
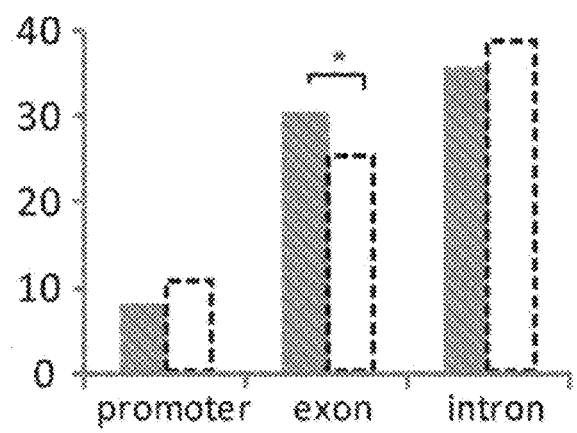
Figure 1H:
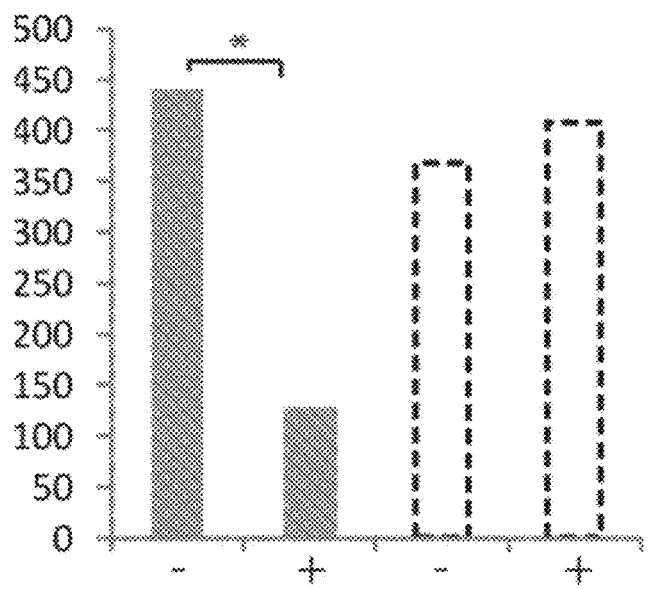
Figure 1I:
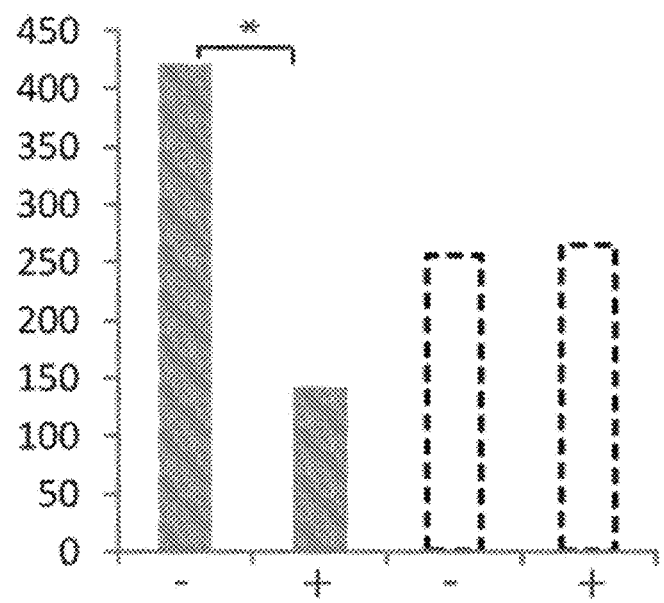

With regard to genes, mouse replications origins were found to be significantly associated with genes (p<0.001; FIG. ID). More particularly, origins overlap significantly (p<0.001) promoter and exonic sequences in all murine cell types (FIG. IE). *Drosophila* origins were found associated significantly with exonic sequences (FIG. 1G). Highly transcribed genes are enriched in replication origins, suggesting that transcription may facilitate origin specification and/or firing (FIGS. IH and 11).

Replication Origins are Determinate by CpG Island-Like Regions

Given their association with transcriptional units and with promoter regions, the Inventors examined the distribution of replication origins around the transcription start sites (TSS) in mouse cells. Overall, TSS are highly associated with nascent strands signals (FIGS. 2A, 10A and 10E). Strikingly, the Inventors observed a strong bimodal distribution around the TSS, with a low probability to get nascent strands overlapping the TSS, whereas the two borders were enriched. This suggests that, at these DNA replication origins, two nascent strands initiation sites are used, bordering the TSS. A possible explanation was that a genetic element at the TSS was not itself used as a DNA synthesis site but driving initiation on its borders. In *Drosophila* cells, TSS are not enriched in origins, in contrast to mouse cells (FIG. 2E). In agreement, the Inventors did not observe the mouse bimodal distribution but detected an increase of origin density within gene as opposed to the promoter region (FIG. 2E).

Mammalian promoters and particularly from highly expressed genes are CpG-rich while genes highly regulated during development are often CpG-poor or free. CpG-rich sequences are known as CpG Islands (CGI). To better understand the bimodal distribution, the Inventors divided our analysis on TSS CpG-positive (n=820) and TSS CpG-free (n=434) separately. Notably, nascent strands specific signals are strongly associated with CGI-positive promoter while CG I-negative promoters are devoid of such signals in all three mouse cell lines (FIGS. 2B, 10B and 10F). The Inventors next looked at origins distribution around CGI. The Inventors found that replication origins are strongly associated with CGI in all mouse cell lines (FIGS. 2C, 2D, 10D and 10H). Moreover, origins distribution was also found to be bimodal around CGI (FIGS. 2H, 10C and 10G).

CGI are usually defined as regions of 200 pb min in length with 60% of CG-richness and a ratio of CpG observed/ CpG>0.6. Because cytosine methylation is almost inexistent in *drosophila melanogaster*, there is not a genome-wide bias toward eliminating CpG dinucleotides during evolution. The *drosophila* genome nevertheless contains region with identical properties as mammalian CGI. The Inventors delimitated these regions as CGI-like sequences. More of the half of CGI-like regions (54%) in *drosophila* cells and more than 70% of these sequences in mouse cells lines are associated with replication origin. These values drop to 32% and 43% for the randomized origins dataset. Moreover, the population of origins that is longer than average is even more associated with this sequence (82% in mice, FIGS. 2I and 2K). Altogether, the strong association of replication origins with CpG Island positive and highly transcribed genes may suggest that active genes are occupied by components from the pre-replicative complex.

The Inventors concluded that sequences related to CGI are determinant for localization of origins in mice as well as *drosophila*, regardless of their genomic position, e. g. not only in promoter region, consistent with presence of CGI-like sequences in exonic region from *drosophila* genome. These results also provide a novel possible function for CGI sequences conserved both in vertebrates and invertebrate species.

Nevertheless, CpG island rich sequences does not recognize the majority of replication origins (see FIGS. 2D, 10D and 10H). The Inventors conclude that replication origins might be specified by additional mechanisms, and the primary sequence was one possibility.

The Majority of Metazoan Replication Origin Shares a Common Motif

No consensus sequence is known to be associated with metazoan origins. Nevertheless, the Inventors hypothesized that such a sequence could potentially be identified in *drosophila* origins because of the compactness of the fly genome. As a first approach, fifteen 3 kb length origins sequence were submitted to the MEME server (http://meme.sdsc.edu/meme4 4 O/intro.html) using default settings. A repetitive 0-rich motif was found. When matched on the *drosophila* genome, this motif detected a large (>50%) proportion of replication origins. Several rounds of optimization gave rise to a repeated 0-rich sequence that contained G every three nucleotides along the repeat (FIG. 3A). Because of its unique ability to detect Oris (see below) and of its repetitive nature, this motif was dubbed ORE for Origin Repeated Element. When the Inventors looked for the occurrence of this motif genome-wide (using FIMO server; http://meme.sdsc.edu/meme/fimo-intro.html), the Inventors found that it had good predictive value as it was associated to more than two thirds of the origins (FIG. 3B). In contrast, changing the nucleotide position in the motif results in poor origins prediction, indicating that the primary sequence, and not only QC-content, was essential (FIGS. 3B and 3C). Interestingly, the repeat number influenced Ori prediction: increasing the number of repeats in ORE significantly improved prediction, whereas decreasing the repeat number lowered it. Cumulative origins signals associated with the motif again revealed a bimodal distribution, similarly to CGI-like domain, but the motif detects more origins than these domains (FIG. 3D). Moreover, the Inventors observed that NS signal associated with ORE was asymmetric, being more enriched at the 3'. The Inventors further observed that the motif found in *drosophila* cells was efficient for detecting the majority of replication origins mapped in MEF, ES and P19 cells (FIGS. 3E and 3F). Permuting the motif position again strongly reduces origin coverage by the motif, confirming that the primary sequence of the motif was important. Nascent Strands signals around ORE showed an asymmetric bimodal distribution, like in *drosophila* cells (FIG. 3G). Finally the Inventors found that ORE was present in the majority of the previously characterized Oris. The ORE has a significant predictive power. Indeed, also two thirds of all ORE occurrences mapped very close to replication origins in *drosophila* cells. In mammals, the ORE is less efficient, but nevertheless it is one order of magnitude more predictive than the 3.3% predictive value of the ACS element in budding yeast. Altogether, these results suggest that metazoan replication origins display a conserved element which might be involved either for origin specification and/or origin activation/firing.

Hieratical Organization of Replication Origins in Metazoan

Genome-wide data permit to identify sites which can serve as DNA replication origins, but do not permit to have a view of origin usage along individual DNA molecules. Analysis at the single molecule level can be performed by DNA combing, where replicating DNA is labeled with pulses of modified nucleotide in vivo, and high molecular weight then stretched at a constant rate onto a slide. This method allows the precise determination of replication speed and inter-origin distances (FIG. 4). MEFs, ES and P 19 cells replicate their DNA with a similar fork speed of 1.5 kb/min, similar to rates observed in human cells. *Drosophila* cells exhibit a nearly two-fold slower fork (0.8 kb/min), possibly due to the lower.

Sequential dual nucleotide labeling to determinate fork direction and bi-directional origins of replication was performed. The Inventors observed a near two-fold difference in inter-origin distances between mouse cells (139 kb) and *drosophila* cells (73 kb) (FIG. 4A-D). The smaller inter-origin distance in Kc cells might be a consequence of the more compact *drosophila* genome. Of note, pluripotent or differentiated mouse cells have similar inter-origins spacing even though they differ in cell cycle profile and origin repertoire.

If all mapped origins were activated (firing efficiency of 100%) the resulting very short inter-origin distance distribution would be significantly different from the distribution observed by DNA combing (FIGS. 4E and 4F). As exemplified by MEF cells, the origin density of all potential origins was 4.3 fold higher than the density observed by DNA combing; indicating that 1 in every 4.3 origins on average is fired in individual DNA molecules (firing efficiency of ~23%). Our results both in *Drosophila* and mouse cells are consistent with the findings that metazoan origins, like yeast Oris [Heichinger C, et al. *EMBO J* 2006 Nov. 1; 25(21):5171-9], are redundant and that only a small proportion of them is effectively used at each cell cycle. The Inventors next wanted to model genome-wide origin usage in MEF cells to recapitulate the origins firing pattern observed in single cell. The Inventors first tested the possibility that origins were fired purely stochastically (FIG. 4G). Using a firing efficiency of 23%, the mean inter-origin distances of randomly fired Oris was identical to the value obtained by DNA combing. However the simulated inter-origin distance distribution was significantly different from the distribution obtained in combing experiments (FIG. 4J). The purely stochastic distribution was characterized by populations of short and long inter-origin distances not observed in combing experiments (arrows in FIG. 4H). The group of large inter-origin distances was in agreement with the random gap problem, with the consequence that too large replicons could not completely replicate and that a large number of gaps of unreplicated DNA would persist at the end of S phase [Hyrien O, et al. *Bioessays*. 2003 February, 25(2):116-25; Laskey R A. *J Embryol Exp Morphol*. 1985 November, •89 *Suppl*:285-96]. In the second model that the Inventors called the hierarchical stochastic model, groups of adjacent origins are functionally linked together into domains over a defined distance that defines the replicon, where activation of one origin silences the others (FIG. 4H). Origins were thus grouped, taking into account their distribution along the genome, and one single Ori per domain was allowed to fire randomly. Strikingly, the simulated inter-origin distances were significantly similar to the combing data (FIG. 4L). Importantly, the hierarchical stochastic model was also functional in ES and in Kc cells (FIG. 4I, 4K and data not shown). This model requires optimization of the clustering parameters (the average size of the cluster). Nevertheless, the model is thus robust and can accommodate changes in origin density and firing efficiency. Overall, these data suggest that DNA replication origins are in large excess in metazoans and have a flexible use. Metazoan replicons appear constituted of groups of potential and flexible adjacent origins where activation of one origin suppresses the surrounding ones.

Density of Replication Origins in Chromosome 11

DNA replication origins are often synchronously activated in clusters. The Inventors looked at the origins density on areas of 70 Kb in mice and 50 Kb in *Drosophila* through a sliding window every 1 O bp. First, the Inventors observed that zones of high density of origins were at similar positions along chromosome 11, for all three mouse cells lines (FIG. SA). Then, the Inventors compared these areas with other genomic features such as density in genes, promoter and CpG islands. For example, the areas of density origins coincide well with areas of density of CpG islands in MEF cells (FIG. SA). A similar trend was observed for ES and P19 cells (data not shown). These data confirm that CpG islands are key to locate and/or fire replication origins. The replication timing of different ESC cells was recently published, and showed a very high conservation profile between distantly related pluripotent cells. The early regions were significantly associated with both a higher transcription level and a greater content in GC-rich sequences. The Inventors observed a strong correlation between early replicated regions and areas of high origins density in ES and P19 cells (FIG. 5A). In MEFs, the Inventors also observed a strong correlation between early replicated regions and areas of high origins density (FIG. 5A). For example, a 3.5 Mb early replicating domain is enriched in replication origins in all mouse cell lines tested (FIG. 5B). This region is also rich in CpG Island, promoter and genes. In a late replicating part of chromosome 11, pluripotent cells display low density replication origins (FIG. SC). However, MEP show strong origin activity, suggesting that this region could replicate early in this cell type. Similar, but albeit weaker, trends where observed for *drosophila* replication origins (data not shown).

The inventors thus propose that a replication cluster includes consecutive groups of adjacent flexible Oris, each set constituting a replicon, that are activated synchronously (see FIG. 4H). The selection of a given Ori within each replicon might be achieved through several mechanisms. Selection itself might depend on the cell fate or the organization of the chromatin domain. The Ori interference mechanism has been described in yeast [Brewer and Fangman, *Science*. 1993 Dec. 10; 262(5140):1728-31; Lebofsky R, et al. *Mol Biol Cell*. 2006 December; 17(12):5337-45] where firing at one Ori inhibits close-by Oris and this phenomenon could lead to the 100-120 Kbp average size of the replicon.

Alternatively, control elements or chromosome organization might control firing in the cluster. For example, activation of one Ori might promote looping out of the replicon and silencing of the other potential Oris. The CpG Islands seems to be a putative control element for origin organization (FIG. 5D).

Example 4: Nucleic Acid Molecules Containing Ogre are Able to Replicate Themselves Based on an Epstein Barr Virus (EBV) derived plasmid (called DeltaDS) which is deleted for the viral replication origin (the Dyad Symmetry (DS) sequence), the inventors have tested the efficiency of a replication origin according to the invention, said replication origin as set forth in SEQ ID NO: 33 (WT OGRE), correspond to a replication origin of the mouse cc2 gene and contains the sequence GGGGGCGGG.

For validation, the WT OGRE has been, either deleted to suppress the ORE (Delta ORE as set forth in SEQ ID NO: 34, or the ORE was randomly modified (ModORE as set forth in SEQ ID NO: 35. The sequences are shown hereafter:

```
1 - WT OGRE - SEQ ID NO: 34 (the 3 repeated ORE
are underlined)
AAACACGGGAAGCACTTGAAACAATTTCTAGTCTTTATGGTGGCATCTGG
GTCGACCACAGACCTAGCACACAGTAGGGGCGCAGGCTAGACGAGGCAGA
AGGCCGCAGCGAAGAGACTACGAGAAAGACAGGGGCCCGCAGGGAGACCG
CGGAGATCTCCGGCGTCCTTCCGGGAGCAGCCCAGCCCAACGCCGCAGCT
GTCAGGCCGCGGGCGGCGGCGCCAGTCCACCAAACCTGAAAGTTCCATCC
CAGCGCCTCCACCTTCCCAGCCTGGACAAGTTACCTTGCGCCCGCTGCTC
CCGGTCCCGCCCCCGTCATCCATTGGTCGACGGGTTTCTTTGTTAGCAGG
AGCGTGCGGGTGCCATTGGCTCGCGGGGCTGCCGGTTGCGGTGCCCCGCC
CCACCCCGCCCCTCCCCGAGTGCGCGCGGCGCCCAGCTCGGTTCGTTCGC
GGTGGCGGCGGGCGCCGGGTGAGCGCGACGGCTGGACTTGCCGGCCGGCG
CCTTGGGGGCGGCCGCGGTGGAGCCAGCGGCCGGAGGCCGCGTCCGTCCA
TGGGCCCACAGCGGCCGGGCGGCGGGGCGGGGCGCGAGGCGGCGCGCGCG
CTCTGAGGCCGCGGCGAGCAGGCGGGGCGCGGCGCGAGAGGGGAGGCCTT
TCCGGGCCTGCGGCGGCCAGCGCAAAATGCGGCGGCGGCCGCGCTGAGTC
CCCGACCCCCGGGAGAGCGCTGGGCCGTGGCGGCCCGCTCCGCGGCCGCC
TAGCCGACATGTCGGCGGCCAAGGAAAACCCGTGCAGGAAATTTCAGGCC
AACATCTTCAACAAGAGCAAGTGTCAGAACTGCTTCAAGCCCCGCGAGTC
GCATCTGCTCAACGACGAGGACCTGACGCAGGTGAGCTGCCGCGGGTGCG
GAGCTGAGAGTCCTGCCTGCGAGTCGTGCCGGGGAGCGCAGAGCCTGCGA
AGGCCAAGAGAGAATAAAAATGGAGCAGGGAAAAAAAATGCGTGAGAGTT
GGGGGATGGGGTTGGAATGGGGGCGGGAAGAGTATCGATAGAGCTGGGAC
AAAGGGAAAATCCTCAAGAATGCCGAAAAATAACATCCTTTCCCGTTCCC
ATAGCTCTGCCGTGTGATTCATGCTTGTTGGGTGACTCAAAAAAATGTCT
GGTTTCCCTGGATAGGAACAAAGTGGGGCTTGCTTGCCACTTGTCAGTAC
TACCCCCCCCCTCGCCCCCCTCGCGACTTGTCTTGGGACTGGACGCAGAC
TTGGCCACCAAACTGTCCCAGGAATTGGCATGTTTGCGTGGGTCACCAGT
TTCCATCTTGTGGAATAGAGCCTGCTCTCCTTCTAAGTCACTGTCACCGT
CAGGGTCTGAAGAGAGATGAGGTGTTTCTCTTCAGATGGGTGGGTCTTGC
TCTTGAACTGAAGGTAGGAATAGCTTTTGTCGAGGGGTAGGGGCTTCCCT
TCTTGGTTTTGCTTTCTGGCCCAGGAGACCAAGAAGACCTGTACATTCTG
GGGAAAGTTGGTTTCCCCCTCTGTCTGCCCTTAATTTGTTAGTCAGGATT
TTGGACCAGGTTAGACGCTCTTCCTAACCCGTGTCAAAGTCACAGTCATG
GAAAACAGAGTTCCAGACCTCCAAGTCACAGTCATGGAAAACATTGTCCT
AGATTGCCAAAGACCTCCAACCCCGGAGCAGTGTAGGAGATTGGGAATTT
GTGTTGGTACAAGGTCTCCAATTTGGGCAACTGGCCCTTGGGAACTGGTT
GCTCTCCCGTTTCTGGTGTTGAGGATTCCTGGCCTTGTTTGCAGCACTTT
GGGAAAGCACTATATATCCTGCTCCCCTTTCCCCTCGCCCACTTCCTTTG
CCCCCTGCTTGCTGACTTCAGTGGAGTTCCCCACACGGTCCAGCCAGTGC
CACCTAGTTGTAGCCACTCCTTTTGGAAAGAGCTGTTTAGACTGAAAACA
TTGCTTTGAAGTGCCCTGGTTTGGCTGTTTTTAAAGCCTTTATGGGCAAG
C 2 - Delta OGRE - SEQ ID NO: 35 (the deletion
including the 3 ORE is shown
(in italic bold underlined)
AAACACGGGAAGCACTTGAAACAATTTCTAGTCTTTATGGTGGCATCTGG
GTCGACCACAGACCTAGCACACAGTAGGGGCGCAGGCTAGACGAGGCAGA
AGGCCGCAGCGAAGAGACTACGAGAAAGACAGGGGCCCGCAGGGAGACCG
CGGAGATCTCCGGCGTCCTTCCGGGAGCAGCCCAGCCCAACGCCGCAGCT
GTCAGGCCGCGGGCGGCGGCGCCAGTCCACCAAACCTGAAAGTTCCATCC
CAGCGCCTCCACCTTCCCAGCCTGGACAAGTTACCTTGCGCCCGCTGCTC
CCGGTCCCGCCCCCGTCATCCATTGGTCGACGGGTTTCTTTGTTAGCAGG
AGCGTGCGGGTGCCATTGGCTCGCGGGGCTGCCGGTTGCGGTGCCCCGCC
CCACCCCGCCCCTCCCCGAGTGCGCGCGGCGCCCAGCTCGGTTCGTTCGC
GGTGGCGGCGGGCGCCGGGTGAGCGCGACGGCTGGACTTGCCGGCCGGCG
CCTTGGGGGCGGCCGCGGTGGAGCCAGCGGCCGGAGGCCGCGTCCGTCCA
TGGGCCCACAGCGGCCGGGCGGCGGGGCGGGGCGCGAGGCGGCGCGCGCG
CTCTGAGGCCGCGGCGAGCAGGCGGGGCGCGGCGCGAGAGGGGAGGCCTT
TCCGGGCCTGCGGCGGCCAGCGCAAAATGCGGCGGCGGCCGCGCTGAGTC
CCCGACCCCCGGGAGAGCGCTGGGCCGTGGCGGCCCGCTCCGCGGCCGCC
TAGCCGACATGTCGGCGGCCAAGGAAAACCCGTGCAGGAAATTTCAGGCC
AACATCTTCAACAAGAGCAAGTGTCAGAACTGCTTCAAGCCCCGCGAGTC
GCATCTGCTCAACGACGAGGACCTGACGCAGGTGAGCTGCCGCGGGTGCG
GAGCTGAGAGTCCTGCCTGCGAGTCGTGCCGGGGAGCGCAGAGCCTGCGA
AGGCCAAGAGAGAATAAAAATGGAGCAGGGAAAAAAAATGCG
( TGAGAGTTGGGGGATGGGGTTGGAATGGGGGCGGGG )AA
GAGTATCGATAGAGCTGGGACAAAGGGAAAATCCTCAAGAATGCCGAAAA
ATAACATCCTTTCCCGTTCCCATAGCTCTGCCGTGTGATTCATGCTTGTT
GGGTGACTCAAAAAAATGTCTGGTTTCCCTGGATAGGAACAAAGTGGGGC
```

```
TTGCTTGCCACTTGTCAGTACTACCCCCCCCCTCGCCCCCCTCGCGACTT

GTCTTGGGACTGGACGCAGACTTGGCCACCAAACTGTCCCAGGAATTGGC

ATGTTTGCGTGGGTCACCAGTTTCCATCTTGTGGAATAGAGCCTGCTCTC

CTTCTAAGTCACTGTCACCGTCAGGGTCTGAAGAGAGATGAGGTGTTTCT

CTTCAGATGGGTGGGTCTTGCTCTTGAACTGAAGGTAGGAATAGCTTTTG

TCGAGGGGTAGGGGCTTCCCTTCTTGGTTTTGCTTTCTGGCCCAGGAGAC

CAAGAAGACCTGTACATTCTGGGGAAAGTTGGTTTCCCCCTCTGTCTGCC

CTTAATTTGTTAGTCAGGATTTTGGACCAGGTTAGACGCTCTTCCTAACC

CGTGTCAAAGTCACAGTCATGGAAAACAGAGTTCCAGACCTCCAAGTCAC

AGTCATGGAAAACATTGTCCTAGATTGCCAAAGACCTCCAACCCCGGAGC

AGTGTAGGAGATTGGGAATTTGTGTTGGTACAAGGTCTCCAATTTGGGCA

ACTGGCCCTTGGGAACTGGTTGCTCTCCCGTTTCTGGTGTTGAGGATTCC

TGGCCTTGTTTGCAGCACTTTGGGAAAGCACTATATATCCTGCTCCCCTT

TCCCCTCGCCCACTTCCTTTGCCCCCTGCTTGCTGACTTCAGTGGAGTTC

CCCACACGGTCCAGCCAGTGCCACCTAGTTGTAGCCACTCCTTTTGGAAA

GAGCTGTTTAGACTGAAAACATTGCTTTGAAGTGCCCTGGTTTGGCTGTT

TTTAAAGCCTTTATGGGCAAGC
```

3 - Random OGRE - SEQ ID NO: 36 (the 3 random
ORE are underlined)
```
AAACACGGGAAGCACTTGAAACAATTTCTAGTCTTTATGGTGGCATCTGG

GTCGACCACAGACCTAGCACACAGTAGGGGCGCAGGCTAGACGAGGCAGA

AGGCCGCAGCGAAGAGACTACGAGAAAGACAGGGGCCCGCAGGGAGACCG

CGGAGATCTCCGGCGTCCTTCCGGGAGCAGCCCAGCCCAACGCCGCAGCT

GTCAGGCCGCGGCGGCGGCGCCAGTCCACCAAACCTGAAAGTTCCATCC

CAGCGCCTCCACCTTCCCAGCCTGGACAAGTTACCTTGCGCCCGCTGCTC

CCGGTCCCGCCCCCGTCATCCATTGGTCGACGGGTTTCTTTGTTAGCAGG

AGCGTGCGGGTGCCATTGGCTCGCGGGGCTGCCGGTTGCGGTGCCCCGCC

CCACCCCGCCCCTCCCCGAGTGCGCGCGGCGCCCAGCTCGGTTCGTTCGC

GGTGGCGGCGGGCGCCGGGTGAGCGCGACGGCTGGACTTGCCGGCCGGCG

CCTTGGGGGCGGCCGCGGTGGAGCCAGCGGCCGGAGGCCGCGTCCGTCCA

TGGGCCCACAGCGGCCGGGCGGCGGGCGGGGCGCGAGGCGGCGCGCGCG

CTCTGAGGCCGCGGCGAGCAGGCGGGGCGCGGCGCGAGAGGGGAGGCCTT

TCCGGGCCTGCGGCGGCCAGCGCAAAATGCGGCGGCGGCCGCGCTGAGTC

CCCGACCCCCGGGAGAGCGCTGGGCCGTGCCGGCCCGCTCCGCGGCCGCC

TAGCCGACATGTCGGCGGCCAAGGAAAACCCGTGCAGGAAATTTCAGGCC

AACATCTTCAACAAGAGCAAGTGTCAGAACTGCTTCAAGCCCGCGAGTC

GCATCTGCTCAACGACGAGGACCTGACGCAGGTGAGCTGCCGCGGGTGCG

GAGCTGAGAGTCCTGCCTGCGAGTCGTGCCGGGGAGCGCAGAGCCTGCGA

AGGCCAAGAGAGAATAAAAATGGAGCAGGGAAAAAAAATGCGTGAGAGTT

GCTCGCGCACCGGTGTGAGCTCCTGCCAAGAGTATCGATAGAGCTGGGAC

AAAGGGAAAATCCTCAAGAATGCCGAAAAATAACATCCTTTCCCGTTCCC
```

```
ATAGCTCTGCCGTGTGATTCATGCTTGTTGGGTGACTCAAAAAAATGTCT

GGTTTCCCTGGATAGGAACAAAGTGGGGCTTGCTTGCCACTTGTCAGTAC

TACCCCCCCCCTCGCCCCCCTCGCGACTTGTCTTGGGACTGGACGCAGAC

TTGGCCACCAAACTGTCCCAGGAATTGGCATGTTTGCGTGGGTCACCAGT

TTCCATCTTGTGGAATAGAGCCTGCTCTCCTTCTAAGTCACTGTCACCGT

CAGGGTCTGAAGAGAGATGAGGTGTTTCTCTTCAGATGGGTGGGTCTTGC

TCTTGAACTGAAGGTAGGAATAGCTTTTGTCGAGGGGTAGGGGCTTCCCT

TCTTGGTTTTGCTTTCTGGCCCAGGAGACCAAGAAGACCTGTACATTCTG

GGGAAAGTTGGTTTCCCCCTCTGTCTGCCCTTAATTTGTTAGTCAGGATT

TTGGACCAGGTTAGACGCTCTTCCTAACCCGTGTCAAAGTCACAGTCATG

GAAAACAGAGTTCCAGACCTCCAAGTCACAGTCATGGAAAACATTGTCCT

AGATTGCCAAAGACCTCCAACCCCGGAGCAGTGTAGGAGATTGGGAATTT

GTGTTGGTACAAGGTCTCCAATTTGGGCAACTGGCCCTTGGGAACTGGTT

GCTCTCCCGTTTCTGGTGTTGAGGATTCCTGGCCTTGTTTGCAGCACTTT

GGGAAAGCACTATATATCCTGCTCCCCTTTCCCCTCGCCCACTTCCTTTG

CCCCCTGCTTGCTGACTTCAGTGGAGTTCCCCACACGGTCCAGCCAGTGC

CACCTAGTTGTAGCCACTCCTTTTGGAAAGAGCTGTTTAGACTGAAAACA

TTGCTTTGAAGTGCCCTGGTTTGGCTGTTTTTAAAGCCTTTATGGGCAAG

C
```

OriP, a replication origin of a virus and the origin of the c-myc gene are used as controls. The vector also contains Family of Repeats (FR) sequences important for episomal mitotic segregation. The viral factor EBNA1 binds the FR sequence and is required for tethering the plasmid to the mitotic chromosome.

DeltaDS vectors harboring the tested origin sequences are transfected in human embryonic kidney (HEK) 293 cells stably expressing EBNA1 to allow mitotic segregation of the episome. Five days later, episome (i.e. low molecular weight DNA) is recovered from transfected cells (Hirt lysis). The plasmids are then subjected to DpnI digestion. The restriction enzyme DpnI is sensitive to Dam methylation and cuts only fully (i.e. on both strands) methylated DNA. As Dam methylation occurs in E. coli (from which the plasmid was produced) but not in eukaryotes, semi-conservative episomal replication will result in the loss of the methylation mark.

DpnI-resistance thus reflects episomal replication. DpnI-treated plasmids are then electroporated into high transformation efficiency E. coli and plated on antibiotics LB-plates. The number of colonies is proportional to the amount of DpnI-resistant plasmid, which is a measure of episomal replication.

Procedure is illustrated in FIG. 13A

The results are shown in FIG. 13B.

The tested origin (WT OGRE) is more efficient for DNA replication than the c-myc origin. It is to be noticed that the modified OGRE element (either by deletion or by randomization) significantly impairs the replication ability of the tested origin.

These data confirm that a vector according to the invention is able to self-replicate in metazoan cells.

Similar results are obtained with a replication origin from the mouse cc4 gene.

Example 5: Deletions of the G4 Element in the OGRE Motifs Strongly Affects DNA Replication Origin Activity The genomic DNA of NIH 3T3 cells was modified using Cas9 nickase that was guided by two gRNAs specific to G rich regions in 2 origins of replication identified by the inventors on mouse chomosome 11. The G rich sequences of origin cc2 and cc4 are as follow, GGGGGATGGGGTTG-GAATGGGGGCGGG SEQ ID NO: 33 and GGGGGCGGGAGGGAAGGGGG SEQ ID NO: 32 and they were predicted to a forma G-quadruplex structure with a high probability.

The introduced mutation led to deletion of 9 to 15 nucleotides from the G4-forming sequence in each allele of cc4 origin, generating cc4 G4−/−cell line, and in one allele of cc2 origin, generating cc2 G4+/−cell line.

The replication activity of selected origins in newly created cell lines was tested by DNA nascent strand purification (as described above) and quantified by qPCR using origin-specific primers. The primer's position is shown on the enclosed FIG. 14.

The quality of DNA nascent strand purification experiment was determined using primers specific to the well described c-Myc origin (placed on chromosome 15) and to a negative region downstream to c-Myc origin.

The parental cell line was used to determine the basal level of enrichment in nascent DNA strands for tested origins.

Two known origins (CC2 and CC4) were selected, which contain OGRE/G4 elements. Using the CRISPR/Cas method, the inventors have deleted G4 elements and analysed the replication origin activity at the corresponding loci as well as in known control regions containing (Myc 2) or not containing an origin ((Myc 12). The analysis of replication origin activity was performed by the purification of nascent strands, followed by qPCR analysis.

The region analyzed is indicated below each FIGS. 14A and B, with the position of the G4 that is deleted as well as the positions of the primers used for the qPCR reaction.

The FIGS. 14A and B show that deletions in the G4 elements strongly decrease the replication origin activity of the loccus. The controls show that an external region without replication origin (Myc 12) is not affected and an external region containing an origin (Myc2) remains also unaffected.

These experiments show that the G4 elements are essentials for the activation of the replication origins.

These experiments were made in collaboration with the team of Aloys Schepers, Research Unit Gene Vectors, Marchioninistr. 25, 81377 Munchen, Germany.

---

The invention claimed is:

1. A method for initiating the replication of a double stranded deoxyribonucleic acid (DNA) molecule in a pluricellular eukaryotic cell, said method comprising:

inserting into said DNA molecule at least one multicellular DNA replication origin, the replication origin comprising at least one of the following sequences:

GGGGGCGGGGAGGGAAGGGGG,  (SEQ ID NO: 32)
and
GGGGGATGGGGTTGGAATGGGGCGGG;  (SEQ ID NO: 33)

introducing said DNA molecule comprising the inserted DNA replication origin into the pluricellular eukaryotic cell; and then
identifying the nascent DNA synthesized from the inserted DNA replication origin, the nascent DNA identifying the initiation of the replication, wherein replication of the DNA molecule comprising the DNA replication origin within the pluricellular eukaryotic cell is initiated by the presence of said replication origin.

2. The method according to claim 1, wherein the G/C ratio in the at least one multicellular DNA replication origin is greater than 1.

3. A process for preparing a recombinant non-naturally occurring double stranded circular DNA vector comprising at least one multicellular DNA replication origin as the unique means for replicating the vector in a pluricellular eukaryotic cell or cell extract, said process comprising:

inserting into a vector at least one multicellular DNA replication origin, the replication origin comprising at least one of the following sequences:

GGGGGCGGGGAGGGAAGGGGG,  (SEQ ID NO: 32)
and
GGGGGATGGGGTTGGAATGGGGCGGG;  (SEQ ID NO: 33)

introducing said DNA molecule comprising the inserted DNA replication origin into the pluricellular eukaryotic cell; and then
recovering the replicated vectors;
wherein the inserted at least one multicellular DNA replication origin is originated from a nucleic acid molecule, the nucleic acid molecule being absent in the vector before its insertion, and
wherein the inserted at least one multicellular DNA replication origin allows said DNA vector to self-replicate in a pluricellular eukaryotic cell or cell extract.

4. The method according to claim 3, wherein the G/C ratio in the at least one multicellular DNA replication origin is greater than 1.

* * * * *

SEQUENCE LISTING

```
<160> NUMBER OF SEQ ID NOS: 36

<210> SEQ ID NO 1
<211> LENGTH: 7
<212> TYPE: DNA
<213> ORGANISM: Artificial sequence
<220> FEATURE:
<223> OTHER INFORMATION: eukaryote replication origin
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: N= G or A
<220> FEATURE:
<221> NAME/KEY: misc_feature
<222> LOCATION: (5)..(5)
<223> OTHER INFORMATION: N= T or C
<220> FEATURE:
<221> NAME/KEY: misc_feature
<222> LOCATION: (6)..(7)
<223> OTHER INFORMATION: n is a, c, g, or t

<400> SEQUENCE: 1 nngnnnn                                                              7

<210> SEQ ID NO 2
<211> LENGTH: 7
<212> TYPE: DNA
<213> ORGANISM: Artificial sequence
<220> FEATURE:
<223> OTHER INFORMATION: eukaryote replication origin
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: N= T or G
<220> FEATURE:
<221> NAME/KEY: misc_feature
<222> LOCATION: (5)..(5)
```

```
<223> OTHER INFORMATION: N= G or C
<220> FEATURE:
<221> NAME/KEY: misc_feature
<222> LOCATION: (6)..(7)
<223> OTHER INFORMATION: n is a, c, g, or t

<400> SEQUENCE: 2 nnngnnn                                                                   7

<210> SEQ ID NO 3
<211> LENGTH: 7
<212> TYPE: DNA
<213> ORGANISM: Artificial sequence
<220> FEATURE:
<223> OTHER INFORMATION: eukaryote replication origin
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: N= G or C
<220> FEATURE:
<221> NAME/KEY: misc_feature
<222> LOCATION: (4)..(4)
<223> OTHER INFORMATION: N= T or A
<220> FEATURE:
<221> NAME/KEY: misc_feature
<222> LOCATION: (6)..(7)
<223> OTHER INFORMATION: n is a, c, g, or t

<400> SEQUENCE: 3 nnnngnn                                                                   7

<210> SEQ ID NO 4
<211> LENGTH: 21
<212> TYPE: DNA
<213> ORGANISM: Artificial sequence
<220> FEATURE:
<223> OTHER INFORMATION: eukaryote replication origin

<400> SEQUENCE: 4
shgcygsygg mgcygshgst g                                                  21

<210> SEQ ID NO 5
<211> LENGTH: 21
<212> TYPE: DNA
<213> ORGANISM: Artificial sequence
<220> FEATURE:
<223> OTHER INFORMATION: eukaryote replication origin

<400> SEQUENCE: 5
ckgykgckgc dgckgcdgyk g                                                  21

<210> SEQ ID NO 6
<211> LENGTH: 13
<212> TYPE: DNA
<213> ORGANISM: Artificial sequence
<220> FEATURE:
<223> OTHER INFORMATION: eukaryote replication origin

<400> SEQUENCE: 6
gtcccagtcc cag                                                           13

<210> SEQ ID NO 7
<211> LENGTH: 13
<212> TYPE: DNA
<213> ORGANISM: Artificial sequence
```

```
<220> FEATURE:
<223> OTHER INFORMATION: eukaryote replication origin

<400> SEQUENCE: 7
tgctgctgct gct                                                          13

<210> SEQ ID NO 8
<211> LENGTH: 13
<212> TYPE: DNA
<213> ORGANISM: Artificial sequence
<220> FEATURE:
<223> OTHER INFORMATION: eukaryote replication origin

<400> SEQUENCE: 8
tatatatata tat                                                          13

<210> SEQ ID NO 9
<211> LENGTH: 13
<212> TYPE: DNA
<213> ORGANISM: Artificial sequence
<220> FEATURE:
<223> OTHER INFORMATION: eukaryote replication origin

<400> SEQUENCE: 9
agcagcagca gca                                                          13

<210> SEQ ID NO 10
<211> LENGTH: 13
<212> TYPE: DNA
<213> ORGANISM: Artificial sequence
<220> FEATURE:
<223> OTHER INFORMATION: eukaryote replication origin

<400> SEQUENCE: 10
gttgctgctg ctg                                                          13

<210> SEQ ID NO 11
<211> LENGTH: 13
<212> TYPE: DNA
<213> ORGANISM: Artificial sequence
<220> FEATURE:
<223> OTHER INFORMATION: eukaryote replication origin

<400> SEQUENCE: 11
tcagacatct tag                                                          13

<210> SEQ ID NO 12
<211> LENGTH: 13
<212> TYPE: DNA
<213> ORGANISM: Artificial sequence
<220> FEATURE:
<223> OTHER INFORMATION: eukaryote replication origin

<400> SEQUENCE: 12
agcagcagca aca                                                          13

<210> SEQ ID NO 13
<211> LENGTH: 13
<212> TYPE: DNA
<213> ORGANISM: Artificial sequence
<220> FEATURE:
<223> OTHER INFORMATION: eukaryote replication origin

<400> SEQUENCE: 13
cagacatctt agg                                                          13
```

```
<210> SEQ ID NO 14
<211> LENGTH: 13
<212> TYPE: DNA
<213> ORGANISM: Artificial sequence
<220> FEATURE:
<223> OTHER INFORMATION: eukaryote replication origin

<400> SEQUENCE: 14
agacatctta ggc                                                          13

<210> SEQ ID NO 15
<211> LENGTH: 13
<212> TYPE: DNA
<213> ORGANISM: Artificial sequence
<220> FEATURE:
<223> OTHER INFORMATION: eukaryote replication origin

<400> SEQUENCE: 15
cagcagcagc agc                                                          13

<210> SEQ ID NO 16
<211> LENGTH: 13
<212> TYPE: DNA
<213> ORGANISM: Artificial sequence
<220> FEATURE:
<223> OTHER INFORMATION: eukaryote replication origin

<400> SEQUENCE: 16
taacgtgtgg tga                                                          13

<210> SEQ ID NO 17
<211> LENGTH: 13
<212> TYPE: DNA
<213> ORGANISM: Artificial sequence
<220> FEATURE:
<223> OTHER INFORMATION: eukaryote replication origin

<400> SEQUENCE: 17
tgttgctgct gct                                                          13

<210> SEQ ID NO 18
<211> LENGTH: 13
<212> TYPE: DNA
<213> ORGANISM: Artificial sequence
<220> FEATURE:
<223> OTHER INFORMATION: eukaryote replication origin

<400> SEQUENCE: 18
cagcagcagc aac                                                          13

<210> SEQ ID NO 19
<211> LENGTH: 9
<212> TYPE: DNA
<213> ORGANISM: Artificial sequence
<220> FEATURE:
<223> OTHER INFORMATION: eukaryote replication origin

<400> SEQUENCE: 19 tgctgctgc                                                                9

<210> SEQ ID NO 20
<211> LENGTH: 9
<212> TYPE: DNA
<213> ORGANISM: Artificial sequence
<220> FEATURE:
<223> OTHER INFORMATION: eukaryote replication origin
```

```
<400> SEQUENCE: 20 cagcagcag                                                                9

<210> SEQ ID NO 21
<211> LENGTH: 9
<212> TYPE: DNA
<213> ORGANISM: Artificial sequence
<220> FEATURE:
<223> OTHER INFORMATION: eukaryote replication origin

<400> SEQUENCE: 21 ctgctgctg                                                                9

<210> SEQ ID NO 22
<211> LENGTH: 12
<212> TYPE: DNA
<213> ORGANISM: Artificial sequence
<220> FEATURE:
<223> OTHER INFORMATION: eukaryote replication origin

<400> SEQUENCE: 22
ctctctctct ct                                                           12

<210> SEQ ID NO 23
<211> LENGTH: 12
<212> TYPE: DNA
<213> ORGANISM: Artificial sequence
<220> FEATURE:
<223> OTHER INFORMATION: eukaryote replication origin

<400> SEQUENCE: 23
tctctctctc tc                                                           12

<210> SEQ ID NO 24
<211> LENGTH: 13
<212> TYPE: DNA
<213> ORGANISM: Artificial sequence
<220> FEATURE:
<223> OTHER INFORMATION: eukaryote replication origin

<400> SEQUENCE: 24
agctggggcg gca                                                          13

<210> SEQ ID NO 25
<211> LENGTH: 13
<212> TYPE: DNA
<213> ORGANISM: Artificial sequence
<220> FEATURE:
<223> OTHER INFORMATION: eukaryote replication origin

<400> SEQUENCE: 25
cagctggggc ggc                                                          13

<210> SEQ ID NO 26
<211> LENGTH: 13
<212> TYPE: DNA
<213> ORGANISM: Artificial sequence
<220> FEATURE:
<223> OTHER INFORMATION: eukaryote replication origin

<400> SEQUENCE: 26
gctggggcgg cag                                                          13

<210> SEQ ID NO 27
```

```
<211> LENGTH: 13
<212> TYPE: DNA
<213> ORGANISM: Artificial sequence
<220> FEATURE:
<223> OTHER INFORMATION: eukaryote replication origin

<400> SEQUENCE: 27
agcagctgga cac                                                           13

<210> SEQ ID NO 28
<211> LENGTH: 13
<212> TYPE: DNA
<213> ORGANISM: Artificial sequence
<220> FEATURE:
<223> OTHER INFORMATION: eukaryote replication origin

<400> SEQUENCE: 28
cagcagctgg aca                                                           13

<210> SEQ ID NO 29
<211> LENGTH: 13
<212> TYPE: DNA
<213> ORGANISM: Artificial sequence
<220> FEATURE:
<223> OTHER INFORMATION: eukaryote replication origin

<400> SEQUENCE: 29
gcagcagctg gac                                                           13

<210> SEQ ID NO 30
<211> LENGTH: 13
<212> TYPE: DNA
<213> ORGANISM: Artificial sequence
<220> FEATURE:
<223> OTHER INFORMATION: eukaryote replication origin

<400> SEQUENCE: 30
cagctggaca cac                                                           13

<210> SEQ ID NO 31
<211> LENGTH: 13
<212> TYPE: DNA
<213> ORGANISM: Artificial sequence
<220> FEATURE:
<223> OTHER INFORMATION: eukaryote replication origin

<400> SEQUENCE: 31
agcagactgg gcg                                                           13

<210> SEQ ID NO 32
<211> LENGTH: 21
<212> TYPE: DNA
<213> ORGANISM: Artificial Sequence
<220> FEATURE:
<223> OTHER INFORMATION: ori from from mouse cc4 gene

<400> SEQUENCE: 32
gggggcgggg agggaagggg g                                                  21

<210> SEQ ID NO 33
<211> LENGTH: 27
<212> TYPE: DNA
<213> ORGANISM: Artificial Sequence
<220> FEATURE:
<223> OTHER INFORMATION: origin from mouse cc2 gene

<400> SEQUENCE: 33
```

```
gggggatggg gttggaatgg gggcggg                                    27
```

<210> SEQ ID NO 34
<211> LENGTH: 2001
<212> TYPE: DNA
<213> ORGANISM: Artificial Sequence
<220> FEATURE:
<223> OTHER INFORMATION: wt OGRE of cc2 gene

<400> SEQUENCE: 34

```
aaacacggga agcacttgaa acaatttcta gtctttatgg tggcatctgg gtcgaccaca    60
gacctagcac acagtagggg cgcaggctag acgaggcaga aggccgcagc gaagagacta   120
cgagaaagac aggggcccgc agggagaccg cggagatctc cggcgtcctt ccgggagcag   180
cccagcccaa cgccgcagct gtcaggccgc gggcggcggc gccagtccac caaacctgaa   240
agttccatcc cagcgcctcc accttcccag cctggacaag ttaccttgcg cccgctgctc   300
ccggtcccgc ccccgtcatc cattggtcga cgggttttctt tgttagcagg agcgtgcggg   360
tgccattggc tcgcggggct gccggttgcg gtgccccgcc ccaccccgcc cctccccgag   420
tgcgcgcggc gcccagctcg gttcgttcgc ggtggcggcg ggcgccgggt gagcgcgacg   480
gctggacttg ccggccggcg ccttgggggc ggccgcggtg gagccagcgg ccggaggccg   540
cgtccgtcca tgggcccaca gcggccgggc ggcggggcgg ggcgcgaggc ggcgcgcgcg   600
ctctgaggcc gcggcgagca ggcggggcgc ggcgcgagag gggaggcctt tccgggcctg   660
cggcggccag cgcaaaatgc ggcggcgcc gcgctgagtc cccgaccccc gggagagcgc   720
tgggccgtgg cggcccgctc cgcggccgcc tagccgacat gtcggcggcc aaggaaaacc   780
cgtgcaggaa atttcaggcc aacatcttca acaagagcaa gtgtcagaac tgcttcaagc   840
cccgcgagtc gcatctgctc aacgacgagg acctgacgca ggtgagctgc gcgggtgcg   900
gagctgagag tcctgcctgc gagtcgtgcc ggggagcgca gagcctgcga aggccaagag   960
agaataaaaa tggagcaggg aaaaaaaatg cgtgagagtt gggggatggg gttggaatgg  1020
gggcgggaag agtatcgata gagctgggac aaagggaaaa tcctcaagaa tgccgaaaaa  1080
taacatcctt tcccgttccc atagctctgc cgtgtgattc atgcttgttg ggtgactcaa  1140
aaaaatgtct ggtttccctg gataggaaca agtggggct tgcttgccac ttgtcagtac  1200
tacccccccc ctcgccccc tcgcgacttg tcttgggact ggacgcagac ttggccacca  1260
aactgtccca ggaattggca tgtttgcgtg ggtcaccagt ttccatcttg tggaatagag  1320
cctgctctcc ttctaagtca ctgtcaccgt cagggtctga agagagatga ggtgtttctc  1380
ttcagatggg tgggtcttgc tcttgaactg aaggtaggaa tagcttttgt cgaggggtag  1440
gggcttccct tcttggtttt gctttctggc ccaggagacc aagaagacct gtacattctg  1500
gggaaagttg gtttccccct ctgtctgccc ttaatttgtt agtcaggatt ttggaccagg  1560
ttagacgctc ttcctaaccc gtgtcaaagt cacagtcatg gaaaacagag ttccagacct  1620
ccaagtcaca gtcatggaaa acattgtcct agattgccaa agacctccaa ccccggagca  1680
gtgtaggaga ttgggaattt gtgttggtac aaggtctcca atttgggcaa ctggccctttg  1740
ggaactggtt gctctcccgt ttctggtgtt gaggattcct ggccttgttt gcagcacttt  1800
gggaaagcac tatatatcct gctccccttt cccctcgccc acttcctttg cccctgctt  1860
gctgacttca gtggagttcc ccacacggtc agccagtgc cacctagttg tagccactcc   1920
ttttggaaag agctgtttag actgaaaaca ttgctttgaa gtgccctggt ttggctgttt  1980
```

```
ttaaagcctt tatgggcaag c                                          2001
```

<210> SEQ ID NO 35
<211> LENGTH: 2001
<212> TYPE: DNA
<213> ORGANISM: Artificial Sequence
<220> FEATURE:
<223> OTHER INFORMATION: modified OGRE sequence (Deletion) of cc2 gene

<400> SEQUENCE: 35

```
aaacacggga agcacttgaa acaatttcta gtctttatgg tggcatctgg gtcgaccaca    60
gacctagcac acagtagggg cgcaggctag acgaggcaga aggccgcagc gaagagacta   120
cgagaaagac aggggcccgc agggagaccg cggagatctc cggcgtcctt ccgggagcag   180
cccagcccaa cgccgcagct gtcaggccgc gggcggcggc gccagtccac caaacctgaa   240
agttccatcc cagcgcctcc accttcccag cctggacaag ttaccttgcg cccgctgctc   300
ccggtcccgc ccccgtcatc cattggtcga cgggtttctt tgttagcagg agcgtgcggg   360
tgccattggc tcgcggggct gccggttgcg gtgccccgcc ccaccccgcc cctccccgag   420
tgcgcgcggc gcccagctcg gttcgttcgc ggtggcggcg ggcgccgggt gagcgcgacg   480
gctggacttg ccggccggcg ccttgggggc ggccgcggtg gagccagcgg ccggaggccg   540
cgtccgtcca tgggcccaca gcggccgggc ggcggggcgg ggcgcgaggc ggcgcgcgcg   600
ctctgaggcc gcggcgagca ggcggggcgc ggcgcgagag gggaggcctt ccgggcctg   660
cggcggccag cgcaaaatgc ggcggcggcc gcgctgagtc cccgaccccc gggagagcgc   720
tgggccgtgg cggcccgctc cgcggccgcc tagccgacat gtcggcggcc aaggaaaacc   780
cgtgcaggaa atttcaggcc aacatcttca acaagagcaa gtgtcagaac tgcttcaagc   840
cccgcgagtc gcatctgctc aacgacgagg acctgacgca ggtgagctgc gcggggtgcg   900
gagctgagag tcctgcctgc gagtcgtgcc ggggagcgca gagcctgcga aggccaagag   960
agaataaaaa tggagcaggg aaaaaaaatg cgtgagagtt ggggatggg gttgaatgg   1020
gggcgggaag agtatcgata gagctggac aaagggaaaa tcctcaagaa tgccgaaaaa  1080
taacatcctt tcccgttccc atagctctgc cgtgtgattc atgcttgttg ggtgactcaa  1140
aaaaatgtct ggttccctg gataggaaca agtgggct tgcttgccac ttgtcagtac  1200
tacccccccc ctcgccccc tcgcgactg tcttgggact ggacgcagac ttggccacca  1260
aactgtccca ggaattggca tgtttgcgtg gtcaccagt ttccatcttg tggaatagag  1320
cctgctctcc ttctaagtca ctgtcaccgt cagggtctga agagagatga ggtgttctc  1380
ttcagatggg tgggtcttgc tcttgaactg aaggtaggaa tagcttttgt cgaggggtag  1440
gggcttccct tcttggtttt gctttctggc ccaggagacc aagaagacct gtacattctg  1500
gggaaagttg gtttccccct ctgtctgccc ttaatttgtt agtcaggatt ttggaccagg  1560
ttagacgctc ttcctaaccc gtgtcaaagt cacagtcatg gaaaacagag ttccagacct  1620
ccaagtcaca gtcatggaaa acattgtcct agattgccaa agacctccaa ccccggagca  1680
gtgtaggaga ttgggaattt gtgttggtac aaggtctcca atttgggcaa ctggcccttg  1740
ggaactggtt gctctcccgt ttctggtgtt gaggattcct ggccttgttt gcagcacttt  1800
gggaaagcac tatatatcct gctccccttt cccctcgccc acttcctttg cccctgctt  1860
gctgacttca gtggagttcc ccacacggtc cagccagtgc cacctagttg tagccactcc  1920
ttttggaaag agctgtttag actgaaaaca ttgcttgaa gtgccctggt ttggctgttt  1980
ttaaagcctt tatgggcaag c                                          2001
```

<210> SEQ ID NO 36
<211> LENGTH: 2001
<212> TYPE: DNA
<213> ORGANISM: Artificial Sequence
<220> FEATURE:
<223> OTHER INFORMATION: modified OGRE sequence (random) of cc2 gene

<400> SEQUENCE: 36

| | | | | | |
|---|---|---|---|---|---|
| aaacacggga | agcacttgaa | acaatttcta | gtctttatgg | tggcatctgg | gtcgaccaca | 60 |
| gacctagcac | acagtagggg | cgcaggctag | acgaggcaga | aggccgcagc | gaagagacta | 120 |
| cgagaaagac | aggggcccgc | agggagaccg | cggagatctc | cggcgtcctt | ccggagcag | 180 |
| cccagcccaa | cgccgcagct | gtcaggccgc | gggcggcggc | gccagtccac | caaacctgaa | 240 |
| agttccatcc | cagcgcctcc | accttcccag | cctggacaag | ttaccttgcg | cccgctgctc | 300 |
| ccggtcccgc | ccccgtcatc | cattggtcga | cgggtttctt | tgttagcagg | agcgtgcggg | 360 |
| tgccattggc | tcgcggggct | gccggttgcg | gtgccccgcc | ccaccccgcc | cctcccgag | 420 |
| tgcgcgcggc | gcccagctcg | gttcgttcgc | ggtggcggcg | ggcgccgggt | gagcgcgacg | 480 |
| gctggacttg | ccggccggcg | ccttgggggc | ggccgcggtg | gagccagcgg | ccggaggccg | 540 |
| cgtccgtcca | tgggcccaca | gcggccgggc | ggcggggcgg | ggcgcgaggc | ggcgcgcgcg | 600 |
| ctctgaggcc | gcggcgagca | ggcggggcgc | ggcgcgagag | gggaggcctt | tccgggcctg | 660 |
| cggcggccag | cgcaaaatgc | ggcggcggcc | gcgctgagtc | cccgacccc | gggagagcgc | 720 |
| tgggccgtgg | cggcccgctc | cgcggccgcc | tagccgacat | gtcggcggcc | aaggaaaacc | 780 |
| cgtgcaggaa | atttcaggcc | aacatcttca | acaagagcaa | gtgtcagaac | tgcttcaagc | 840 |
| cccgcgagtc | gcatctgctc | aacgacgagg | acctgacgca | ggtgagctgc | gcgggtgcg | 900 |
| gagctgagag | tcctgcctgc | gagtcgtgcc | ggggagcgca | gagcctgcga | aggccaagag | 960 |
| agaataaaaa | tggagcaggg | aaaaaaaatg | cgtgagagtt | gctcgcgcac | cggtgtgagc | 1020 |
| tcctgccaag | agtatcgata | gagctgggac | aaagggaaaa | tcctcaagaa | tgccgaaaaa | 1080 |
| taacatcctt | tcccgttccc | atagctctgc | cgtgtgattc | atgcttgttg | ggtgactcaa | 1140 |
| aaaaatgtct | ggtttccctg | gataggaaca | aagtgggcgt | tgcttgccac | ttgtcagtac | 1200 |
| tacccccccc | ctcgcccccc | tcgcgacttg | tcttgggact | ggacgcagac | ttggccacca | 1260 |
| aactgtccca | ggaattggca | tgtttgcgtg | ggtcaccagt | ttccatcttg | tggaatagag | 1320 |
| cctgctctcc | ttctaagtca | ctgtcaccgt | cagggtctga | agagagatga | ggtgtttctc | 1380 |
| ttcagatggg | tgggtcttgc | tcttgaactg | aaggtaggaa | tagcttttgt | cgaggggtag | 1440 |
| gggcttccct | tcttggtttt | gctttctggc | ccaggagacc | aagaagacct | gtacattctg | 1500 |
| gggaaagttg | gtttccccct | ctgtctgccc | ttaatttgtt | agtcaggatt | ttggaccagg | 1560 |
| ttagacgctc | ttcctaaccc | gtgtcaaagt | cacagtcatg | gaaaacagag | ttccagacct | 1620 |
| ccaagtcaca | gtcatggaaa | acattgtcct | agattgccaa | agacctccaa | ccccggagca | 1680 |
| gtgtaggaga | ttgggaattt | gtgttggtac | aaggtctcca | atttgggcaa | ctggcccttg | 1740 |
| ggaactggtt | gctctcccgt | ttctggtgtt | gaggattcct | ggccttgttt | gcagcacttt | 1800 |
| gggaaagcac | tatatatcct | gctccccttt | ccctcgccc | acttcctttg | ccccctgctt | 1860 |
| gctgacttca | gtggagttcc | ccacacggtc | cagccagtgc | cacctagttg | tagccactcc | 1920 |
| ttttggaaag | agctgtttag | actgaaaaca | ttgctttgaa | gtgccctggt | ttggctgttt | 1980 |
| ttaaagcctt | tatgggcaag | c | | | | 2001 |